United States Patent
Lashinski et al.

(10) Patent No.: US 10,555,813 B2
(45) Date of Patent: Feb. 11, 2020

(54) IMPLANTABLE DEVICE AND DELIVERY SYSTEM FOR RESHAPING A HEART VALVE ANNULUS

(71) Applicant: BOSTON SCIENTIFIC SCIMED, INC., Maple Grove, MN (US)

(72) Inventors: Randall Lashinski, Windsor, CA (US); Kristian Kristoffersen, Redding, CA (US); Matthew Rust, Windsor, CA (US); Richard Glenn, Santa Rosa, CA (US); Terry Wayne Daniels, Occidental, CA (US); Michael Lee, Santa Rosa, CA (US); Patrick Macaulay, Windsor, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 239 days.

(21) Appl. No.: 15/352,288

(22) Filed: Nov. 15, 2016

(65) Prior Publication Data
US 2017/0135816 A1  May 18, 2017

Related U.S. Application Data

(60) Provisional application No. 62/256,660, filed on Nov. 17, 2015.

(51) Int. Cl.
*A61F 2/24* (2006.01)
*A61B 17/064* (2006.01)

(52) U.S. Cl.
CPC .......... *A61F 2/2445* (2013.01); *A61B 17/064* (2013.01); *A61F 2/2466* (2013.01);
(Continued)

(58) Field of Classification Search
CPC .......... A61F 2/82; A61F 2/848; A61F 2/2409; A61F 2/2442; A61F 2/2445; A61F 2002/9528
See application file for complete search history.

(56) References Cited

U.S. PATENT DOCUMENTS

| 3,143,742 A | 8/1964 | Cromie |
| 4,602,911 A | 7/1986 | Ahmadi et al. |

(Continued)

FOREIGN PATENT DOCUMENTS

| EP | 0 624 080 | 12/2001 |
| EP | 2 047 824 | 5/2012 |

(Continued)

OTHER PUBLICATIONS

International Search Report and Written Opinion dated May 26, 2017 for PCT/US2017/016284.

(Continued)

*Primary Examiner* — Sarah W Aleman

(57) ABSTRACT

Systems, devices and methods related to various heart valve implants and for delivery of those heart valve implants are described. The implants may be used to re-size a native valve annulus or to replace a native heart valve. The implants include a re-sizable frame having angled struts. Anchors secure the implant to tissue and collars are used to decrease the angle between the struts and contract the frame. The implant thus expands from a first size inside of a delivery catheter, to a second and larger deployed size inside the heart to engage and anchor with the tissue, and then to a third and contracted size to re-size the annulus and/or provide a secure fit for a replacement heart valve. Various delivery systems including imaging capabilities for precise delivery, positioning and anchoring of the various implants are further described.

25 Claims, 51 Drawing Sheets

(52) U.S. Cl.
CPC ................ *A61B 2017/0647* (2013.01); *A61B 2017/0649* (2013.01)

(56) References Cited

U.S. PATENT DOCUMENTS

| | | | |
|---|---|---|---|
| 4,820,299 A | 4/1989 | Philippe et al. | |
| 5,254,127 A | 10/1993 | Wholey et al. | |
| 5,370,685 A | 12/1994 | Stevens | |
| 5,674,279 A | 10/1997 | Wright et al. | |
| 5,674,280 A | 10/1997 | Davidson et al. | |
| 5,769,816 A | 6/1998 | Barbut et al. | |
| 5,772,590 A | 6/1998 | Webster, Jr. | |
| 5,810,882 A | 9/1998 | Bolduc | |
| 5,824,066 A | 10/1998 | Gross | |
| 5,968,053 A | 10/1999 | Revelas | |
| 5,984,959 A | 11/1999 | Robertson et al. | |
| 6,001,127 A | 12/1999 | Schoon et al. | |
| 6,059,731 A * | 5/2000 | Seward .................... | A61B 8/12 600/459 |
| 6,176,877 B1 | 1/2001 | Buchanan et al. | |
| 6,210,432 B1 | 4/2001 | Solem et al. | |
| 6,254,642 B1 | 7/2001 | Taylor | |
| 6,355,030 B1 | 3/2002 | Aldrich et al. | |
| 6,402,780 B2 | 6/2002 | Williamson et al. | |
| 6,582,460 B1 | 6/2003 | Cryer | |
| 6,652,537 B2 | 11/2003 | Mercereau et al. | |
| 6,676,692 B2 | 1/2004 | Rabkin et al. | |
| 6,695,878 B2 | 2/2004 | McGuckin et al. | |
| 6,702,826 B2 | 3/2004 | Liddicoat et al. | |
| 6,726,716 B2 | 4/2004 | Marquez | |
| 6,730,121 B2 | 5/2004 | Ortiz et al. | |
| 6,776,791 B1 | 8/2004 | Stallings et al. | |
| 6,786,925 B1 | 9/2004 | Schoon et al. | |
| 6,790,231 B2 | 9/2004 | Liddicoat et al. | |
| 6,805,710 B2 | 10/2004 | Bolling et al. | |
| 6,824,562 B2 | 11/2004 | Mathis et al. | |
| 6,875,231 B2 | 4/2005 | Anduiza et al. | |
| 6,913,608 B2 | 7/2005 | Liddicoat et al. | |
| 6,942,641 B2 | 9/2005 | Seddon | |
| 6,942,694 B2 | 9/2005 | Liddicoat et al. | |
| 6,951,571 B1 | 10/2005 | Srivastava | |
| 6,964,684 B2 | 11/2005 | Ortiz et al. | |
| 6,974,476 B2 | 12/2005 | McGuckin et al. | |
| 6,986,775 B2 | 1/2006 | Morales et al. | |
| 7,063,722 B2 | 1/2006 | Marquez | |
| 7,007,698 B2 | 3/2006 | Thornton | |
| 7,041,120 B2 | 5/2006 | Li et al. | |
| 7,081,131 B2 | 7/2006 | Thornton | |
| 7,087,064 B1 | 8/2006 | Hyde | |
| 7,112,219 B2 | 9/2006 | Vidlund et al. | |
| 7,160,322 B2 | 1/2007 | Gabbay | |
| 7,166,127 B2 | 1/2007 | Spence et al. | |
| 7,192,442 B2 | 3/2007 | Solam et al. | |
| 7,247,134 B2 | 7/2007 | Vidlund et al. | |
| 7,297,150 B2 | 11/2007 | Cartledge et al. | |
| 7,323,004 B2 | 1/2008 | Parihar | |
| 7,329,278 B2 | 2/2008 | Seguin et al. | |
| 7,329,280 B2 | 2/2008 | Bolling et al. | |
| 7,335,213 B1 | 2/2008 | Hyde et al. | |
| 7,357,815 B2 | 4/2008 | Shaoulian et al. | |
| 7,361,190 B2 | 4/2008 | Shaoulian et al. | |
| 7,381,218 B2 * | 6/2008 | Schreck ................ | A61F 2/2418 623/1.26 |
| 7,404,824 B1 | 7/2008 | Webler et al. | |
| 7,455,690 B2 | 11/2008 | Cartledge et al. | |
| 7,482,936 B2 | 1/2009 | Bolling | |
| 7,485,142 B2 | 2/2009 | Milo | |
| 7,507,252 B2 | 3/2009 | Lashinski et al. | |
| 7,527,646 B2 | 5/2009 | Randert et al. | |
| 7,556,647 B2 | 7/2009 | Drews et al. | |
| 7,611,534 B2 | 11/2009 | Kapadia et al. | |
| 7,637,946 B2 | 12/2009 | Solem et al. | |
| 7,655,040 B2 | 2/2010 | Douk et al. | |
| 7,674,222 B2 | 3/2010 | Nikolic et al. | |
| 7,691,144 B2 | 4/2010 | Chang et al. | |
| 7,695,510 B2 | 4/2010 | Bloom et al. | |
| 7,722,667 B1 | 5/2010 | Buchanan | |
| 7,731,649 B2 | 6/2010 | Ferrazzi | |
| 7,740,638 B2 | 6/2010 | Hyde | |
| D627,245 S | 11/2010 | Corn | |
| 7,850,709 B2 | 12/2010 | Cummins et al. | |
| 7,887,582 B2 | 2/2011 | Mathis et al. | |
| 7,896,913 B2 | 3/2011 | Damm et al. | |
| 7,914,576 B2 | 3/2011 | Navia et al. | |
| 7,914,577 B2 | 3/2011 | Cox | |
| 7,927,371 B2 | 4/2011 | Navia et al. | |
| 7,935,145 B2 | 5/2011 | Alfieri et al. | |
| 7,959,673 B2 | 6/2011 | Carpentier et al. | |
| 7,972,378 B2 | 7/2011 | Tabor et al. | |
| 7,988,725 B2 | 8/2011 | Gross et al. | |
| 7,993,395 B2 | 8/2011 | Vanermen et al. | |
| 8,012,202 B2 | 9/2011 | Alameddine | |
| 8,016,877 B2 | 9/2011 | Seguin et al. | |
| 8,052,751 B2 | 11/2011 | Aklog et al. | |
| 8,128,641 B2 | 3/2012 | Wardle | |
| 8,142,494 B2 | 3/2012 | Rahdert et al. | |
| 8,142,496 B2 | 3/2012 | Berreklouw | |
| 8,157,853 B2 | 4/2012 | Laske et al. | |
| 8,163,013 B2 | 4/2012 | Machold et al. | |
| 8,182,528 B2 | 5/2012 | Salahieh et al. | |
| 8,187,207 B2 | 5/2012 | Machold et al. | |
| 8,187,324 B2 | 5/2012 | Webler et al. | |
| 8,211,171 B2 | 7/2012 | Kim et al. | |
| 8,226,707 B2 | 7/2012 | White | |
| 8,277,502 B2 | 10/2012 | Miller et al. | |
| 8,287,555 B2 | 10/2012 | Starksen et al. | |
| 8,287,591 B2 | 10/2012 | Keidar et al. | |
| 8,333,777 B2 | 12/2012 | Schaller et al. | |
| 8,357,195 B2 | 1/2013 | Kuehn | |
| 8,366,766 B2 | 2/2013 | Berreklouw | |
| 8,382,653 B2 | 2/2013 | Dubi et al. | |
| 8,430,926 B2 | 4/2013 | Kirson | |
| 8,449,604 B2 | 5/2013 | Moaddeb et al. | |
| 8,454,683 B2 | 6/2013 | Rafiee et al. | |
| 8,480,733 B2 | 7/2013 | Navia et al. | |
| 8,512,403 B2 | 8/2013 | Navia et al. | |
| 8,551,161 B2 | 10/2013 | Dolan | |
| 8,551,162 B2 | 10/2013 | Fogarty et al. | |
| 8,560,009 B2 | 10/2013 | Etemad | |
| 8,579,964 B2 | 11/2013 | Lane et al. | |
| 8,603,159 B2 | 12/2013 | Seguin et al. | |
| 8,608,797 B2 | 12/2013 | Gross et al. | |
| 8,668,713 B2 | 3/2014 | Horan et al. | |
| 8,673,001 B2 | 3/2014 | Cartledge et al. | |
| 8,685,080 B2 | 4/2014 | White | |
| 8,690,858 B2 | 4/2014 | Machold et al. | |
| 8,690,939 B2 | 4/2014 | Miller et al. | |
| 8,715,342 B2 | 5/2014 | Zipory et al. | |
| 8,721,681 B2 | 5/2014 | Leung et al. | |
| 8,721,718 B2 | 5/2014 | Kassab | |
| 8,758,372 B2 | 6/2014 | Cartledge et al. | |
| 8,778,021 B2 | 7/2014 | Cartledge | |
| 8,784,482 B2 | 7/2014 | Rahdert et al. | |
| 8,808,371 B2 | 8/2014 | Cartledge | |
| 8,845,717 B2 | 9/2014 | Khairkhahan et al. | |
| 8,858,622 B2 | 10/2014 | Machold et al. | |
| 8,864,823 B2 | 10/2014 | Cartledge et al. | |
| 8,882,830 B2 | 11/2014 | Cartledge et al. | |
| 8,906,046 B2 | 12/2014 | Anderson | |
| 8,926,696 B2 | 1/2015 | Cabiri et al. | |
| 8,940,042 B2 | 1/2015 | Miller et al. | |
| 8,945,210 B2 | 2/2015 | Cartledge et al. | |
| 8,956,407 B2 | 2/2015 | Macoviak et al. | |
| 8,979,923 B2 | 3/2015 | Spence et al. | |
| 8,979,925 B2 | 3/2015 | Chang et al. | |
| 8,992,604 B2 | 3/2015 | Gross et al. | |
| 8,998,979 B2 | 4/2015 | Seguin | |
| 9,011,520 B2 | 4/2015 | Miller et al. | |
| 9,023,065 B2 | 5/2015 | Bolduc et al. | |
| 9,040,092 B2 | 5/2015 | Edelman et al. | |
| 9,044,221 B2 * | 6/2015 | Zentgraf ............... | A61F 2/2457 |
| 9,084,677 B2 | 7/2015 | Cartledge et al. | |
| 9,101,338 B2 | 8/2015 | Hindrichs et al. | |
| 9,107,749 B2 | 8/2015 | Bobo et al. | |

(56) References Cited

U.S. PATENT DOCUMENTS

| | | |
|---|---|---|
| 9,107,750 B2 | 8/2015 | Cartledge et al. |
| 9,119,718 B2 | 9/2015 | Keranen |
| 9,138,315 B2 | 9/2015 | Straubinger et al. |
| 9,180,005 B1 * | 11/2015 | Lashinski ............ A61F 2/2463 |
| 9,192,471 B2 | 11/2015 | Bolling |
| 9,198,755 B2 | 12/2015 | Shaolain et al. |
| 9,204,956 B2 | 12/2015 | Chanduszko et al. |
| 9,204,964 B2 | 12/2015 | Dahlgren et al. |
| 9,265,608 B2 | 2/2016 | Miller et al. |
| 9,301,756 B2 | 4/2016 | Wardle |
| 9,301,860 B2 | 4/2016 | White |
| 9,314,336 B2 | 4/2016 | Furnish et al. |
| 9,326,859 B2 | 5/2016 | Cartledge et al. |
| 9,339,379 B2 | 5/2016 | Quadri et al. |
| 9,351,830 B2 | 5/2016 | Gross et al. |
| RE46,126 E | 8/2016 | Kirson |
| RE46,127 E | 8/2016 | Kirson |
| 9,421,099 B2 | 8/2016 | Dolan |
| 9,427,215 B2 | 8/2016 | Cartledge et al. |
| 9,439,763 B2 | 9/2016 | Geist et al. |
| 9,474,606 B2 | 10/2016 | Zipory et al. |
| 9,492,276 B2 | 11/2016 | Lee et al. |
| 9,504,572 B2 | 11/2016 | Mauch et al. |
| 9,566,178 B2 | 2/2017 | Cartledge et al. |
| 9,585,747 B2 | 3/2017 | Quadri et al. |
| 9,592,122 B2 | 3/2017 | Zipory et al. |
| 9,610,156 B2 | 4/2017 | Lashinski |
| 9,730,790 B2 | 8/2017 | Quadri et al. |
| 9,744,038 B2 | 8/2017 | Dahlgren et al. |
| 9,788,941 B2 | 10/2017 | Hacohen |
| 9,801,714 B2 | 10/2017 | White |
| 9,827,093 B2 | 11/2017 | Cartledge et al. |
| 9,848,983 B2 * | 12/2017 | Lashinski ............ A61F 2/2409 |
| 2001/0044637 A1 | 11/2001 | Jacobs et al. |
| 2002/0002401 A1 | 1/2002 | McGuckin et al. |
| 2002/0042621 A1 | 4/2002 | Liddicoat et al. |
| 2002/0151961 A1 | 10/2002 | Lashinski et al. |
| 2002/0161377 A1 | 10/2002 | Rabkin |
| 2002/0173841 A1 | 11/2002 | Ortiz et al. |
| 2002/0183837 A1 | 12/2002 | Streeter et al. |
| 2003/0040793 A1 | 2/2003 | Marquez |
| 2003/0050693 A1 | 3/2003 | Quijano et al. |
| 2003/0083742 A1 | 5/2003 | Spence et al. |
| 2003/0093148 A1 | 5/2003 | Bolling |
| 2003/0158570 A1 | 8/2003 | Ferrazzi |
| 2003/0199974 A1 | 10/2003 | Lee et al. |
| 2003/0199975 A1 | 10/2003 | Gabbay |
| 2003/0199987 A1 | 10/2003 | Berg et al. |
| 2003/0212453 A1 | 11/2003 | Mathis et al. |
| 2003/0225420 A1 | 12/2003 | Wardle |
| 2003/0233142 A1 | 12/2003 | Morales et al. |
| 2004/0010275 A1 | 1/2004 | Jacobs et al. |
| 2004/0049266 A1 | 3/2004 | Anduiza et al. |
| 2004/0067544 A1 | 4/2004 | Vogel et al. |
| 2004/0092965 A1 | 5/2004 | Parihar |
| 2004/0122516 A1 | 6/2004 | Fogarty et al. |
| 2004/0127982 A1 | 7/2004 | Machold et al. |
| 2004/0133274 A1 | 7/2004 | Webler et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0167620 A1 | 8/2004 | Ortiz et al. |
| 2004/0172063 A1 | 9/2004 | Li et al. |
| 2004/0186565 A1 | 9/2004 | Schreck |
| 2004/0193191 A1 | 9/2004 | Starksen et al. |
| 2004/0193261 A1 | 9/2004 | Berreklouw |
| 2004/0236419 A1 | 11/2004 | Milo |
| 2004/0243104 A1 | 12/2004 | Seddon |
| 2004/0243227 A1 | 12/2004 | Starksen et al. |
| 2004/0243230 A1 | 12/2004 | Navia et al. |
| 2004/0249400 A1 | 12/2004 | Vargas et al. |
| 2004/0249453 A1 | 12/2004 | Cartledge et al. |
| 2004/0260394 A1 | 12/2004 | Douk et al. |
| 2005/0004665 A1 | 1/2005 | Aklog |
| 2005/0004668 A1 | 1/2005 | Aklog et al. |
| 2005/0038508 A1 | 2/2005 | Gabbay |
| 2005/0049692 A1 | 3/2005 | Numamoto |
| 2005/0075713 A1 | 4/2005 | Biancucci et al. |
| 2005/0080454 A1 | 4/2005 | Drews et al. |
| 2005/0119734 A1 | 6/2005 | Spence et al. |
| 2005/0131533 A1 | 6/2005 | Alfieri et al. |
| 2005/0137701 A1 | 6/2005 | Salahieh et al. |
| 2005/0177180 A1 | 8/2005 | Kaganov et al. |
| 2005/0182290 A1 | 8/2005 | Lau et al. |
| 2005/0182486 A1 | 8/2005 | Gabbay |
| 2005/0192629 A1 | 9/2005 | Saadat et al. |
| 2005/0197696 A1 | 9/2005 | Gomez |
| 2005/0234508 A1 | 10/2005 | Cummins et al. |
| 2005/0250986 A1 | 11/2005 | Rothe et al. |
| 2005/0267560 A1 | 12/2005 | Bates |
| 2005/0267572 A1 | 12/2005 | Schoon et al. |
| 2005/0288776 A1 | 12/2005 | Shaoulian et al. |
| 2005/0288783 A1 | 12/2005 | Shaoulian et al. |
| 2006/0015178 A1 | 1/2006 | Moaddeb et al. |
| 2006/0025854 A1 | 2/2006 | Lashinski et al. |
| 2006/0025855 A1 | 2/2006 | Lashinski et al. |
| 2006/0025858 A1 | 2/2006 | Alameddine |
| 2006/0100699 A1 | 5/2006 | Vidlund et al. |
| 2006/0106305 A1 | 5/2006 | Lau |
| 2006/0106456 A9 | 5/2006 | Machold et al. |
| 2006/0129235 A1 | 6/2006 | Seguin et al. |
| 2006/0149349 A1 | 7/2006 | Garbe |
| 2006/0149368 A1 | 7/2006 | Spence |
| 2006/0178733 A1 | 8/2006 | Pinchuk et al. |
| 2006/0184240 A1 | 8/2006 | Jimenez et al. |
| 2006/0184241 A1 | 8/2006 | Marquez |
| 2006/0195012 A1 | 8/2006 | Mortier et al. |
| 2006/0206203 A1 | 9/2006 | Yang et al. |
| 2006/0229708 A1 | 10/2006 | Powell et al. |
| 2006/0241746 A1 | 10/2006 | Shaoulian et al. |
| 2006/0241747 A1 | 10/2006 | Shaoulian et al. |
| 2006/0241748 A1 | 10/2006 | Lee et al. |
| 2006/0282161 A1 | 12/2006 | Huynh et al. |
| 2006/0282162 A1 | 12/2006 | Nguyen et al. |
| 2007/0005129 A1 | 1/2007 | Damm et al. |
| 2007/0016287 A1 | 1/2007 | Cartledge et al. |
| 2007/0016288 A1 | 1/2007 | Gurskis et al. |
| 2007/0027533 A1 | 2/2007 | Douk |
| 2007/0027536 A1 | 2/2007 | Mihaljevic et al. |
| 2007/0049942 A1 | 3/2007 | Hindrichs et al. |
| 2007/0050019 A1 | 3/2007 | Hyde |
| 2007/0055368 A1 | 3/2007 | Rhee et al. |
| 2007/0083259 A1 | 4/2007 | Bloom et al. |
| 2007/0093890 A1 | 4/2007 | Eliasen et al. |
| 2007/0112423 A1 | 5/2007 | Chu |
| 2007/0112425 A1 | 5/2007 | Schaller et al. |
| 2007/0142907 A1 | 6/2007 | Moaddeb et al. |
| 2007/0156233 A1 | 7/2007 | Kapadia et al. |
| 2007/0161846 A1 | 7/2007 | Nikolic et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0265701 A1 | 11/2007 | Gurskis et al. |
| 2007/0276478 A1 | 11/2007 | Marmureanu et al. |
| 2007/0282436 A1 | 12/2007 | Pinchuk |
| 2007/0293942 A1 | 12/2007 | Mirzaee |
| 2007/0299543 A1 | 12/2007 | Cartledge et al. |
| 2008/0027483 A1 | 1/2008 | Cartledge et al. |
| 2008/0067713 A1 | 3/2008 | Bordener |
| 2008/0071364 A1 | 3/2008 | Kaye et al. |
| 2008/0077235 A1 | 3/2008 | Kirson |
| 2008/0177380 A1 | 7/2008 | Starksen et al. |
| 2008/0255661 A1 | 10/2008 | Straubinger et al. |
| 2008/0288060 A1 | 11/2008 | Kaye et al. |
| 2009/0082857 A1 | 3/2009 | Lashinski et al. |
| 2009/0087414 A1 | 4/2009 | Edelman et al. |
| 2009/0149872 A1 | 6/2009 | Gross et al. |
| 2009/0177276 A1 | 7/2009 | Carpentier et al. |
| 2009/0182419 A1 | 7/2009 | Bolling |
| 2009/0198316 A1 | 8/2009 | Laske et al. |
| 2009/0264996 A1 | 10/2009 | Vanermen et al. |

(56) References Cited

U.S. PATENT DOCUMENTS

| | | |
|---|---|---|
| 2009/0276040 A1 | 11/2009 | Rowe et al. |
| 2009/0287299 A1 | 11/2009 | Tabor et al. |
| 2009/0287304 A1 | 11/2009 | Dahlgren et al. |
| 2009/0306622 A1 | 12/2009 | Machold |
| 2010/0004740 A1 | 1/2010 | Sequin et al. |
| 2010/0049315 A1 | 2/2010 | Kirson |
| 2010/0087855 A1 | 4/2010 | Leung et al. |
| 2010/0100174 A1 | 4/2010 | Gurskis |
| 2010/0121433 A1 | 5/2010 | Bolling |
| 2010/0152838 A1 | 6/2010 | Kang et al. |
| 2010/0152840 A1 | 6/2010 | Seguin et al. |
| 2010/0152845 A1 | 6/2010 | Bloom et al. |
| 2010/0185229 A1 | 7/2010 | Horan |
| 2010/0249920 A1 | 9/2010 | Bolling |
| 2010/0280604 A1 | 11/2010 | Zipory et al. |
| 2010/0298929 A1 | 11/2010 | Thornton |
| 2011/0022166 A1 | 1/2011 | Dahlgren et al. |
| 2011/0060407 A1 | 3/2011 | Ketai et al. |
| 2011/0066224 A1 | 3/2011 | White |
| 2011/0066236 A1 | 3/2011 | Khalapyan |
| 2011/0106245 A1 | 5/2011 | Miller et al. |
| 2011/0106247 A1 | 5/2011 | Miller et al. |
| 2011/0172760 A1 | 7/2011 | Anderson |
| 2011/0190879 A1 | 8/2011 | Bobo et al. |
| 2011/0202127 A1 | 8/2011 | Mauch et al. |
| 2011/0219603 A1 | 9/2011 | White |
| 2011/0224785 A1 | 9/2011 | Hacohen |
| 2011/0230961 A1 | 9/2011 | Langer et al. |
| 2011/0288632 A1 | 11/2011 | White |
| 2011/0319989 A1 | 12/2011 | Lane et al. |
| 2012/0022640 A1 | 1/2012 | Gross et al. |
| 2012/0027116 A1 | 2/2012 | Etemad |
| 2012/0053680 A1 | 3/2012 | Bolling et al. |
| 2012/0109288 A1 | 5/2012 | Bolling |
| 2012/0109289 A1 | 5/2012 | Bolling |
| 2012/0203330 A1 | 8/2012 | Cartledge et al. |
| 2012/0209379 A1 | 8/2012 | Shaolian et al. |
| 2012/0215303 A1 | 8/2012 | Quadri |
| 2012/0283757 A1 | 11/2012 | Miller et al. |
| 2012/0308610 A1 | 12/2012 | Edelman et al. |
| 2013/0006295 A1 | 1/2013 | Chanduszko |
| 2013/0030523 A1 | 1/2013 | Padala et al. |
| 2013/0046373 A1* | 2/2013 | Cartledge ................. A61F 2/95 623/1.11 |
| 2013/0123910 A1 | 5/2013 | Cartledge et al. |
| 2013/0123913 A1 | 5/2013 | Kuehn |
| 2013/0138207 A1 | 5/2013 | Quadri |
| 2013/0177600 A1 | 7/2013 | Edelman et al. |
| 2013/0226289 A1 | 8/2013 | Shaolian et al. |
| 2013/0296999 A1* | 11/2013 | Burriesci ............. A61F 2/2436 623/1.11 |
| 2013/0325118 A1 | 12/2013 | Cartledge |
| 2014/0039612 A1 | 2/2014 | Dolan |
| 2014/0142695 A1 | 5/2014 | Gross et al. |
| 2014/0163690 A1 | 6/2014 | White |
| 2014/0222136 A1 | 8/2014 | Geist et al. |
| 2014/0277427 A1 | 9/2014 | Ratz et al. |
| 2014/0277563 A1 | 9/2014 | White |
| 2014/0296962 A1 | 10/2014 | Cartledge et al. |
| 2014/0309731 A1 | 10/2014 | Quadri et al. |
| 2014/0336756 A1 | 11/2014 | Lee et al. |
| 2015/0081014 A1* | 3/2015 | Gross .................... A61F 2/2445 623/2.37 |
| 2015/0112432 A1 | 4/2015 | Reich et al. |
| 2015/0127096 A1 | 5/2015 | Rowe et al. |
| 2015/0142105 A1 | 5/2015 | Bolling et al. |
| 2015/0157459 A1 | 6/2015 | Macoviak |
| 2015/0250461 A1 | 9/2015 | Berreklouw |
| 2016/0008130 A1 | 1/2016 | Hasin |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0038285 A1 | 2/2016 | Glenn et al. |
| 2016/0095704 A1 | 4/2016 | Whitman |
| 2016/0120645 A1 | 5/2016 | Alon |
| 2016/0128829 A1 | 5/2016 | Oba |
| 2016/0235526 A1 | 8/2016 | Lashinski et al. |
| 2016/0256276 A1 | 9/2016 | Yaron |
| 2016/0317304 A1 | 11/2016 | Spence et al. |
| 2016/0324638 A1 | 11/2016 | Dolan et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0035564 A1 | 2/2017 | Ryan |
| 2017/0049570 A1 | 2/2017 | O'Beirne et al. |
| 2017/0086974 A1 | 3/2017 | Lashinski et al. |
| 2017/0143488 A1 | 5/2017 | Lashinski et al. |
| 2017/0143489 A1 | 5/2017 | Lashinski et al. |
| 2017/0156860 A1 | 6/2017 | Lashinski et al. |
| 2017/0209253 A1 | 7/2017 | Lashinski et al. |
| 2017/0231759 A1 | 8/2017 | Geist |
| 2017/0348098 A1 | 12/2017 | Rowe et al. |
| 2017/0360549 A1 | 12/2017 | Lashinski et al. |

FOREIGN PATENT DOCUMENTS

| | | |
|---|---|---|
| EP | 2 656 816 | 10/2013 |
| JP | 2008-538937 | 11/2008 |
| JP | 2010-284536 | 12/2010 |
| WO | WO 90/09153 | 8/1990 |
| WO | WO 93/15690 | 8/1993 |
| WO | WO 97/12565 | 4/1997 |
| WO | WO 97/20524 | 6/1997 |
| WO | WO 98/24386 | 6/1998 |
| WO | WO 99/29269 | 6/1999 |
| WO | WO 99/49816 | 10/1999 |
| WO | WO 00/07521 | 2/2000 |
| WO | WO 00/18333 | 4/2000 |
| WO | WO 00/44311 | 8/2000 |
| WO | WO 00/62715 | 10/2000 |
| WO | WO 01/89440 | 11/2001 |
| WO | WO 02/034121 | 5/2002 |
| WO | WO 02/094132 | 11/2002 |
| WO | WO 03/017874 | 3/2003 |
| WO | WO 03/053289 | 7/2003 |
| WO | WO 03/080150 | 10/2003 |
| WO | WO 03/105670 | 12/2003 |
| WO | WO 03/105730 | 12/2003 |
| WO | WO 04/014282 | 2/2004 |
| WO | WO 04/019816 | 3/2004 |
| WO | WO 04/019826 | 3/2004 |
| WO | WO 04/030569 | 4/2004 |
| WO | WO 04/031717 | 4/2004 |
| WO | WO 04/032717 | 4/2004 |
| WO | WO 04/082538 | 9/2004 |
| WO | WO 04/103223 | 12/2004 |
| WO | WO 04/112657 | 12/2004 |
| WO | WO 05/002424 | 1/2005 |
| WO | WO 05/007037 | 1/2005 |
| WO | WO 05/046488 | 5/2005 |
| WO | WO 05/087139 | 9/2005 |
| WO | WO 06/011275 | 2/2006 |
| WO | WO 06/052687 | 5/2006 |
| WO | WO 06/086135 | 8/2006 |
| WO | WO 06/086434 | 8/2006 |
| WO | WO 06/105084 | 10/2006 |
| WO | WO 06/116129 | 11/2006 |
| WO | WO 06/116357 | 11/2006 |
| WO | WO 07/021834 | 2/2007 |
| WO | WO 07/103562 | 9/2007 |
| WO | WO 07/136783 | 11/2007 |
| WO | WO 08/15257 | 2/2008 |
| WO | WO 08/068756 | 6/2008 |
| WO | WO 08/088716 | 7/2008 |
| WO | WO 09/120764 | 10/2009 |
| WO | WO 09/126629 | 10/2009 |
| WO | WO 09/140268 | 11/2009 |
| WO | WO 10/011699 | 1/2010 |
| WO | WO 10/048151 | 4/2010 |
| WO | WO 12/027116 | 3/2012 |
| WO | WO 2012/167095 | 12/2012 |

(56) References Cited

FOREIGN PATENT DOCUMENTS

WO    WO 2013/088327    6/2013
WO    WO 15/77599    5/2015

OTHER PUBLICATIONS

Invitation to Pay Additional Search Fees dated Feb. 14, 2017 in PCT/US16/062107.
International Search Report and Written Opinion dated Apr. 19, 2017 in PCT/US16/062107.
B. Braun Medical Inc., "Pulmonary Embolism: IVC Filters." Retrieved from the Internet: http://www.bbraunusa.com/pe/pe05a.html, 2004, 2 pages.
Bonow et al., "ACC/AHA 2006 Guidelines for the Management of Patients with Valvular Heart Disease," J. American College of Cardiology, 48(3):e1-148 (2006).
Boston Scientific, "Device Details." Retrieved from the Internet: http://bostonscientific.com/med_specialty/deviceDetail.jsp [retrieved on Aug. 31, 2006], 1 page.
Braunberger et al., "Very Long-Term Results (More Than 20 years) of Valve Repair with Carpentier's Techniques in Nonrheumatic Mitral Valve Insufficiency," Circulation, 104:18-111 (2001).
Braunwald et al., "Conservative Management of tricuspid Regurgitation in Patients Undergoing Mitral Valve Replacement," Circulation, XXXV and XXXVI:I63-I69 (1967).
Carpentier et al., "Surgical Management of Acquired Tricuspid Valve Disease," J. Thoracic and Cardiovascular Surgery, 67(1):53-65 (1974).
Center for Devices and Radiological Health, U.S. Dept. of Health and Human Services Food and Drug Administration "Guidance for Annuloplasty Rings 510(k) Submissions; Final Guidance for Industry and FDA Staff," 1-15 (2001).
Cosgrove et al., "Mitral Valvuloplasty," Curro. Probl. Cardiol., 359-405 (1989).
Dreyfus et al., "Secondary Tricuspid Regurgitation or Dilatation: Which Should Be the Criteria for Surgical Repair?," Ann. Thorac. Surg., 79:127-32 (2005).
Google Images, Recurved Hooks. Retrieved from the Internet: www.implementology.org.pf and personal.cityu.edu.hk [retrieved on Dec. 14, 2006], 1 page.
Leung et al., "Barbed, Bi-directional Surgical Sutures: In Vivo Strength and Histopathology Evaluations," Society for Biomaterials 28th Annual Meeting Transactions, #724 (2003) 1 p.
Magovern et al., "Sutureless Artificial Heart Valves," Circulation, 27:784-788 (1963).
McCarthy et al., "Tricuspid Valve Repair: Durability and Risk Factors for Failure," J. Thoracic and Cardiovascular Surgery, 127:674-85 (2004).
Nath et al., "Impact of Tricuspid Regurgitation on Long-Term Survival," J. American College of Cardiology, 43(3):405-409 (2004).
Navia et al., "Surgical Management of Secondary Tricuspid Valve Regurgitation: Anulus, Commissure, or Leaflet Procedure?," Abstract presented at American Association for Thoracic Surgery Annual Meeting (2009).
Rogers et al., "The Tricuspid Valve: Current Perspective and Evolving Management of Tricuspid Regurgitation," Circulation, 119:2718-2725 (2009).
Sagie et al., "Determinants of Functional Tricuspid Regurgitation in Incomplete Tricuspid Valve Closure: Doppler Color Flow Study of 109 Patients," J. American College of Cardiology, 24:446-53 (1994).
Savage et al., "Use of Mitral Valve Repair: Analysis of Contemporary United States Experience Reported to the Society of Thoracic Surgeons National Cardiac Database," Ann. Thorac Surg., 75:820-825 (2003).
Shiran et al., "Tricuspid Regurgitation in Mitral Valve Disease," J. American College of Cardiology, 53(5):401-408 (2009).
Song et al., "Factors Associated with Development of Late Significant Tricuspid Regurgitation after Successful Left-Sided Valve Surgery," Heart, 95:931-936 (2009).
Tang et al., "Tricuspid Valve Repair with an Annuloplasty Ring Results in Improved Long-Term Outcomes," Circulation, 114:1577-1581 (2006).
Thompson, "Percutaneous Heart Valve Technology: The Mitral Challenge," Medtech Insight, 11(2):38-52 (2009).
Zlotnick et al., "A Perfectly Functioning Magovem-Cromie Sutureless Prosthetic Aortic Valve 42 Years After Implantation," Circulation, 117:e1-e2 (2008).
International Search Report dated Jun. 18, 2018, for PCT/US18/17679 (4 pages).

* cited by examiner

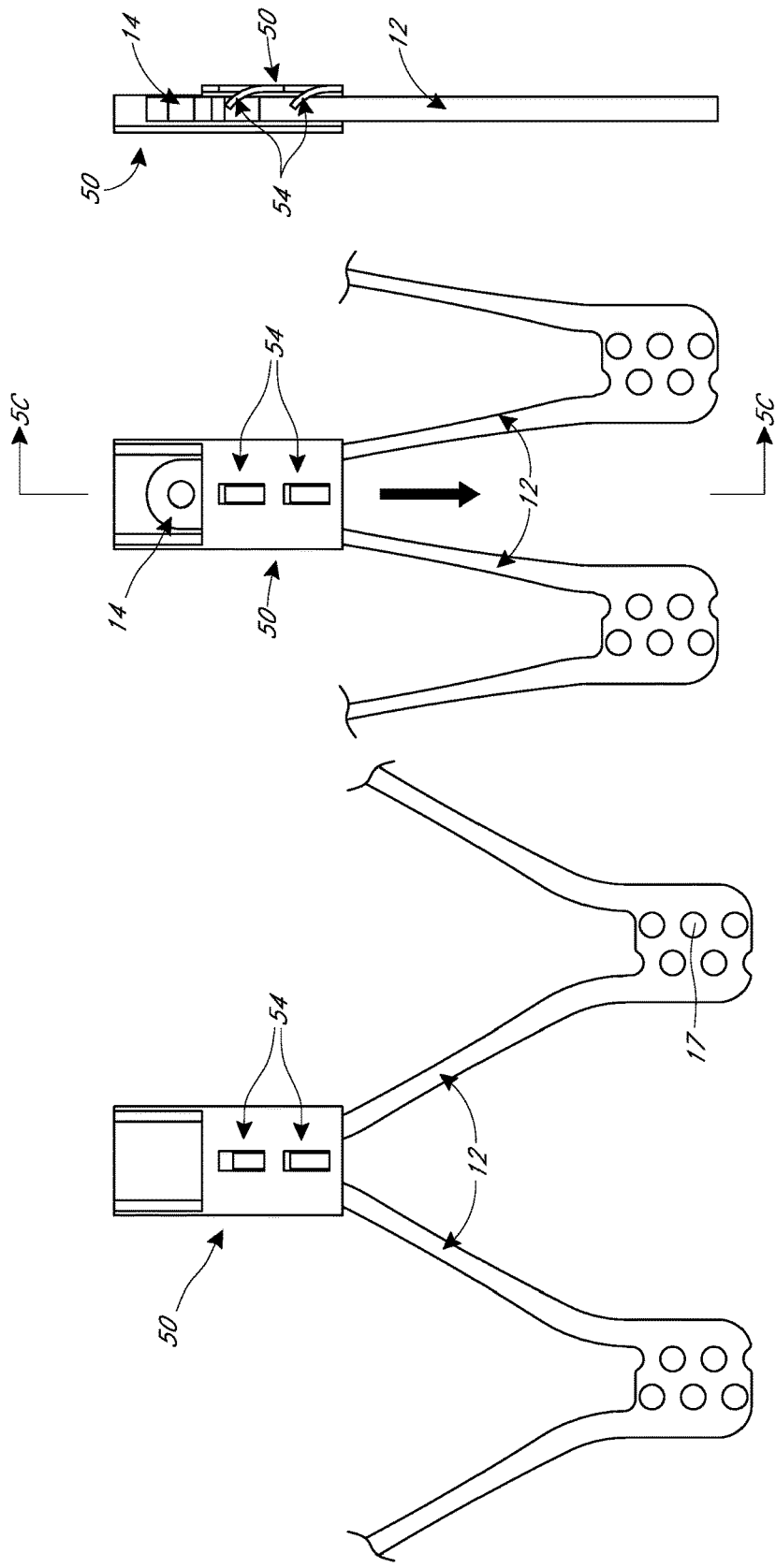

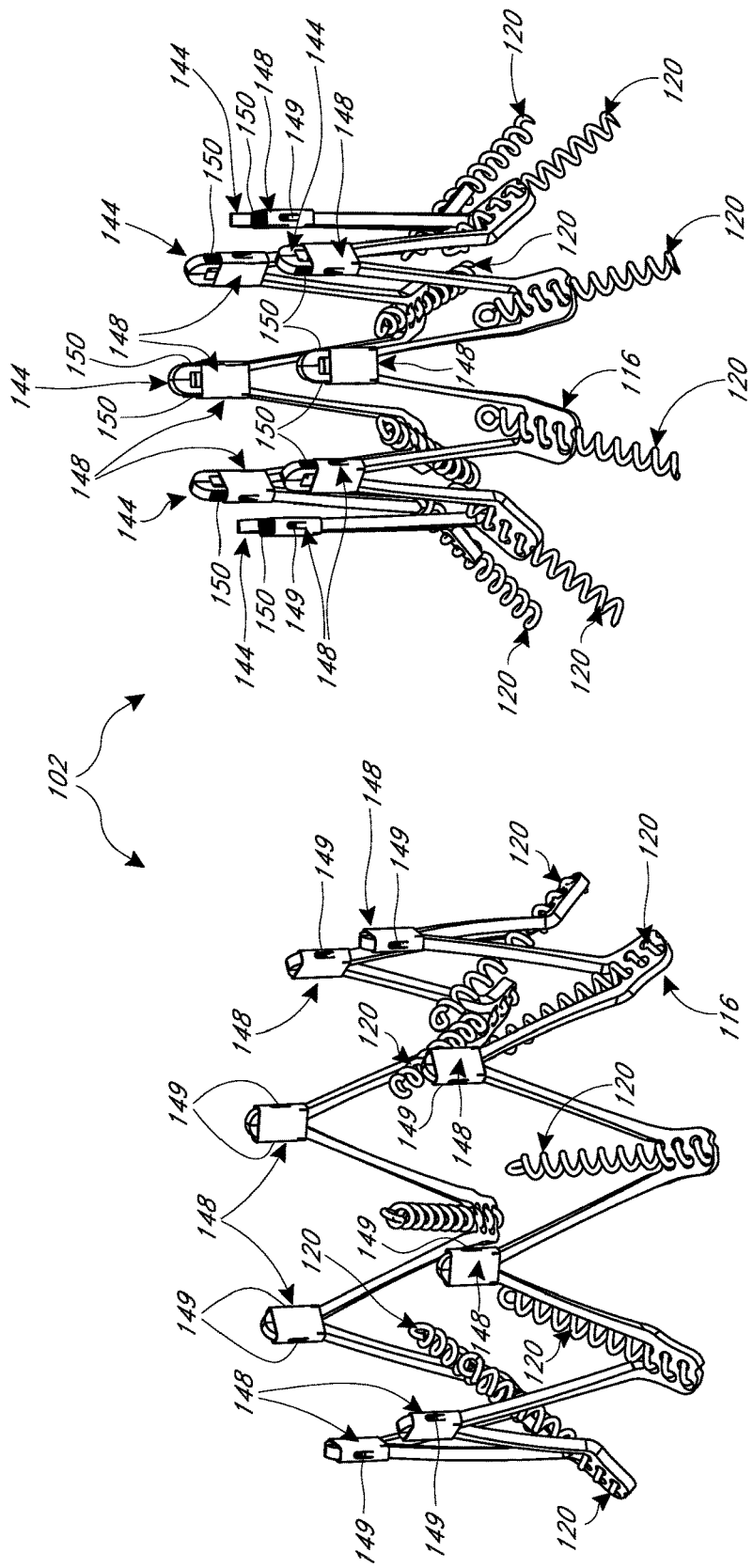

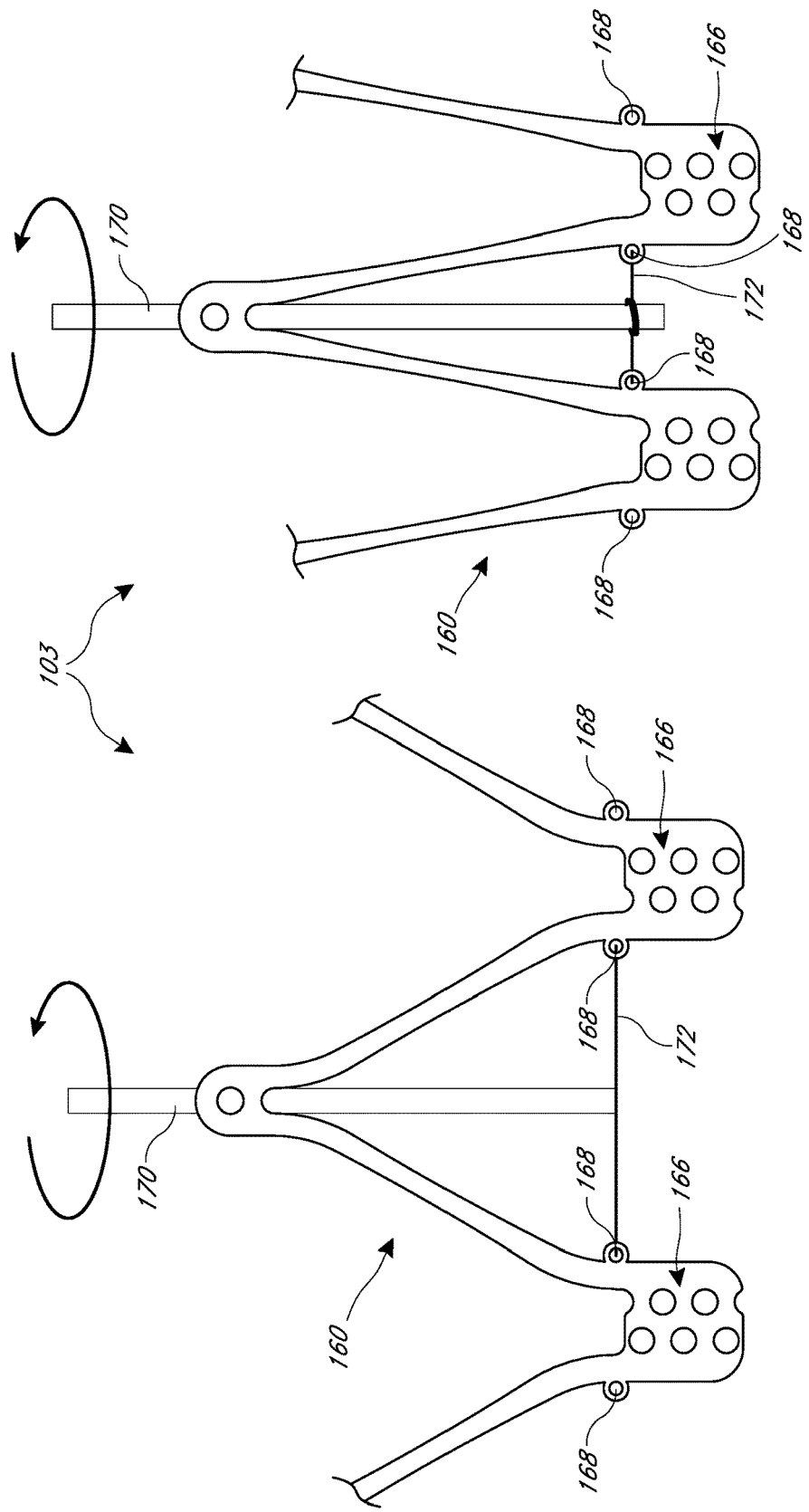

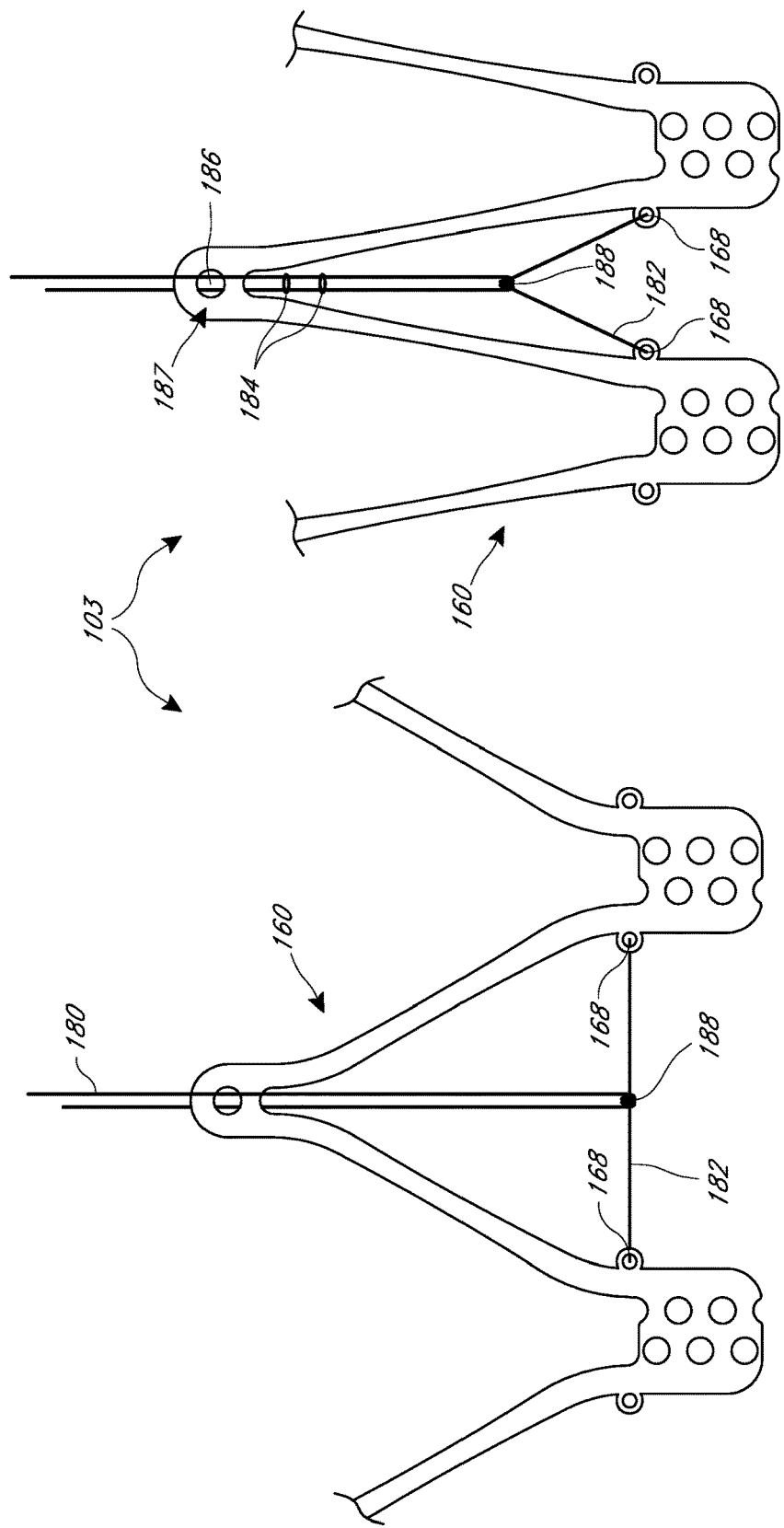

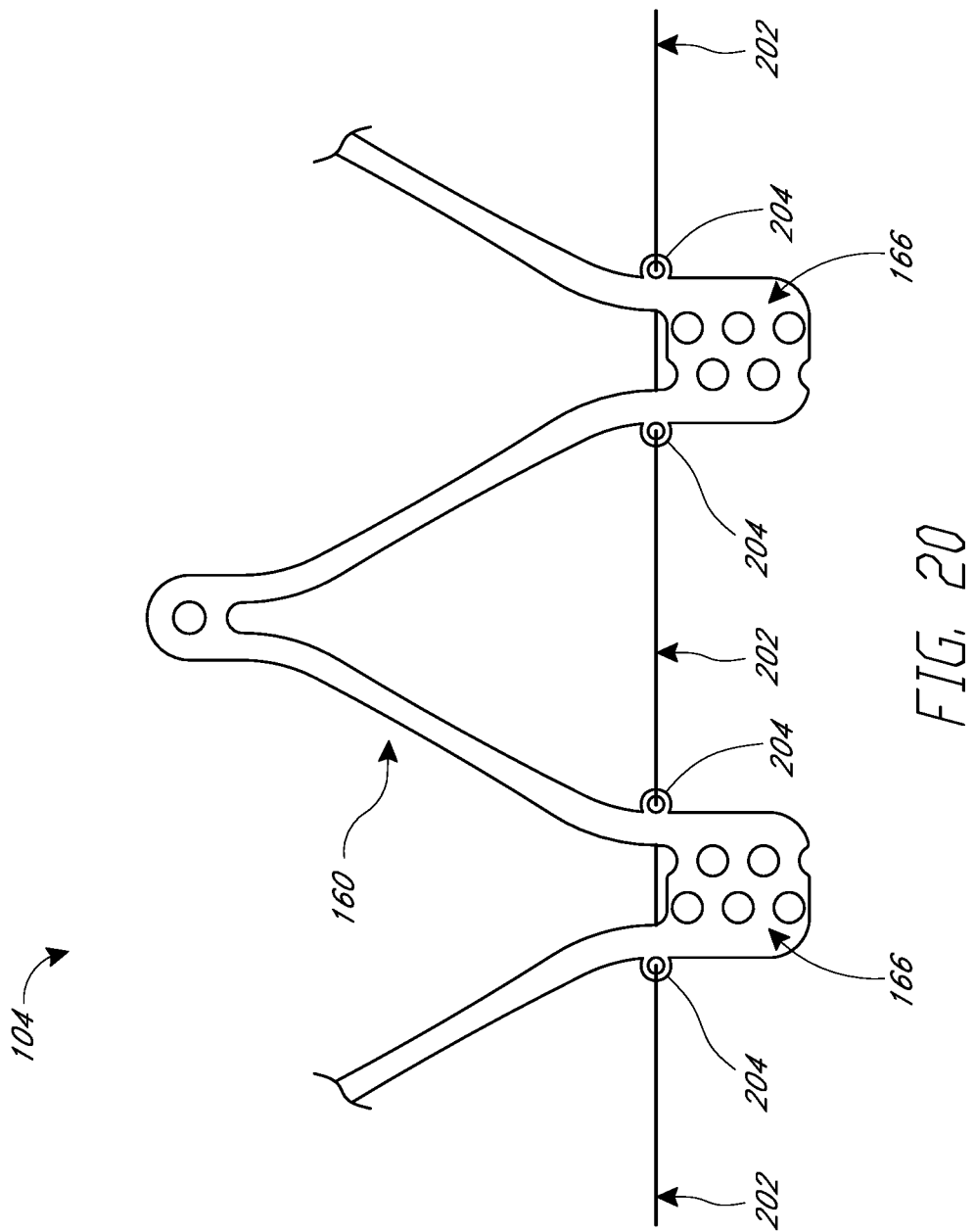

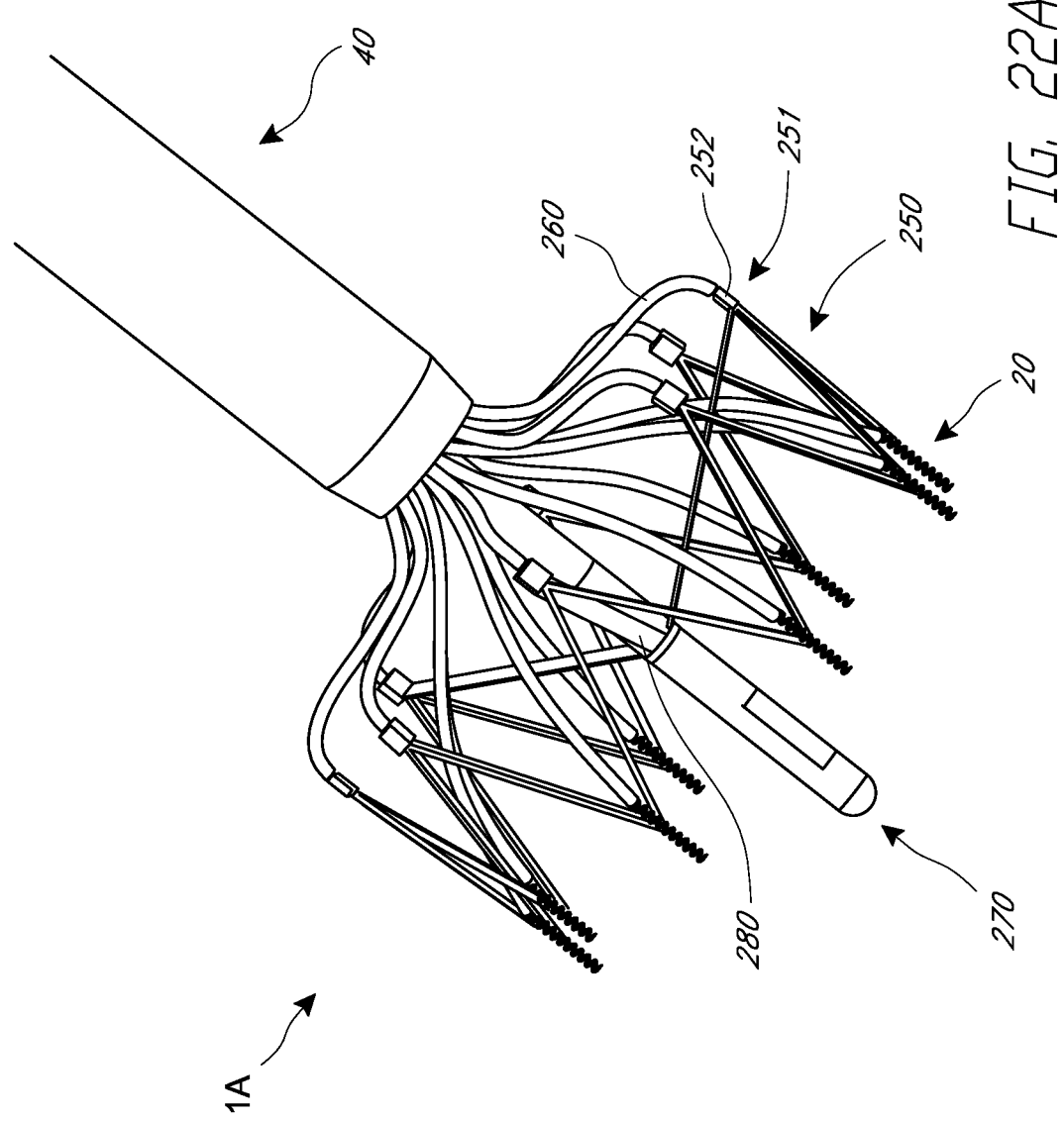

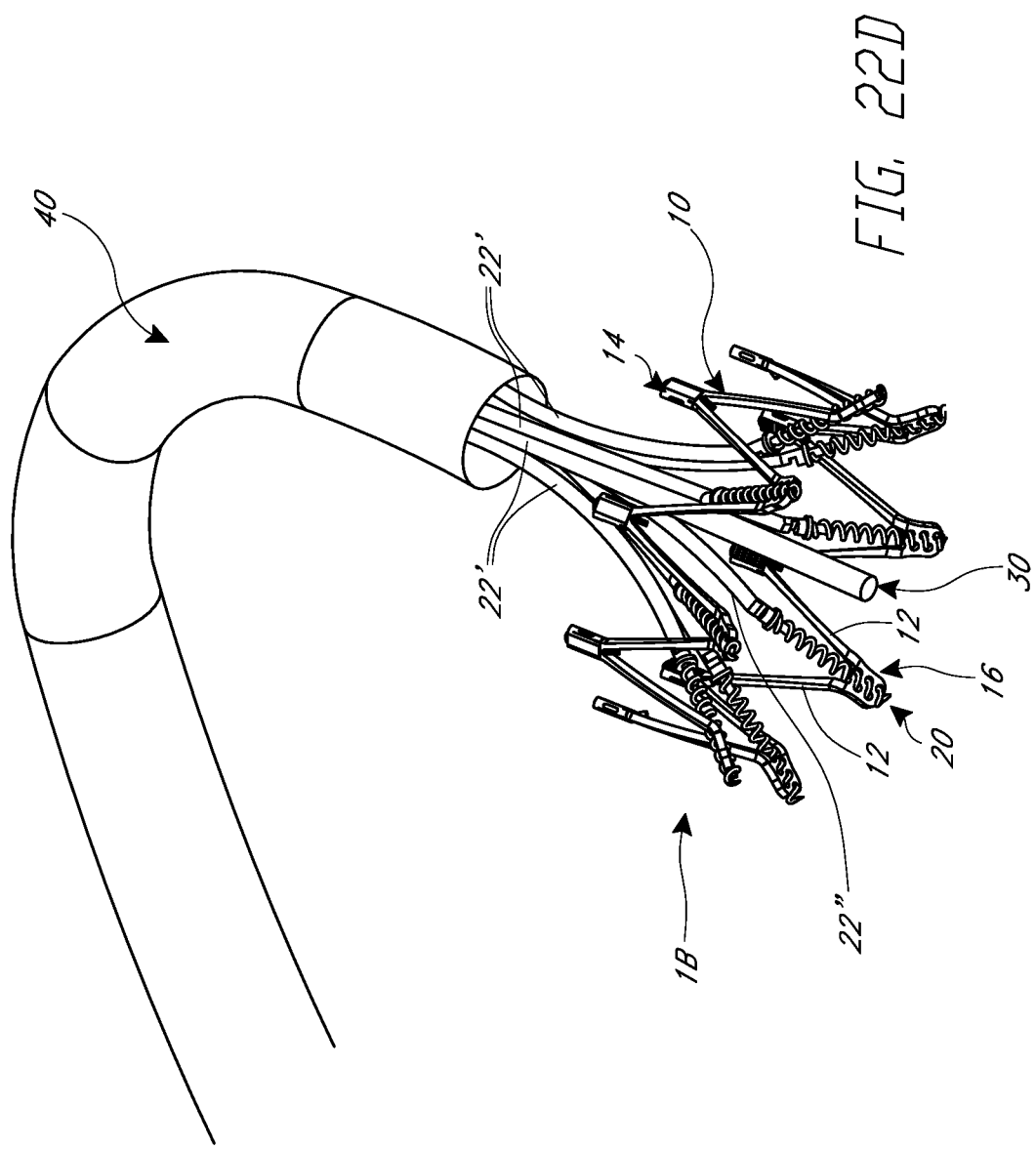

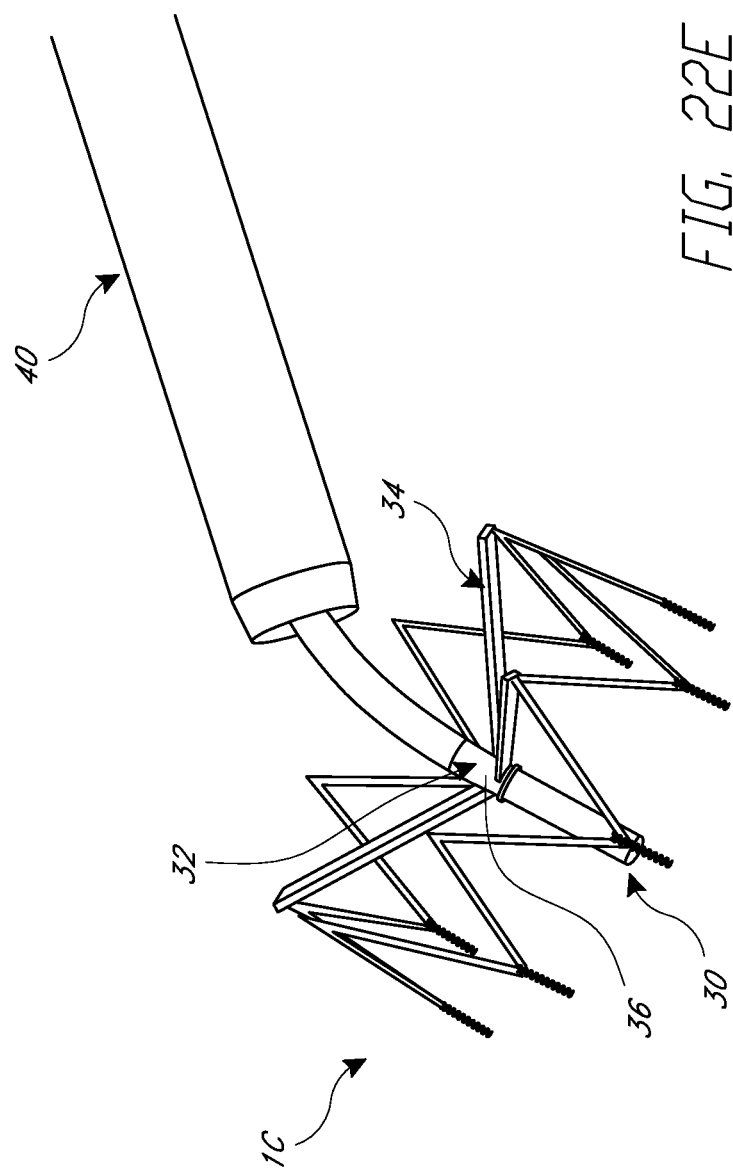

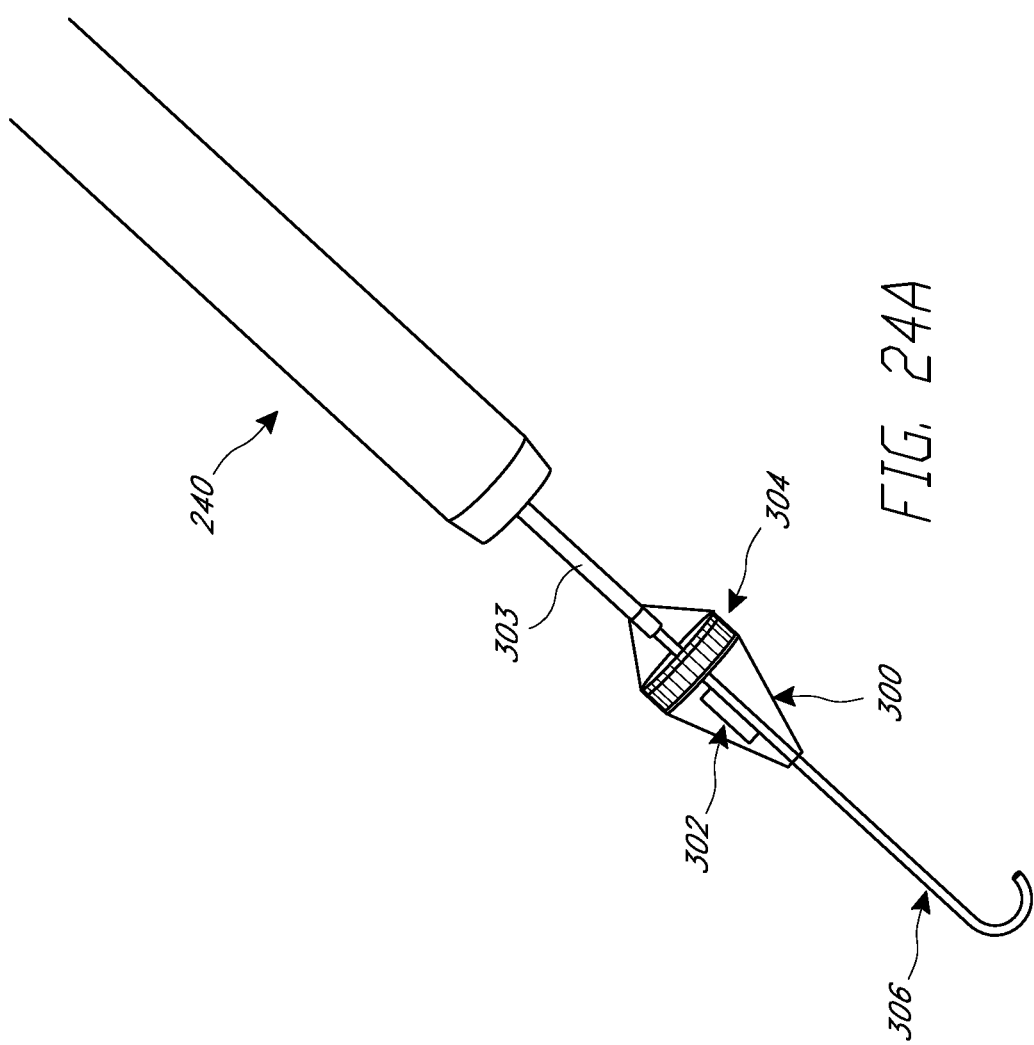

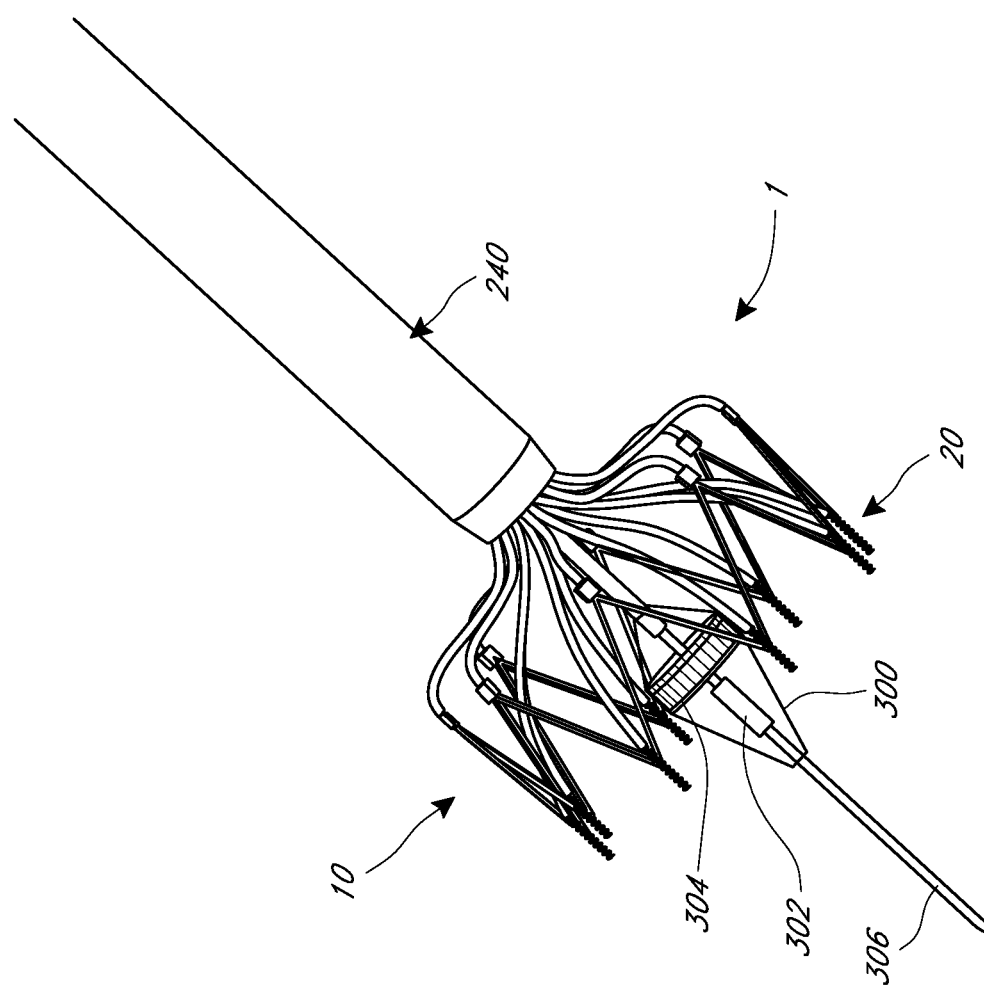

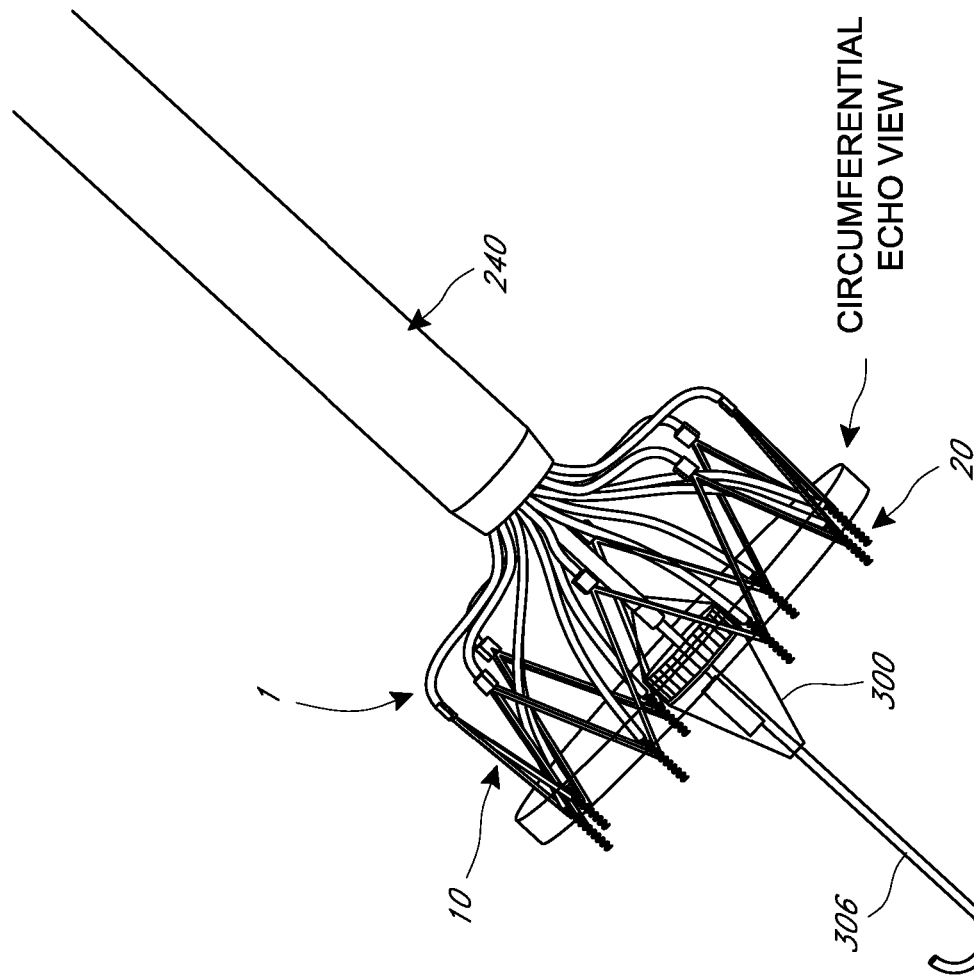

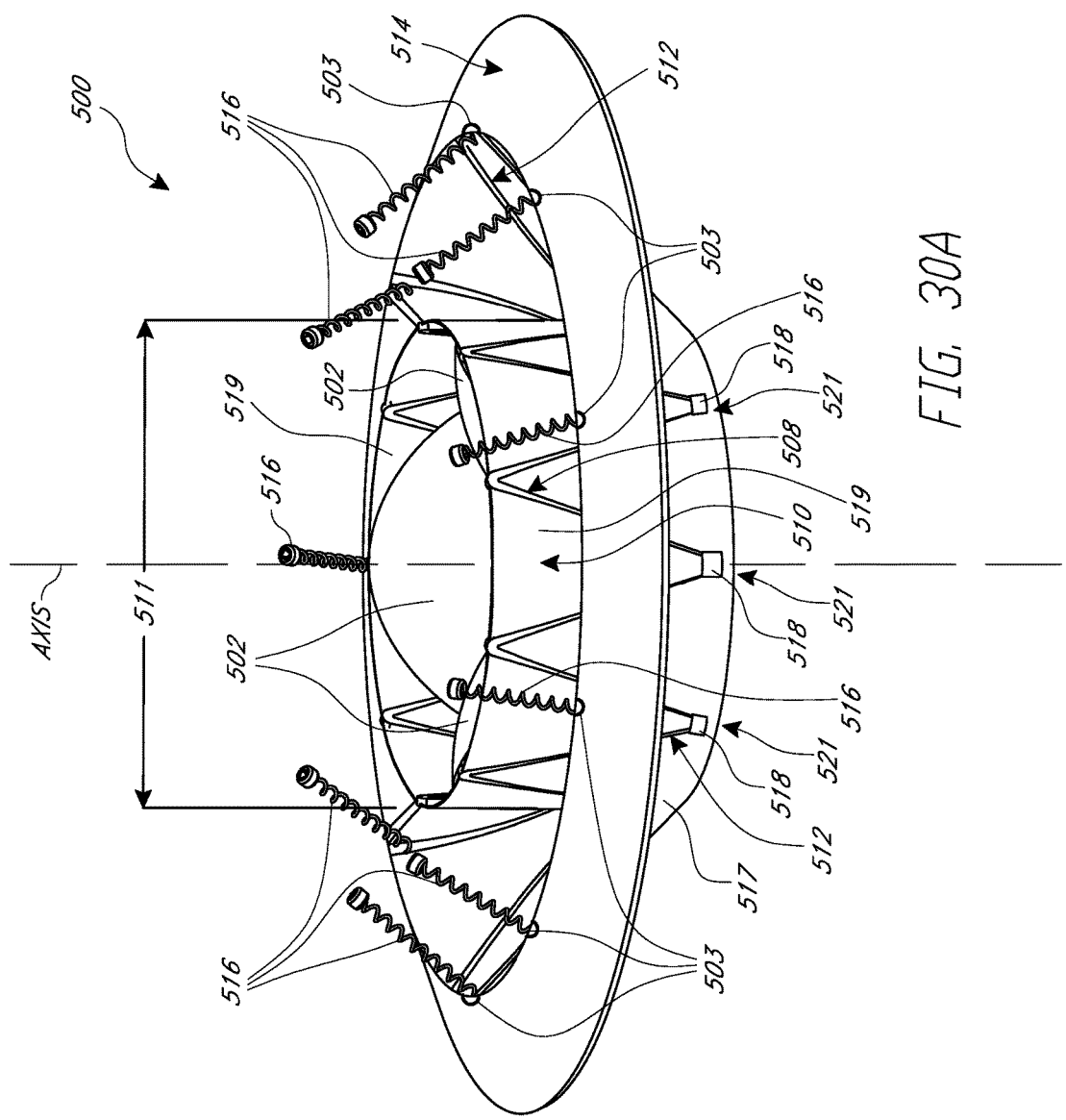

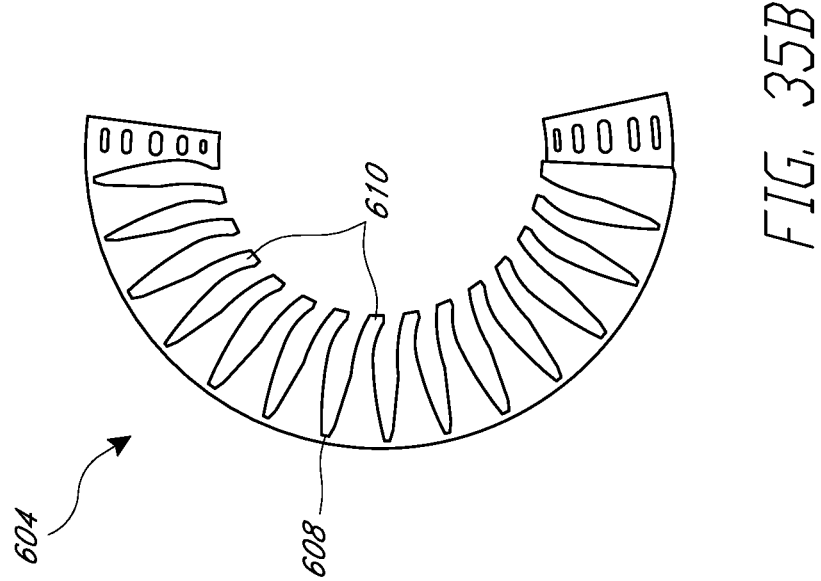

IMPLANTABLE DEVICE AND DELIVERY SYSTEM FOR RESHAPING A HEART VALVE ANNULUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims the benefit of priority under 35 U.S.C. § 119(e) of U.S. Provisional Application No. 62/256,660 entitled "MITRAL VALVE" and filed on Nov. 17, 2015, the entire disclosure of which is incorporated herein by reference for all purposes and forms a part of this specification.

BACKGROUND

Field

In general, features related to implantable medical devices are described. For example, heart valve medical devices and delivery and positioning systems for implanting various devices are described.

Description of the Related Art

Heart valve incompetency is a serious problem. For example, heart disease can cause the chambers of the heart to expand and weaken. With specific reference to the mitral valve, as a result of aging or disease, the left ventricle dilates and the papillary muscles are displaced. Consequently, the annulus of the mitral heart valve dilates excessively. In this state of dilation, valve leaflets no longer effectively close, or coapt, during systolic contraction. Consequently, regurgitation (i.e. retrograde flow back across the valve that should be closed) of blood occurs during ventricular contraction. Cardiac output is thus decreased.

This condition is typically addressed by the surgical implantation of an annuloplasty ring. A surgeon positions the annuloplasty ring proximate the valve annulus and sutures it in place thereby restoring the valve annulus to approximately its native configuration. The valve leaflets can now function normally again.

This procedure is invasive as it is performed open chest and is also time consuming. In open heart surgery, the patient is put on cardiopulmonary bypass with its associated risks of morbidity and mortality due to stroke, thrombosis, heart attack and extended recovery time.

There is, therefore, a need for less invasive and more efficient solutions to these problems that avoid the aforementioned drawbacks.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Systems, devices and methods for a heart valve implant and related delivery systems are described. The implant is intended to be delivered in a minimally invasive percutaneous manner, such as transfemorally, transeptally, or transapically. The implant may instead be implanted surgically, in that it should reduce the duration of the procedure and, more particularly, the duration that the patient is on bypass. The development can be directed to mitral valve or tricuspid valve procedures.

The development relates to the implant and delivery systems, and associated methods of use of each. The implant contracts to a first configuration, such as a delivery configuration, having a first diameter for delivery via a delivery catheter. The implant is capable of expanding out to a second configuration, such as a tissue engaging configuration (and/or anchored configuration), having a second diameter larger than the first diameter to match the width of a dilated annulus of a heart valve. The implant engages the tissue of the heart valve annulus and then contracts to a third configuration, such as an annulus remodeling diameter, having a third diameter that is smaller than the second diameter, thus gathering and cinching in the dilated annulus to decrease the width of the dilated annulus.

The implant includes a tubular frame with moveable struts, where pairs of adjacent struts form apices. The apices have collars at least partially surrounding the apex. After engaging heart valve annulus tissue with the implant, the collars can be moved along the apex, e.g. downward or upward along the apex, to decrease the angle between the adjacent struts, causing the tubular frame to contract in width. This pulls the tissue of the heart valve annulus closer together. The implant thus reconfigures the valve annulus down to a smaller diameter, reducing and/or eliminating problems associate with the valve, such as regurgitation.

A delivery system and associated methods are also disclosed that comprise a catheter and imaging and positioning features to maneuver the distal end of the catheter and the device into the desired position above and proximate the heart valve annulus. Transeptal delivery may be used, for example, with procedures involving the mitral valve. The delivery system can be used with the implant described herein as well as other implantable devices.

Moreover, the development also provides an artificial heart valve with a modified ring-like structure that not only provides for reduction of the heart valve annulus, but also displaces or replaces one or more defective heart valve leaflets. The artificial valve may include the various implant devices described herein having the one or more leaflets attached thereto.

In particular, in one aspect, an implant for reducing heart valve regurgitation is described. The implant comprises a frame, a plurality of anchoring members and a plurality of collars. The frame has upper crowns, lower crowns and struts between the upper and lower crowns. The frame has a tissue engaging configuration having a tissue engaging diameter, and an annulus remodeling configuration where the frame has an annulus remodeling diameter that is less than the tissue engaging diameter. The plurality of anchoring members are coupled with the lower crowns of the frame for engaging cardiac tissue proximate the heart valve annulus. The plurality of collars are coupled with the upper crowns of the frame, wherein when force is applied to the collars, the collars slide along the upper crowns and the struts to move the frame from the tissue engaging configuration towards the annulus remodeling configuration.

In some embodiments, the plurality of anchoring members are helically wound anchoring members and the lower crowns of the frame are adapted to threadingly receive the helically wound anchoring members. The helically wound anchoring members may further include anchoring heads for engagement with actuators to rotationally advance the helically wound anchoring members in the cardiac tissue to anchor the frame into the cardiac tissue. The implant may further comprise abutments on each of the anchor heads to engage with the struts and the lower crowns to limit travel of the helically wound anchoring members. The helically wound anchoring members may have sharpened tips to facilitate penetration of the helically wound anchor members into the cardiac tissue.

The implant may further comprise at least one tab on each of the collars, with the tabs inwardly biased to engage with the upper crowns when the collars are slid over the upper crowns and struts. The implant may further comprise a groove formed on an outwardly facing side of the upper crowns and at least one tab on each of the collars with the tabs inwardly biased to engage with the groove. Each of the collars may comprise a plurality of the tabs, and the plurality of tabs can be advanced over the upper crowns and struts to selectively vary the annulus remodeling diameter of the frame. The plurality of tabs may be vertically disposed on an outwardly facing portion of the collars and comprise a lowermost tab, with the lowermost tab initially disposed and engaged with an underside of the upper crown.

The implant may further comprise a plurality of pusher members that engage with the plurality of collars to forcibly advance the collars over the upper crowns and struts to reduce the diameter of the frame.

The implant may further comprise flex sections on the collars to facilitate advancement of the collars over the upper crowns and struts.

The frame may define a longitudinal axis, and the lower crowns and anchoring members received in the lower crowns may be inclined outwardly in a distal direction at an angle between about 30° to about 60° with respect to a portion of the axis that extends distally below the implant.

In another aspect, a delivery system for delivering an implant for reducing heart valve regurgitation is described. The delivery system comprises the implant, a delivery catheter, and an imaging catheter. The implant comprises a frame, a plurality of anchoring members and a plurality of collars. The frame has upper crowns, lower crowns and struts between the upper and lower crowns, and a tissue engaging configuration with a tissue engaging diameter and an annulus remodeling configuration where the frame has an annulus remodeling diameter less than the tissue engaging diameter. The plurality of anchoring members are coupled with the lower crowns of the frame for engaging cardiac tissue proximate the heart valve annulus. The plurality of collars are coupled with the upper crowns of the frame, and when force is applied to the collars, the collars slide on the upper crowns and the struts to move the frame from the tissue engaging configuration towards the annulus remodeling configuration. The delivery catheter is releasably attached to the implant and is configured to deliver the implant to a position proximate the heart valve annulus. The imaging catheter comprises a distal end configured to extend proximate the heart valve annulus and to capture one or more images therein of the position of the implant relative to the heart valve annulus.

In some embodiments, the delivery system further comprises a plurality of actuating members for engaging corresponding anchoring members of the implant to cause the anchoring members to penetrate and advance into the cardiac tissue to anchor the frame in position proximate the heart valve annulus. The delivery system may further comprise a plurality of pusher members for engaging corresponding collars of the implant to forcibly advance each collar over its respective upper crown and struts thereby reducing the diameter of the frame and the valve annulus. The delivery system may further comprise means for centering the imaging catheter with respect to the implant. The distal end of the imaging catheter may comprise longitudinally disposed and circumferentially disposed ultrasound transducers. The frame may define a longitudinal axis, and the lower crowns and anchoring members received in the lower crowns may be inclined outwardly in a distal direction at an angle of approximately 45° with respect to a portion of the axis that extends distally below the implant.

In some embodiments, the delivery system may further comprise a loop encircling the frame proximate its lower crowns, and a constricting actuator to constrict the loop to facilitate collapse and loading of the implant into the delivery system. Each of the collars may comprise a plurality of tabs that are inwardly biased to engage with corresponding undersides of the upper crowns when the collars are slid over the upper crowns and struts by the pusher members. After the frame has been anchored into the cardiac tissue, the loop may be constricted to determine the desired reduction in diameter of the frame prior to advancing the collars and tabs over the respective upper crowns and struts.

In another aspect, a method of reducing the size of an enlarged heart valve annulus is described. The method comprises the steps of delivering an implant in a delivery system to a site above and proximate the enlarged heart valve annulus, the implant having a proximal end and a distal end; releasing the implant from the delivery system to allow the implant to take on a tissue engaging diameter; anchoring the distal end of the implant into cardiac tissue proximate and above the enlarged heart valve annulus; translating a plurality of collars over corresponding upper crowns of the proximal end of the implant to reduce the tissue engaging diameter to an annulus remodeling diameter, thereby reducing the size of the enlarged heart valve annulus; and disengaging the anchored and reduced diameter implant from the delivery system.

In another aspect, a heart valve replacement implant is described. The heart valve replacement implant comprises a replacement valve, a tubular valve housing, a cinch frame, a plurality of anchoring members and a plurality of collars. The replacement valve has a plurality of replacement valve leaflets. The tubular valve housing is fixedly attached to the replacement valve leaflets. The cinch frame is connected to and circumferentially surrounds the tubular valve housing. The cinch frame has upper crowns, lower crowns and struts between the upper and lower crowns, and is configurable between a tissue engaging configuration with opposing upper crowns separated by a tissue engaging diameter and an annulus remodeling configuration with opposing upper crowns separated by an annulus remodeling diameter that is less than the tissue engaging diameter. The plurality of anchoring members are coupled with the upper crowns of the cinch frame for engaging cardiac tissue proximate the heart valve annulus. The plurality of collars are coupled with the lower crowns of the cinch frame. When force is applied to the collars, the collars slide on the lower crowns and the struts to reconfigure the cinch frame from the tissue engaging configuration towards the annulus remodeling configuration.

In some embodiments, the heart valve replacement implant further comprises a sealing flange on the cinch frame that is disposed on the atrial side of the heart valve when the heart valve replacement system is implanted.

In another aspect, a heart valve replacement implant is described. The heart valve replacement implant comprises a replacement valve, a tubular valve, a cinch frame, a plurality of anchoring members and a plurality of collars. The replacement valve has a plurality of replacement valve leaflets. The tubular valve housing is fixedly attached to the replacement valve leaflets. The cinch frame is connected to and circumferentially surrounds the tubular valve housing. The cinch frame has upper crowns, lower crowns and struts between the upper and lower crowns, and is configurable between a tissue engaging configuration with opposing lower crowns separated by a tissue engaging diameter and an annulus remodeling configuration with opposing lower crowns separated by an annulus remodeling diameter that is less than the tissue engaging diameter. The plurality of anchoring members are coupled with the lower crowns of the cinch frame for engaging cardiac tissue proximate the heart valve annulus. The plurality of collars are coupled with the upper crowns of the cinch frame. When force is applied to the collars, the collars slide on the upper crowns and the struts to reconfigure the cinch frame from the tissue engaging configuration towards the annulus remodeling configuration.

In some embodiments, the tubular valve housing has a proximal end and a distal end, and the upper crowns of the cinch frame have extensions adapted to be received in openings in the proximal end of the valve housing such that the upper crowns and the cinch frame pivot about the proximal end of the valve housing.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 5A-5E are various views of embodiments of a collar and frame that may be used with the implant of FIG. 1.

FIGS. 14 and 15 are perspective views of an embodiment of an implant having collars with locking tabs shown, respectively, in an expanded and a cinched state.

FIGS. 16 and 17 are partial side views of an embodiment of an implant having a rotational member and filament for cinching adjacent struts of the implant.

FIGS. 18 and 19 are partial side views of an embodiment of an implant having two strings for cinching adjacent struts of the implant.

FIG. 20 is a partial side of an embodiment of an implant having an axially displaceable circumferential filament for cinching the frame of the implant.

FIGS. 22A through 22E are perspective views of various embodiments of delivery systems having positioning and imaging capabilities that may be used to deliver the various implants described herein.

FIGS. 24A through 24D are perspective views of another embodiment of an ICE catheter and delivery system for delivering, e.g. aligning and positioning, the various implants described herein and having a circular array of sensors at the tip of the catheter, e.g. for radial and/or circumferential echo views.

FIGS. 30A through 30C are perspective views of a replacement heart valve implant with anchors coupled to upper crowns and collars coupled with lower crowns and having a sealing atrial flange and shown, respectively, in a unconstrained state, an anchored state, and a cinched state.

FIGS. 35A and 35B are side views of an embodiment of a distal section of a steerable catheter having a spine that may be used to deliver the various implants described herein.

DETAILED DESCRIPTION

Figure 1:
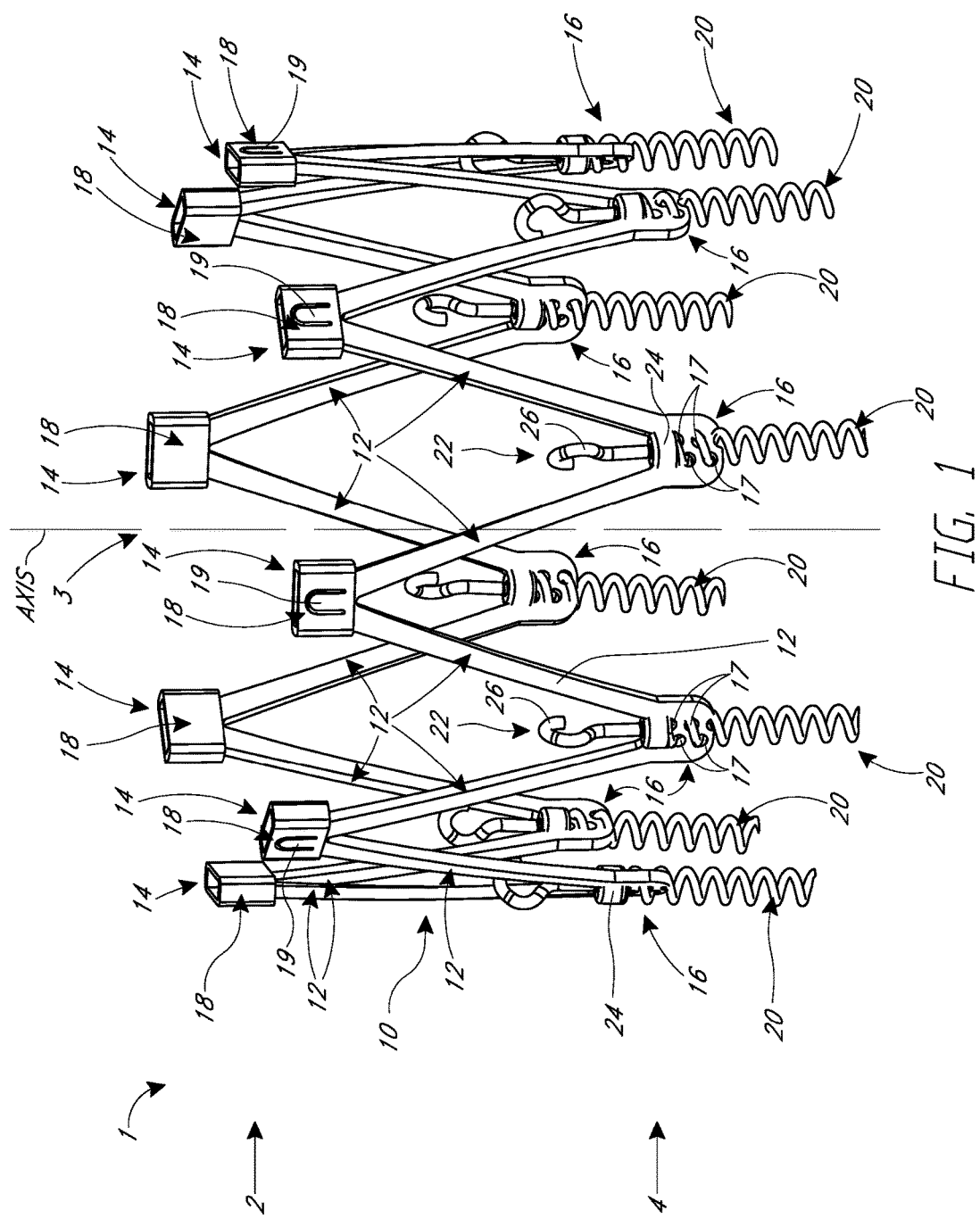
FIG. 1 is a perspective view of an embodiment of an implant, having a frame, collars and anchors, for reshaping a heart valve annulus.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

FIGS. 1 through 4 are perspective views of an embodiment of an implant 1. The implant 1 is intended to be delivered proximate to, above and/or or within, the cardiac valve annulus. Unless otherwise stated, "valve" as used herein may refer to any of a variety of valves, including the tricuspid or mitral valve of the heart. The implant 1 may be subsequently implanted in the annular cardiac tissue just above the plane of the valve orifice. In some embodiments, the implant may be a heart valve replacement including valve leaflets, which can be implanted in annular cardiac tissue and extend into the valve annulus, as further described herein.

Particular features for various embodiments of an implant, of a delivery system, and of related systems and methods of use of the implant and delivery system (either together or separately), are described herein. The implant, delivery system, and related systems and methods of use may have the same or similar features and/or functionalities as other implants, delivery systems, and related systems and methods of use as described, for example, in U.S. patent application Ser. No. 14/861,877 entitled "ADJUSTABLE ENDOLUMENAL IMPLANT FOR RESHAPING MITRAL VALVE ANNULUS"and filed on Sep. 22, 2015, as described, for example, in U.S. Provisional Application No. 62/234,592 entitled "HEART VALVE DELIVERY SYSTEM WITH INTRAVASCULAR ULTRASOUND IMAGING CAPABILITY" and filed on Sep. 29, 2015, and/or as described, for example, in U.S. patent application Ser. No. 15/280,004 entitled "METHODS FOR DELIVERY OF HEART VALVE DEVICES USING INTRAVASCULAR ULTRASOUND IMAGING" and filed on Sep. 29, 2016, the entire disclosure of each of which is incorporated herein by reference for all purposes and forms a part of this specification. Thus, the description of particular features and functionalities herein is not meant to exclude other features and functionalities, such as those described in the references incorporated herein by reference or others within the scope of the development.

With reference to FIG. 1, the implant 1 is an implantable device. The implant 1 forms an opening 3 extending through the implant 1. For sake of description, a geometric reference longitudinal axis is indicated. The implant 1 may be described with reference to the axis. An "axial" direction refers to movement generally parallel to the axis in either an upward or downward direction, unless otherwise indicated. The opening 3 extends axially between an upper portion 2 of the implant 1 and a lower portion 4 of the implant 1. The upper and lower portions 2, 4 may include various features of the implant 1. The terms "upper," "upward," and the like refer to directions generally toward the upper portion 2, and the terms "lower," "downward," and the like refer to directions generally toward the lower portion 4, unless otherwise indicated. "Proximal" refers to a direction in the upward direction, and "distal" refers to a direction in the downward direction. The terms "inner," "inward," and the like refer to directions generally toward the axis, and terms "outer," "outward," and the like refer to directions generally away from the axis, unless otherwise indicated.

The implant 1 includes a frame 10. The frame 10 extends around and partially along the axis. The axis may be defined by the frame 10. The frame 10 is generally symmetric with respect to the axis. However, the frame 10 need not be symmetric with respect to the axis. The frame 10 has a generally tubular shape. "Tubular" includes circular as well as other rounded or otherwise closed shapes. The frame 10 is generally circular about the axis. The frame 10 may be circular, rounded, ellipsoidal, segmented, other shapes, or combinations thereof. The frame 10 may change shape, size, configuration, etc. The frame 10 may have various shapes, sizes, configurations etc. at various phases of use, e.g. pre-delivery, during delivery, after engagement with tissue, after contracting the annulus, post-contraction, during the lifetime of use while implanted, etc.

The implant 1 includes one or more struts 12. The struts 12 are part of the frame 10. The struts 12 are elongated structural members. The struts 12 and/or other parts of the frame 10 are formed of a metal alloy. The struts 12 and/or other parts of the frame 10 may be formed of an alloy of nickel titanium. In some embodiments, the struts 12 and/or other parts of the frame 10 are formed of other metals, metal alloys, plastics, polymers, composites, other suitable materials, or combinations thereof. There are sixteen struts 12. In some embodiments, there may be fewer or more than sixteen struts 12. In some embodiments, there may be at least two, four, six, eight, ten, twelve, fourteen, eighteen, twenty, twenty-two, twenty-four, twenty-six, twenty-eight, thirty, or more struts 12.

The struts 12 may be part of the same, monolithic piece of material (e.g. tube stock). Thus the struts 12 may refer to different portions of the same, extensive component. The struts 12 may be formed from the same piece of material. The struts 12 may be formed separately and attached permanently together, e.g. by welding, etc. In some embodiments, the struts 12 may be separate components that are detachably coupled together by other components of the implant 1. For example, the struts 12 may be held together via various components described herein, such as collars 18, anchors 20, other features, or combinations thereof. In some embodiments, separate strut units may include two or more struts permanently attached together such as at an apex, and the separate units may each be coupled together, either permanently or detachably, to form the frame 10. In some embodiments, the struts 12 may be attached by hinges, pins, or other suitable means.

The elongated, middle portions of the struts 12 have a generally rectangular cross-section but can vary in circumferential width and radial thickness to allow for different beam characteristics and forces applied as the collars are advanced. The long ends of the rectangular cross-section of the struts 12 extend along the circumference of the frame 10. "Circumference" as used herein generally refers to a perimeter or boundary and can refer to a circular or other rounded or non-rounded path lying in a plane substantially transverse to the axis, unless otherwise stated. The short ends of the rectangular cross-section of the struts 12 extend transversely to the circumference of the frame 10. In some embodiments, other configurations and/or cross-sectional shapes of the struts 12 may be implemented.

The struts 12 extend around the axis to form the various shapes of the frame 10. The struts 12 are arranged such that the wall pattern of the frame 10 may be approximately sinusoidally or zig-zag shaped. In some embodiments, the wall pattern may have other suitable shapes, sinusoidal or otherwise. The vertices of the sinusoidal shaped frame 10 may be pointed or rounded.

Pairs of adjacent struts 12 meet at an apex. At least a first pair of adjacent struts 12 meets at an upper apex or crown 14 at the upper portion 2 of the implant 1. At least a second pair of adjacent struts 12 meets at a lower apex or crown 16 at the lower portion 4 of the implant 1. The terms "apex," apices," and the like may be used interchangeably with terms "crown," "crowns," and the like, as used herein and as used in any reference incorporated by reference herein, unless otherwise stated. The upper and lower crowns 14, 16 are spaced sequentially along the circumference of the frame 10, with one of the upper crowns 14 followed by one of the lower crowns 16, followed by another one of the upper crowns 14, etc. In the illustrated embodiment, there are eight upper crowns 14 and eight lower crowns 16. In some embodiments, there may be no more than about six or four or fewer or more than eight or ten or twelve upper and lower crowns 14, 16, depending on the number of struts 12 and the resulting number of apices.

The upper crowns 14 are each configured to have a restraint such as a collar 18 fitted over and/or around the upper crown 14. Thus, the upper crowns 14 may include various features, dimensions, etc. as described herein for coupling with the collar 18, as further described. The upper crowns 14 are shown partially covered by the collars 18 in FIG. 1. The upper ends of the upper crowns 14 are more clearly seen in FIG. 4, where the collars 18 have been moved distally toward the lower portion 4 of the implant 1 relative to their position in FIG. 1. In some embodiments, one or more of the upper crowns 14 may not have the collar 18. In some embodiments, fewer than all of the upper crowns 14 are configured to receive the collar 18. In some embodiments, all of the upper crowns 14 may be configured to receive the collar 18 but when implanted only some of the upper crowns 14 may actually include the collar 18.

At least two and optimally at least four or six or all of the lower crowns 16 are configured for coupling with an anchor 20. The anchor 20 is moveably coupled with the lower crown 16. The anchor 20 engages with tissue of the heart, for example the annulus, to secure the implant 1 to the tissue, as further described herein. Movement of the anchor 20 relative to the lower crowns 16 causes the anchor 20 to penetrate the tissue. The lower crowns 16 may include a variety of engagement features to allow such movement of the anchors 20, such as flanges and/or the openings 17. The lower crowns 16 each include a series of the openings 17 extending through the lower crowns 16. The openings 17 extend in two spaced columns in the axial direction along the lower crown 16. The openings 17 in each column are alternately located in the axial direction, as shown, to accommodate receipt of the anchor 20 therein. Other configurations and/or spacings of the openings 17 may be implemented. For clarity, only some of the openings 17 are labeled in FIG. 1. The openings 17 are shown as circular holes. Other shaped openings 17 may be implemented.

The openings 17 of the lower crown 16 are configured to rotatably receive a helical segment of the corresponding anchor 20 such that the anchor extends sequentially through the openings 17, both while the anchor 20 moves relative to the struts 12 and while the anchor 20 is stationary relative to the struts 12, as further described herein. In some embodiments, features alternative to or in addition to the openings 17 may be used to couple the anchor 20 with the corresponding lower crown 16. In some embodiments, fewer than all of the lower crowns 16 may be configured for coupling with the anchor 20. Thus one or more of the lower crowns 16 may not have the openings 17 and/or other features for coupling with the anchor 20. In some embodiments, all of the lower crowns 16 may be configured for coupling with the anchor 20, but when implanted only some of the lower crowns 16 may actually include the anchor 20.

The struts 12 are reconfigurable about the upper and lower crowns 14, 16. Pairs of adjacent struts 12 that meet at the upper and lower crowns 14, 16 can move angularly relative to each other. Such movement may be described as a rotation or pivot of the adjacent struts 12 about the corresponding upper or lower crown 14, 16. For example, two adjacent struts 12 forming the upper crown 14 may be moved such that the struts 12 effectively rotate relative to each other about the upper crown 14. For example, two adjacent struts 12 forming the lower crown 16 may be moved such that the struts 12 effectively rotate relative to each other about the lower crown 16. "Rotation" of the struts 12 as described includes pinching together of the struts 12, for example with the collar 18 as described herein. Thus, adjacent struts 12 may not include an actual rotatable hinge, pin, or other rotation features. Movement of the struts 12 closer together to decrease the angle therebetween is described as a "closing" of the struts 12. Movement of the struts 12 farther apart to increase the angle therebetween is described as an "opening" of the struts 12.

The struts 12 may be biased to an enlarged cross-sectional configuration in the absence of an external force applied to the struts 12. Application of an external circumferentially compressive force to the struts 12, for example with the collar 18, causes the struts 12 to move angularly, for example to close. Movement of the struts 12 in this closing manner also causes the implant 1 to decrease its circumference (e.g. diameter) in the case of a circular implant 1. In its free, unconstrained state, the frame 10 may be in an enlarged configuration. Application of the compressive circumferential force causes the circumference of the frame 10 to reduce. Removal or lessening of the circumferential force allows the frame 10 to open. The circumferential force may be increased or decreased by moving the collar 18 farther downward or upward, respectively, in the axial direction, as further described herein. The collar 18 may lock in place after translating axially down the upper crown 14 to secure the implant 1 at a particular width.

The implant 1 includes one or more restraints such as the sliders or collars 18. The terms "collar," collars," and the like may be used interchangeably with the terms "slider," "sliders," "sliding members," and the like, as used herein and as used in any reference incorporated by reference herein, unless otherwise stated. As shown in FIGS. 1-4, the implant 1 includes eight collars 18. In some embodiments, there may be fewer or more than eight collars 18. The number of collars 18 may correspond to the number of upper crowns 14. In some embodiments, there may be fewer collars 18 than upper crowns 14. Thus, in some embodiments, some upper crowns 14 of the frame 10 may not include the collar 18.

The collar 18 couples with the corresponding upper crown 14. The collar 18 may be fitted over the upper crown 14. The collar 18 forms an inner opening at least partially therethrough and into which the upper crown 14 is received as the collar 18 fits over the upper crown 14. The collar 18 may have a rectangular profile as shown. In some embodiments, the collar 18 may have other profiles, e.g. rounded, segmented, polygonal, other suitable shapes, or combinations thereof. The profile of the collar 18 may be a closed shape, as shown, or it may be an open shape such as a "C" shape. The collar 18 thus at least partially surrounds the corresponding upper crown 14. As shown, the collar 18 completely surrounds the corresponding upper crown 14. In some embodiments the collar 18 may not completely surround the upper crown 14. The collar 18 engages with the upper crown 14.

The collar 18 may engage with circumferentially opposed sides of the upper crown 14 and/or adjacent struts 12. The collar 18 engages with and may be advanced downward over the upper crown 14 to angularly move the corresponding pair of adjacent struts 12 towards each other. The collar 18 may apply a compressive circumferential force to the struts 12 to cause the struts 12 to decrease the angle between the struts 12. The circumferential force may be applied inwardly to the struts 12 and towards the upper crown 14. Thus, a vertical force applied to the collars 18 may be translated into a circumferential force on the struts 12. By "circumferential" it is meant that the direction of the forces is along the outer perimeter or boundary of the frame 10 as viewed from the top or bottom of the frame 10, and is not meant to limit the shape of the frame 10 to a circle. Movement of the collar 18 over the struts 12 moves, e.g. rotates, the struts 12 such that the angle between the adjacent struts 12 decreases. A first circumferential force may be applied to one of the struts 12 by the collar 18 and a second circumferential force that is opposite in direction to the first circumferential force may be applied to the adjacent strut 12 by that same collar 18. The farther the collar 18 is moved down over the struts 12, the more the struts 12 move and the more the angle decreases, causing the frame 10 to decrease in width, e.g. diameter. The struts 12 thus move relative to each other about the upper crown 14 due to movement of the collar 18. The collar 18 may lock in place, for example with a locking tab 19.

The collar 18 may include the locking tab 19. The locking tab 19 provides an engagement feature for the collar 18 to engage with the struts 12. The locking tab 19 locks the collar 18 in place on the upper crown 14 after movement of the collar 18 over the upper crown 14. The locking tab 19 is biased toward the inner opening formed by the collar 18. The locking tab 19 may be shape set to take on an inwardly oriented bias. The collar 18 and/or features thereof such as the locking tab 19 are formed of a nickel titanium alloy such as Nitinol. In some embodiments, the collar 18 and/or features thereof such as the locking tab 19 are formed of other materials, such as metals, other metal alloys, plastics, polymers, composites, other suitable materials, or combinations thereof. Further details of various embodiments of the collar 18, and features thereof such as the locking tab 19, are described herein.

The collars 18 may thus provide one or more functions for the implant 1. In some embodiments, the collars 18 may cinch the frame 10, as described. In some embodiments, the frame 10 may be cinched by features in addition to or alternatively to the collars 18, and the collars 18 may restrain the frame 10 in the cinched state. In some embodiments, the collars 18 may thus not cinch the frame 10 but only restrain the frame 10 in the cinched state. In some embodiments, the collars 18 may cinch the frame 10 as well as restrain the frame 10 in the cinched state.

The implant 1 includes one or more anchors 20. Referring to FIG. 1, the anchors 20 have anchor heads 22 attached at their upper or proximal ends. As shown, each anchor head 22 comprises an abutment 24 and an engagement structure such as a hook 26. The abutment 24 may be a cap portion on an upper end of the anchor 20. The abutment may be cylindrical. The abutment 24 may have a width sized to limit axial advance of the anchor 20, as described herein. The hooks 26 are elongated, over-hanging members. The hooks 26 may provide an engagement for a delivery tool. The hooks 26 may interact with a delivery tool to rotate and axially advance the anchors 20, as described herein. In some embodiments, features other than the hooks 26 may be used, for example eye bolts.

The anchors 20 are made of a suitable biocompatible metal alloy such as stainless steel, cobalt chromium, platinum iridium, nickel titanium, other suitable materials, or combinations thereof. Each anchor 20 is sharpened at its distal point, or leading turn, so as to facilitate penetration into the cardiac tissue. Each anchor 20 may be from about ten to about fifteen millimeters (mm) in total axial length. In some embodiments, the anchors 20 may be shorter or longer than ten to fifteen millimeters (mm) in total axial length. By "total" axial length it is meant the axial length of the anchor 20 from the end of the distal penetrating tip to the opposite, proximal end of the head 22. The helical portion of the anchor 20 may be from about six to about twelve millimeters (mm) in axial length, i.e. in an axial direction. In some embodiments, the helical portion of the anchor 20 may be shorter or longer than six to twelve millimeters (mm) in axial length. The anchor head 22 and/or other non-helical portions of the anchor 20 may be from about three to about four millimeters (mm) in axial length. In some embodiments, the anchor head 22 and/or other non-helical portions may be shorter or longer than three to four millimeters (mm) in axial length. The anchors 20 are capable of extending from about four to about seven millimeters (mm) axially beyond the corresponding lower crown 16. For example, the helical portions of the anchors 20 may extend from four to seven millimeters (mm) into the cardiac tissue. As mentioned, the frame 10 is shown with eight upper crowns 14 and eight lower crowns 16 and anchors 20, but this number of apices is shown for illustration purposes and may be varied, for example four upper and lower apices, sixteen upper and lower apices, etc. In some embodiments, regardless of the number of apices, each upper crown 14 is fitted with a collar 18 and each lower crown 16 has a respective anchor 20 threadingly received through the openings 17 of the anchor 20.

The anchors 20 couple with the lower crowns 16. The anchors 20 may be in the general shape of a helix. As shown, the openings 17 receive helically wound anchors 20. The openings 17 are spaced to accommodate the pitch of the helical anchors 20, for example the spacing between the turns in the helix of the anchor 20. There may be a gap between the inner diameter of the openings 17 and the outer diameter of the anchor 20 to allow for free movement of the anchor 20 through the openings 17. There may be a small gap between the inner diameter of the openings 17 and the outer diameter of the anchor 20. In some embodiments, there may be an interference fit between the openings 17 and the anchor 20 or a varying pitch to provide interference between the anchor and frame.

Figure 2:
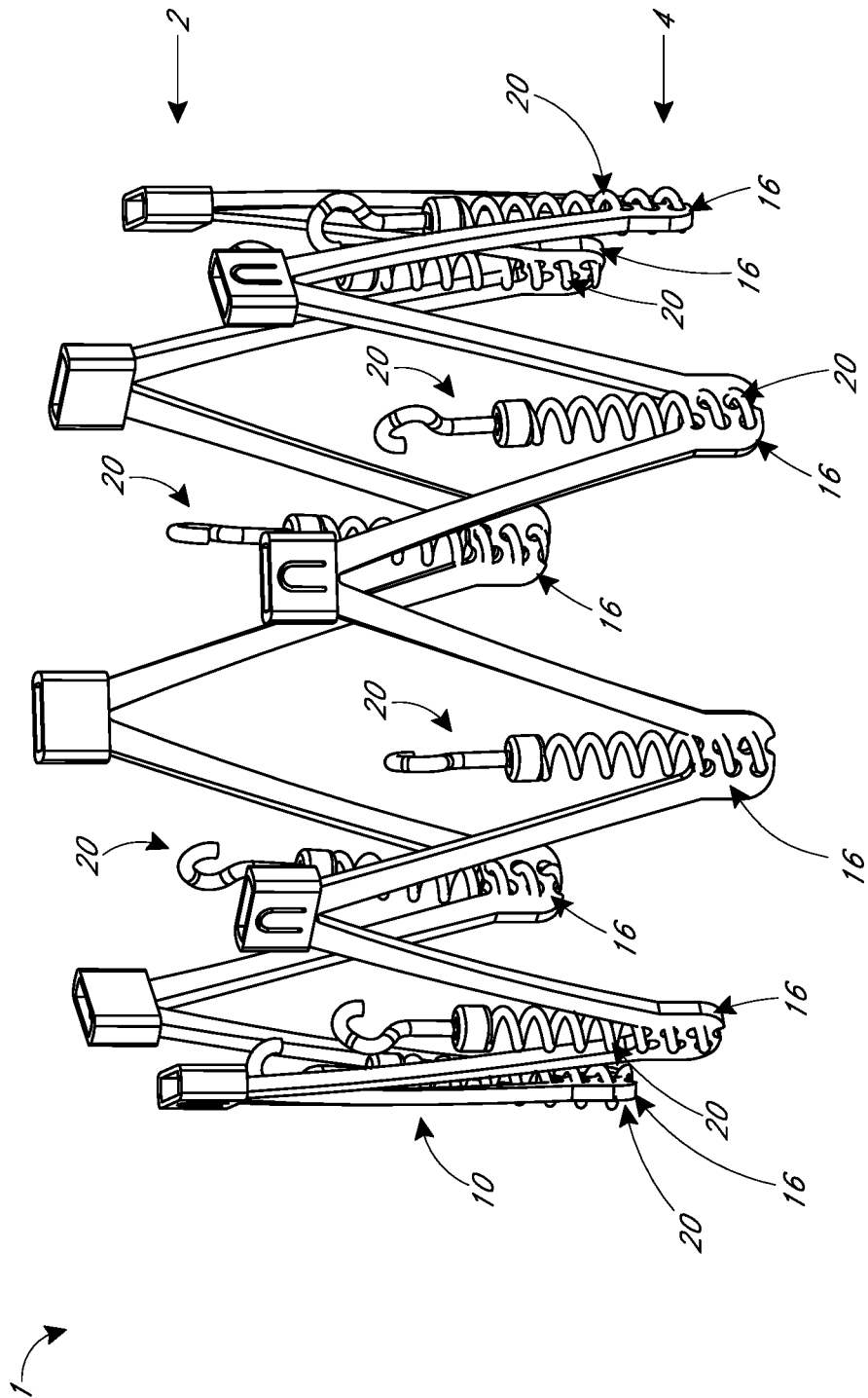
FIG. 2 is a perspective view of the implant of FIG. 1 shown in an unconstrained state.
Figure 3:
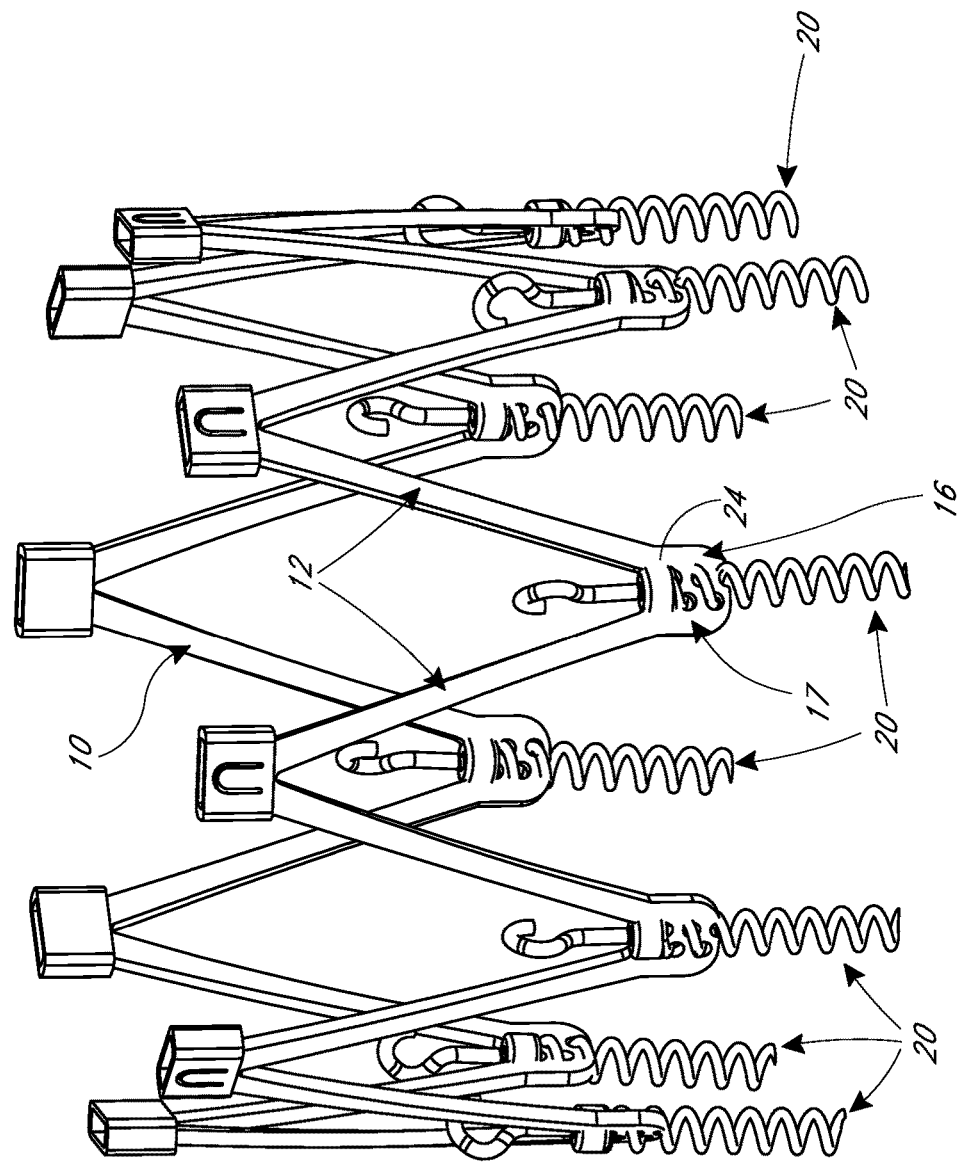
FIG. 3 is a perspective view of the implant of FIG. 1 shown in an anchored state.
Figure 4:
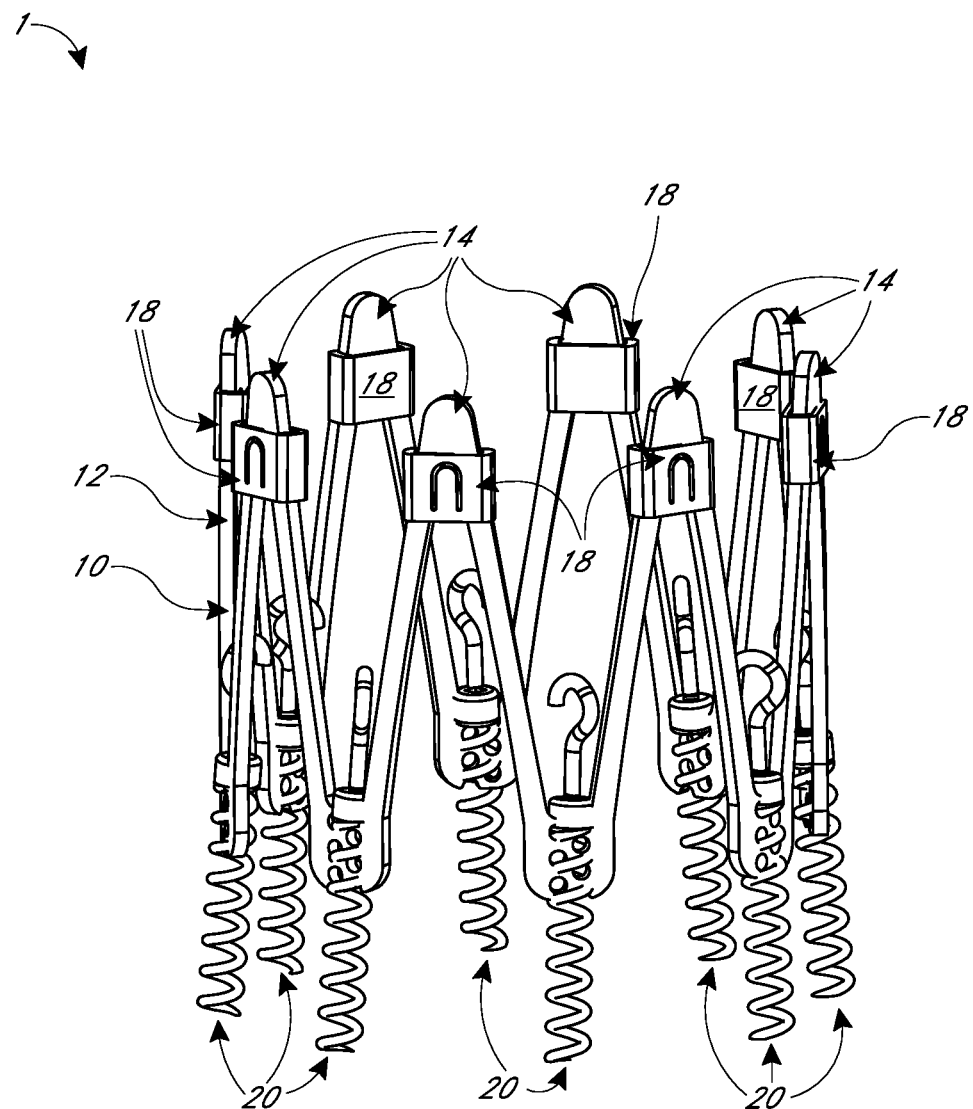
FIG. 4 is a perspective view of the implant of FIG. 1 shown in a cinched state.

FIGS. 2 through 4 illustrate the implant 1 in various stages of delivery and deployment. In FIG. 2, the implant has been expelled from a delivery catheter and is in its unconstrained state above and proximate the cardiac valve annulus. This unconstrained state may be a tissue engaging configuration of the implant 1 having a tissue engaging diameter and a tissue engaging height. In this unconstrained state, the frame 10 may have an overall axial height in the range of 15 to 20 millimeters (mm). This height or range of height will vary even further from this 15 to 20 mm range, depending on the number of apices and anchors 20. More specifically, the height is smaller with more apices and anchors 20 and is greater with fewer apices and anchors 20. In the embodiment shown in FIG. 2, the frame has a height of approximately 17 millimeters. Other heights in the unconstrained state are possible, and this particular embodiment is not limiting of the scope of the present disclosure.

FIG. 3 depicts the implant after it has been anchored into the cardiac tissue. This anchored state may be an anchored configuration, which may or may not be similar to the tissue engaging configuration, of the implant 1 having an anchored diameter and an anchored height. The anchored diameter of the implant 1 may be less than, equal to, or greater than the tissue engaging diameter of the implant 1 in the tissue engaging configuration. The anchored height of the implant 1 may be less than, equal to, or greater than the tissue engaging height of the implant 1 in the first configuration. Thus, the implant 1 when engaged with and anchored into the tissue may be in the tissue engaging configuration. The anchors 20 have been rotationally advanced through the lower crowns 16 and the tissue piercing end has rotationally advanced into the cardiac tissue. The abutments 24 function as a depth control for the anchors 20, limiting the extent of axial travel of the helical anchors 20 into the cardiac tissue as the abutments 24 seat in the valley bounded by the lower ends of the adjacent struts 12.

FIG. 4 shows the implant 1 in its contracted or cinched state. This cinched state may be an annulus remodeling configuration of the implant 1 having an annulus remodeling diameter and an annulus remodeling height. The annulus remodeling diameter of the implant 1 is less than the tissue engaging diameter of the implant 1 in the tissue engaging configuration. The annulus remodeling height of the implant 1 may be greater than the tissue engaging height of the implant 1 in the tissue engaging configuration. In the cinched state, the collars 18 have been moved downwardly over the upper crowns 14 until inwardly biased locking tabs 19 engage with the gap or valley bounded by the upper portions of adjacent struts 12, below the underside of the upper crowns 14. This engagement of the locking tabs 19 to the valley under the upper crowns 14 locks the implant into its cinched position. In an alternate embodiment, cut-outs may be formed on the upper crowns 14 to accept the locking tabs 19.

The implant 1 in it cinched state has a reduced circumference. Thus the cinched implant 1 has a reduced length perimeter or boundary relative to the unconstrained state. The reduction in circumference need not result in the same general shape of the implant as before the cinching. For example, before cinching, the implant 1 may be in a generally elliptical, oval or other shape, and after cinching the implant 1 may be in a general "D" shape or other shape (and with a relatively reduced circumference). Thus, the implant 1 may be in a variety of shapes before or after cinching, as well as during cinching. For instance, restraints such as the collars 18 may be advanced individually, i.e. not simultaneously. The implant 1 may thus have an irregular shape while being cinched. In some embodiments, even in the cinched state not all of the collars 18 are advanced, and/or are not all advanced the same amount, such that in the cinched state the angular displacements among different pairs of adjacent struts may not be the same. The implant 1 may thus be cinched in a custom manner depending on the particular patient's needs. In some embodiments, about half of the implant 1 may be cinched, for example to bring the anterior native leaflet closer to the posterior native leaflet, or vice versa. Thus, the "cinched" state of the implant 1 is not limited to only those particular shapes shown and described herein, but includes a multitude of possible shapes, sizes, etc. and which may be chosen based on needs of the patient.

Figure 5D:
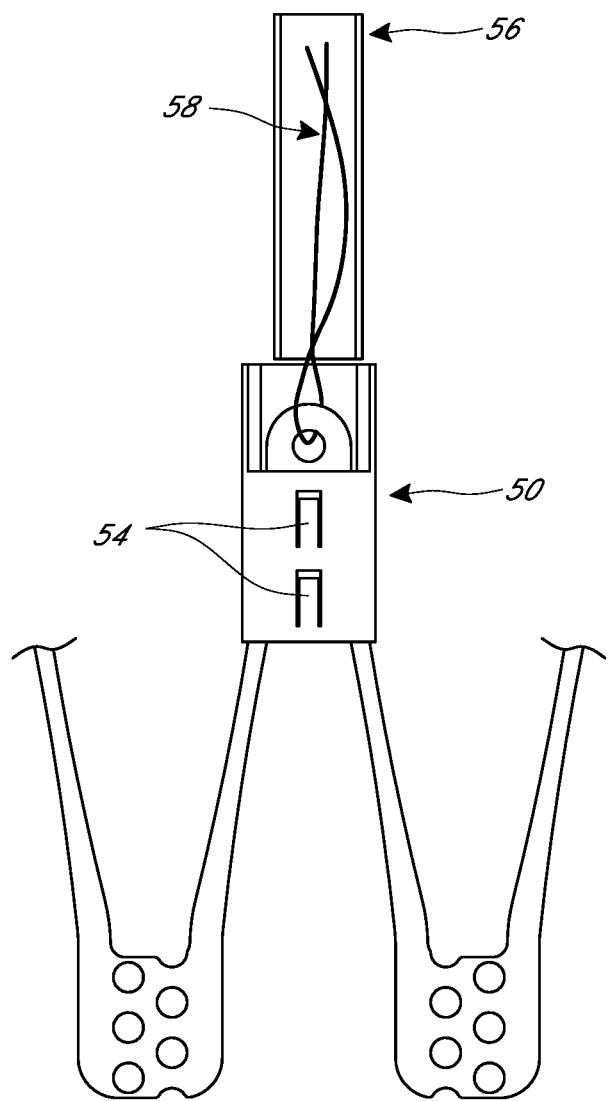

FIGS. 5A through 5D are various views of an embodiment of a collar 50 that may be used with the implant 1. The collar 50 is shown coupled with the struts 12 at the upper crown 14. FIGS. 5A and 5B are front views of a portion of the implant 1, showing the collar 50 coupled with the upper crown 14 at different axial locations. FIG. 5A shows the implant 1 in a unconstrained state. FIG. 5B shows the collar 50 advanced distally relative to the position of the collar 50 shown in FIG. 5A to reconfigure the implant 1 in a cinched state. FIG. 5C is a cross section view of the implant 1 taken along line 5C-5C of FIG. 5B. FIG. 5D is a front view of the implant 1 showing a portion of a delivery tool engaging the implant 1.

The collar 50 has multiple locking tabs 54. The locking tabs 54 may have the same or similar features and/or functionalities as other locking tabs described herein, for example the locking tabs 19, and vice versa. The locking tabs 54 may be projections or cutouts of the collar 50. The locking tabs 54 are biased toward the upper crown 14. The locking tabs 54 may therefore contact the upper crown 14. The upper crown 14 may include openings which can receive the ends of the locking tabs 54 therein. The upper crown 14 may define a gap in between adjacent struts 12 at a valley, as described, which may receive the end of the locking tabs 54 therein. While two such locking tabs 54 are shown, it should be understood that three or more locking tabs 54 could be employed. The plurality of locking tabs 54 allows the physician/user of the implant 1 to adjust the degree of cinch of the implant 1. Increased cinch, resulting in a smaller width of the implant 1 due to contraction, will tend to further reduce the width of the heart valve annulus.

FIGS. 5B and 5C depict the collar 50 advanced distally. The collar 50 as shown may be in its fully advanced state, thus reconfiguring the implant 1 to a state of maximum cinch. The uppermost locking tab 54 is engaging the underside of the upper crown 14. As stated with reference to FIGS. 1-4, rather than engaging the underside or upper crown 14, cut-outs in the upper crown 14 itself can provide the locking engagement with tabs 54. Additionally, as best seen in FIG. 5D, the collar 50 has a modified or cut out upper section to more readily receive a driver tube 56. A string member 58, which could take the form of a wire, cable, thread, suture or the like, is used to apply tension to the upper crown 14 as the driver tube 56 advances the collar 50. The driver tube 56 may be an elongated tube configured to contact the collar 50 and to apply a downward pressure to the collar 50 to advance the collar 50 along the frame 10. The string member 58 extends through an opening in the upper crown 14 to counteract the downward force applied by the driver tube 56. This allows the frame 10 to remain stationary axially while the collar 50 advances distally to reconfigure the struts 12 and cinch the implant 1.

Figure 5E:
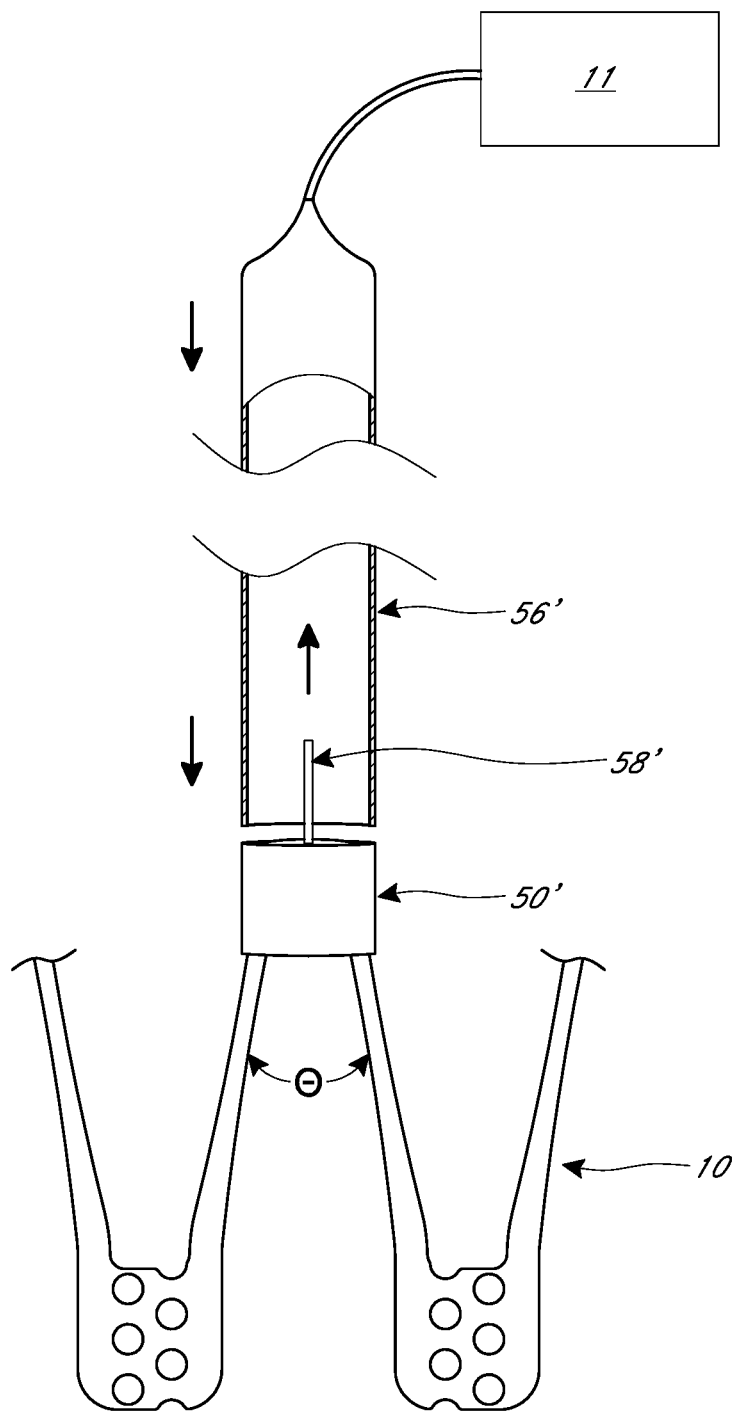

FIG. 5E is a partial side view of the frame 10 coupled with a frequency generator 11. The frequency generator 11 may be used with the various implants described herein, for example the implant 1, etc. The frame 10 is shown with a slider or collar 50', a pull wire 58' and a pusher tube 56'. The collar 50', pull wire 58' and/or pusher tube 56' may be analogous to the collar 50, the pull wire 58 and/or the driver tube 56, respectively. To advance the collar 50' over the frame 10 a high-frequency vibration can be added by the frequency generator 11 to assist the movement of the collar 50'. For example, relative vibrational movement between the collar 50' and the frame 10 may produce dynamic movement that facilitates overcoming a static friction between the collar 50' and the frame 10. The vibration could be transmitted through the pull-wire 58' and/or the pusher tube 56'. Vibration of either or both the pull-wire 58' or the pusher tube 56' will transmit the force to the frame 10 and collar 50' vibrating the frame 10 and collar 50' at a frequency to allow an easier movement between the frame 10 and collar 50'. An additional tensioning of the pull-wire 58' during the advancement will provide a force to the frame 10, changing the frame 10 upper apex shape from a wide angle to a more acute angle thus lessening the force required to advance the collar 50'. This combination of pull-force and vibration will lower the push-pull forces required to advance the collar 50' over the frame 10. The frequency transmitted through the tensioning wire and/or pusher tube 56' will lower these forces and could be coupled through each connection. A variety of suitable frequency generator tools could be used as the frequency generator 11 to transmit these vibrational frequencies, such as a CUSA system (Integra® CUSA® EXcel+ Ultrasonic Tissue Ablation System). The frequency may be, for example, from 1 to 100 KHz. The frequency can be varied during the procedure, tailored during the procedure or provided at a fixed defined frequency.

Figure 6A:
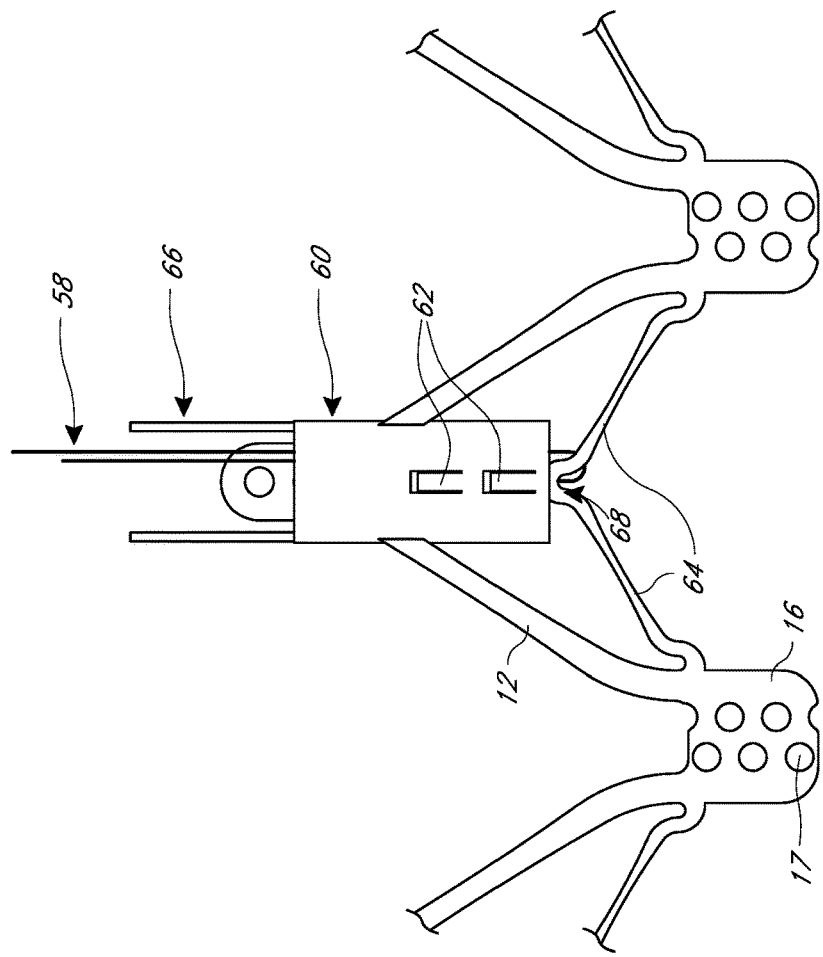
FIGS. 6A and 6B are side views of embodiments of a collar and frame that may be used with the implant of FIG. 1 shown, respectively, in an expanded and a cinched state.
Figure 6B:
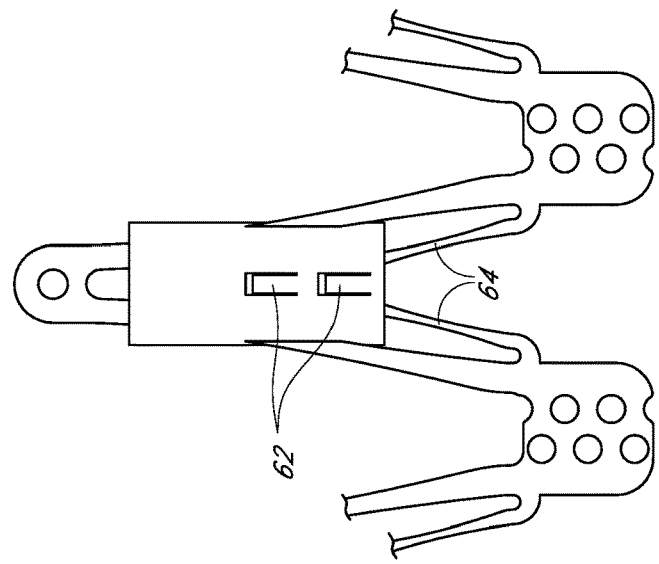
Figure 7D:
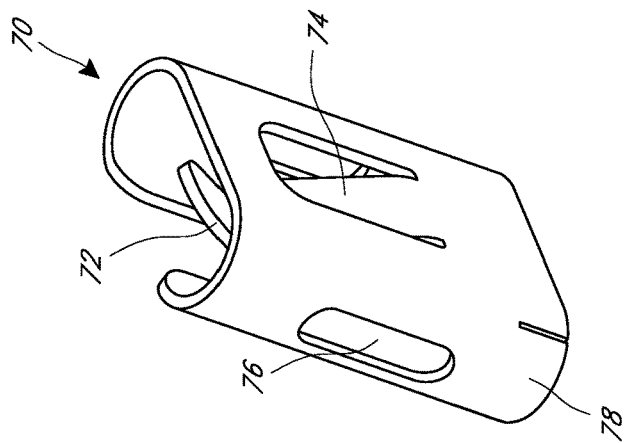
FIGS. 7A through 7D show, respectively, a circumferentially outward facing view, a side view, a circumferentially inward facing view, and a perspective view of an embodiment of a collar having locking tabs.
Figure 7C:
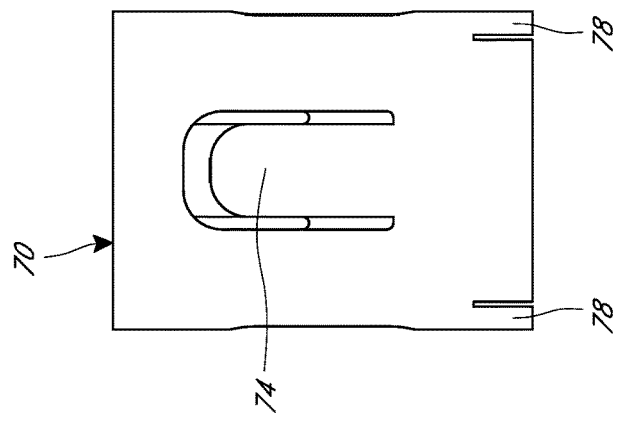
Figure 7B:
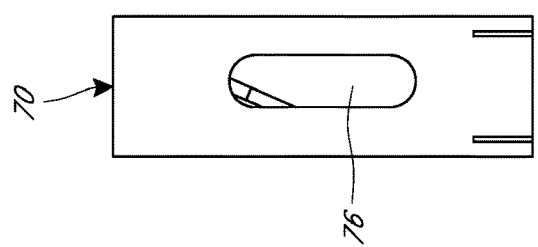
Figure 7A:
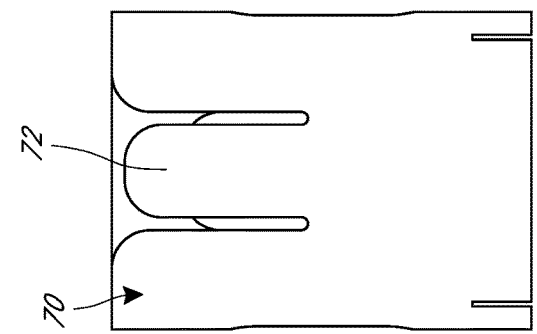

FIGS. 6A and 6B depict an alternate embodiment of the frame 10 and the frame/collar interaction. In addition to the struts 12, the frame 10 is further provided with mid-struts 64. The mid-struts 64 have crowns 68 and bridge the gap between lower apices 16. Locking tabs 62, of collars 60, engage with mid-strut crown 68 as collar 60 is advanced by operations of wire 58 and driver tube 66. The mid-strut crown 68 may be pulled proximally by the wire 58 to engage the locking tabs 62. The locking tabs 62 engage with the underside of mid-strut crowns 68 reducing the diameter of the frame 10 and cinching and locking the implant as shown in FIG. 6B. The collars 60 have sections removed along their sides from proximate mid collar to the collar distal end to accommodate movement of struts 12 as the collar is advanced over the mid-strut crown 68. Also, it is understood that rather than engaging with the underside of mid-strut crown 68, cut-outs could be provided in the surface of the mid-strut crowns 68. A driver tube 66 may act to drive the collar 60. The collar 60, locking tabs 62 and driver tube 66 may have the same or similar features and/or functionalities as, respectively, the collar 50, the locking tabs 54, and the driver tube 56, and vice versa.

FIGS. 7A through 7D are various views of another embodiment of a collar 70 that may be used with the various devices, systems and methods described herein. The collar 70 may have the same or similar features and/or functionalities as the other collars described herein, and vice versa. FIGS. 7A, 7B, 7C and 7D show, respectively, a circumferentially outward facing view, a side view, a circumferentially inward facing view, and a perspective view of the collar 70. The collar 70 includes locking tabs 72, 74. Here the locking tabs 72, 74 are on opposing sides of the collar 70. Two cut-outs 76 are located proximate the midsection of the sides of the collar 70. There may be only one or more than two cut-outs 76. Flex sections 78 are provided on either of the lower sides of the collar 70. There are numerous advantages of these features on the collar 70. For example, the lower tab 74 acts as a safety tab. As part of the assembly process, the lower tab 74 is positioned into engagement with a cut out in the upper crown 14, or, alternatively, the underside of the upper crown 14, of the implant 1. This may, for example, keep the collar 70 engaged with the upper crown 14 during the rigors of packaging and shipping and during the surgical procedure itself. As further example, both tabs 72, 74 can act as safety tabs by having multiple cut outs on either side of the upper crowns 14. In some embodiments, the cut outs 76 are created for preferential forming of the collar 70. For example, a starting material of a round hypotube may be crushed or swaged into an oval shape to slide the collar 70 over the upper crowns 14. Further, the flex sections 78 may reduce friction when the collar 70 is being advanced over the struts 12. The flex sections 78 may also minimize scraping of the collar 70 against the struts 12 of the frame 10 when the collar 70 is advanced. Additionally, as best seen with reference to FIG. 7D, when the collar 70 is advanced such that the upper locking tab 72 is engaged with the underside of an upper crown 14, the lower, inwardly biased tab 74 will help support upper tab 72 when it is advanced into locking engagement with the upper crown 14.

Figure 8C:
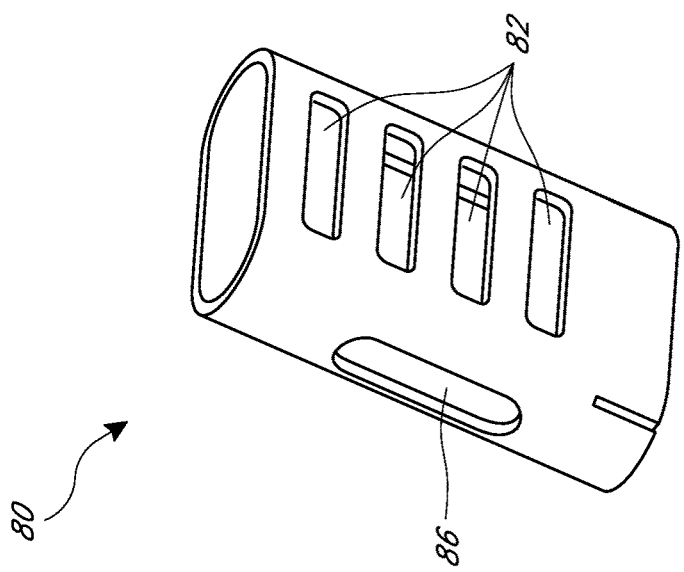
FIGS. 8A through 8C are various views of an embodiment of a collar having cutouts that may be used with the implant of FIG. 1.
Figure 8B:
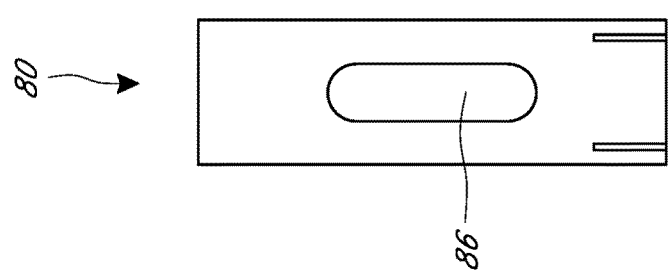
Figure 8A:
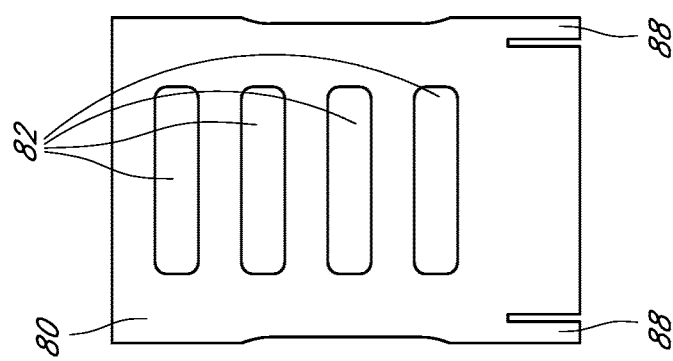

FIGS. 8A through 8C illustrate another embodiment of a collar 80 that may be used with the various devices, systems and methods described herein. The collar 80, also referred to as a "slider," may have the same or similar features and/or functionalities as the other collars described herein, and vice versa. FIG. 8A is a front view of the slider or collar 80, FIG. 8B is a side view of the collar 80, and FIG. 8C is a perspective view of the collar 80. This variation of the collar 80 is also provided with preferential forming cut outs 86 and flex sections 88, which may be similar or the same as the cutouts 76 and flex sections 78 as described with reference to the collar 70 in FIGS. 7A through 7D. In this embodiment, however, locking tabs are not provided on the collar 80. Rather, tabs are instead provided on the upper crown 14 (not shown) for locking engagement with cut outs 82 on the collar 80. These tabs would extend outwardly from the upper crown 14 and be downwardly biased.

Figure 9:
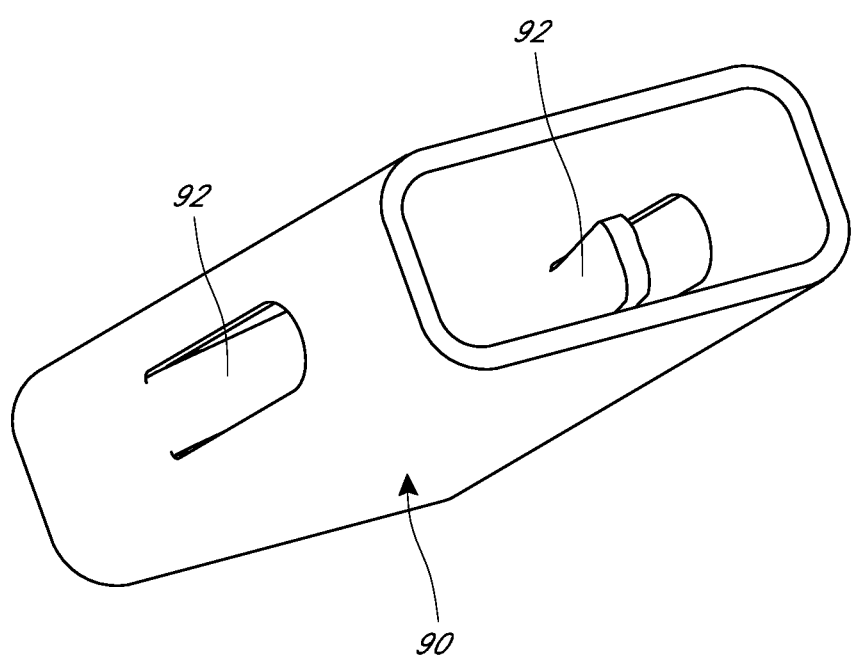
FIG. 9 is a perspective view of an embodiment of a collar with locking tabs.

FIG. 9 is a perspective view of another embodiment of a slider or collar 90. The collar 90 is provided with radial locking tabs 92. Locking tabs 92 are located on the sides of the collar 90 and are inwardly biased to engage with grooves (not shown) on the sides of the upper crowns 14 of the frame 10. Multiple levels of such grooves may be formed on the upper crown 14, and in addition or alternatively can be provided on the upper portions of the struts 12. Such grooves in either or both locations allow for more varied degrees of cinching of the implant 1.

Figures 10, 11:
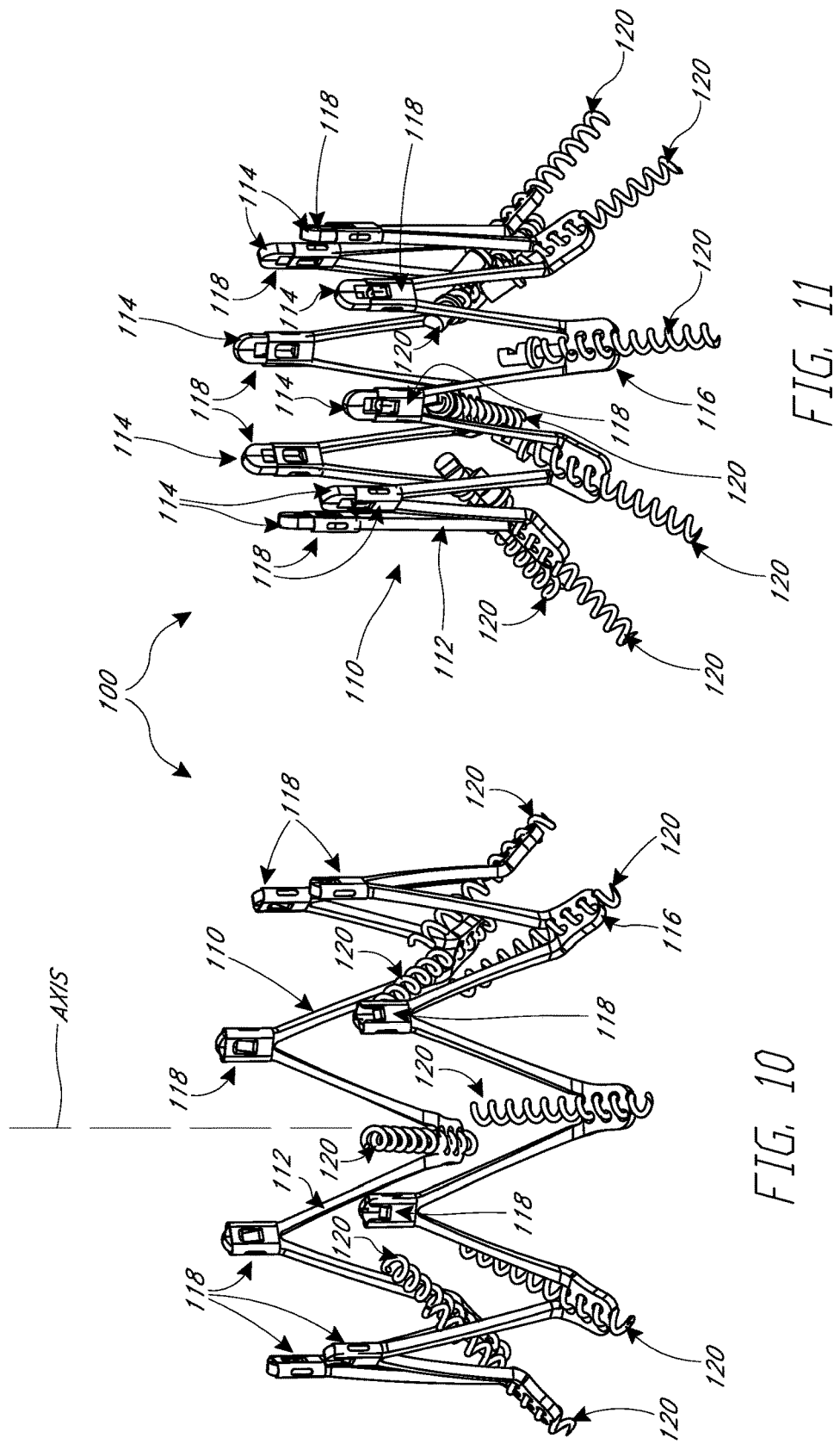
FIGS. 10 and 11 are perspective views of an embodiment of an implant having collars with locking tabs shown, respectively, in an expanded and a cinched state.

FIGS. 10 through 15 are perspective views of various embodiments of implants that may be used with the various systems and methods described herein. In FIGS. 10 through 15, only some of the same features may be labeled for clarity. For example, only some of the struts 12 may be labeled in the figures, etc. FIGS. 10 and 11 are perspective views of an embodiment of an implant 100. The implant 100 may have the same or similar features and/or functionalities as other implants described herein, for example the implant 1, and vice versa. The implant 100 is shown in an embodiment of an unconstrained state in FIG. 10. The implant 100 is shown in an embodiment of an anchored, cinched and locked state in FIG. 11. The implant 100 includes a frame 100 having struts 112, upper crowns 114, lower crowns 116 and anchors 120. These may be analogous to, for example, the frame 10, the struts 12, the upper crowns 14, the lower crowns 16, and the anchors 20, respectively. By "analogous" it is meant these features may have the same or similar features and/or functionalities as each other. The implant 100 has lower crowns 116 that are inclined at an angle with respect to the struts 112. The lower crowns 116 may be inclined downward and outward, or distally and outward, relative to the struts 112 and/or relative to the axis (shown in FIG. 10). In this manner, the anchors 120 may be directed more in a direction into the annular tissue above and proximate the heart valve, and less in a downward direction toward the valve leaflets. The angle may be measured between the direction the lower crowns 116 extend and a portion of the axis extending underneath the implant 100. The angle may also be measured between the direction the lower crowns 116 extend and the direction that the struts 112 extend downward. This angle may be between thirty to sixty degrees. In some embodiments, this angle is approximately forty-five degrees. The anchors 120 are formed as one piece. A variety of different types of anchors may be used with the implant 100. For example, other anchors described herein may be used, for example the anchor 20 having the anchor head 22 and anchor abutment 24, as described with respect to FIGS. 1 through 4. The implant 100 in FIGS. 10 and 11 includes opposing tab sliders or collars 118. The collars 118 may be analogous to the collars 70, described with respect to FIGS. 7A through 7D.

Figure 13:
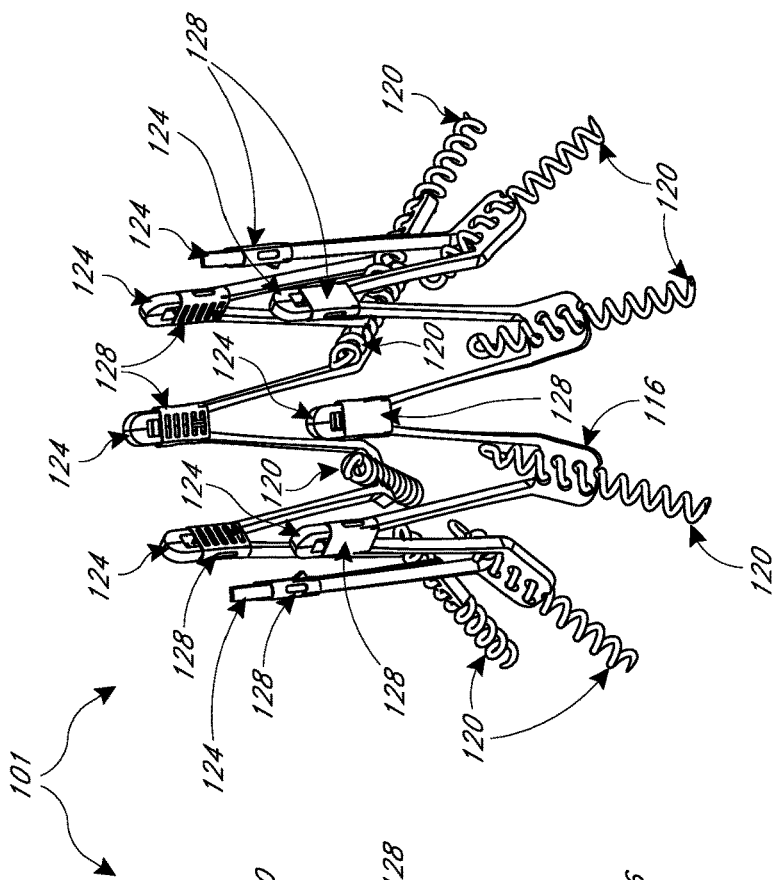
FIGS. 12 and 13 are perspective views of an embodiment of an implant having collars with cutouts shown, respectively, in an expanded and a cinched state.
Figure 12:
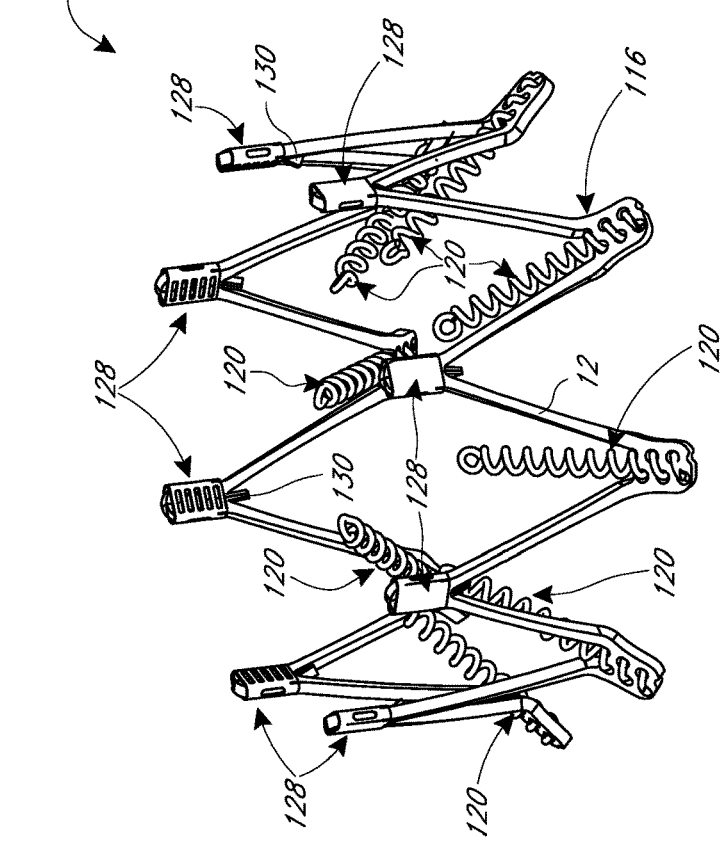

FIGS. 12 and 13 are perspective views of an embodiment of an implant 101. The implant 101 may have the same or similar features and/or functionalities as the implant 100, and vice versa. The implant 101 is shown in an embodiment of an unconstrained state in FIG. 12. The implant 101 is shown in an embodiment of an anchored, cinched and locked state in FIG. 13. The implant 101 has upper crowns 124 having locking tabs 130. The implant 101 also includes indexed sliders or collars 128. The collars 128 may be analogous to the collars 80 described with respect to FIGS. 8A through 8C. The tabs 130 are provided on the upper crowns 124 for locking engagement with the grooves formed in the collar 128. Such grooves may be similar to the grooves 82 of the collar 80.

FIGS. 14 and 15 are perspective views of an embodiment of an implant 102. The implant 102 may have the same or similar features and/or functionalities as the implant 100 and/or 101, and vice versa. The implant 102 is shown in an embodiment of an unconstrained state in FIG. 14. The implant 102 is shown in an embodiment of an anchored, cinched and locked state in FIG. 15. The implant 102 includes radial locking collars 148. The collars 148 may be analogous to the collars 90, described with respect to FIG. 9. Radially inwardly biased locking tabs 149 on the collars 148 engage with grooves 150 cut into the outer sides of the upper crowns 144. The pitch of the helically wound anchors 120 can be varied. The pitch of the last turn of the anchors 120 may also be varied, for example to self-lock the anchors 120 into the lower crowns 116. Moreover, the last or most distal turn of the helical anchors 120 may be swaged from a circular cross section to a more oval cross section to prevent backing out of the anchors 120 from the lower crown 116, for example to prevent backing out after engagement or anchoring in the heart tissue. Rather than swaging, pitch of the most distal turn of the helical anchors could be varied to prevent backing out.

FIGS. 16 and 17 are side views of a portion of an implant 103 in an uncinched and cinched state, respectively. The views indicate an embodiment of a method for cinching the implant 103 after anchoring. The implant 103 may be analogous to the various implants described herein, for example the implant 1, etc. The implant 103 includes a frame 160. The frame 160 may be analogous to other frames described herein, for example the frame 10, etc. The frame 160 has lower apices 166 which include eyelets 168. A string 172 is attached to or fed through the eyelets 168. Alternatively, the string 172 can carry enlargements, knots, and the like at its ends to prevent the ends from passing through the eyelets 168 as the frame 160 is cinched. String 172 can be made of wire, cable, suture, thread, or the like. Rotational member 170 is either fixedly attached to string 172 or string 172 is passed through a tunnel formed in the end of rotational member 170. FIG. 16 shows frame 160 in an unconstrained state. FIG. 17 shows the frame in its implanted state. After anchoring, the rotational member 170 is rotated thereby winding string 172 about the member 170. This action causes the gap between lower apices 166 to shorten thereby cinching, or reducing the diameter, of the frame 160.

FIGS. 18 and 19 show a variation of the implant 103 of FIGS. 16 and 17. In FIGS. 18 and 19, rather than have a rotational member cause the cinching, a string 180 is provided. The string 180 can take the form of a thread, suture, or the like. The string 180 is attached to a string 182 by way of loop or knot 188. The string 182 is similar to the string 172 shown in FIGS. 16 and 17. FIG. 18 shows the frame 160 in an unconstrained state, while FIG. 19 shows the frame 160 being brought towards a cinched state. As the proximal end of the string 180 is pulled by the operator to cause cinching of the frame 160, the knots 184 will click, one by one, through an eyelet 186 in the upper crowns 187. The knots 184 are sized so to be able to be pulled through the eyelet 186, but cannot reverse back through the eyelet 186.

In this manner, the knots 184 provide a locking function and multiple degrees of cinch of the frame 160. After the desired degree of cinching has been achieved, the proximal ends of the string 180 are secured to maintain tension and then cut and the ends removed from the system.

FIG. 20 is a partial side view of another embodiment of an implant 104. The implant 104 may be analogous to the other implants described herein, for example the implant 1, etc. The implant 104 includes features for cinching the frame 160. A string-like member 202 is passed through multiple eyelets 204 disposed on the lower apices 166. The string-like member 202 extends circumferentially about the lower section of the frame 160. A driver unit (not shown) can be used to grab and gather the string-like member 202 until the desired amount of reduction in the diameter of the frame 160, or cinching, is achieved. In some embodiments, other features described herein may be used with the string-like member 202 to cinch the string-like member 202, for example the string 180 or the rotational member 170.

Figure 21B:
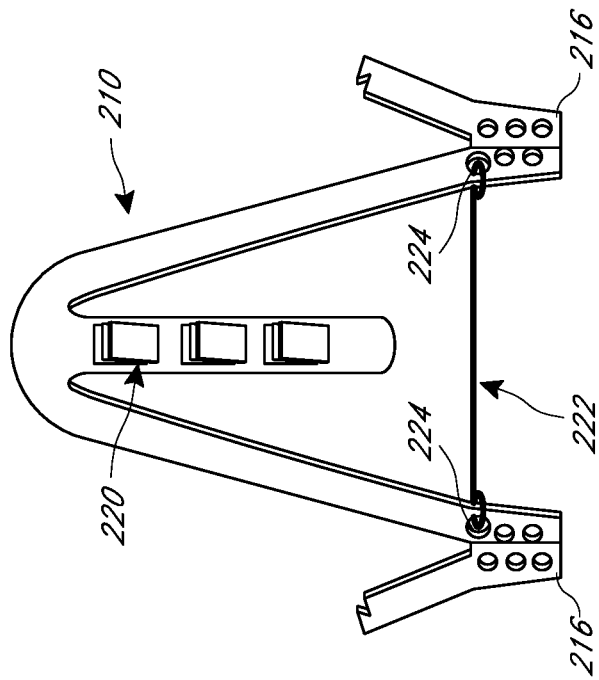
FIGS. 21A through 21D are partial sequential side views of an embodiment of a frame showing sequential cinching of adjacent struts using a string member and tabs.
Figure 21A:
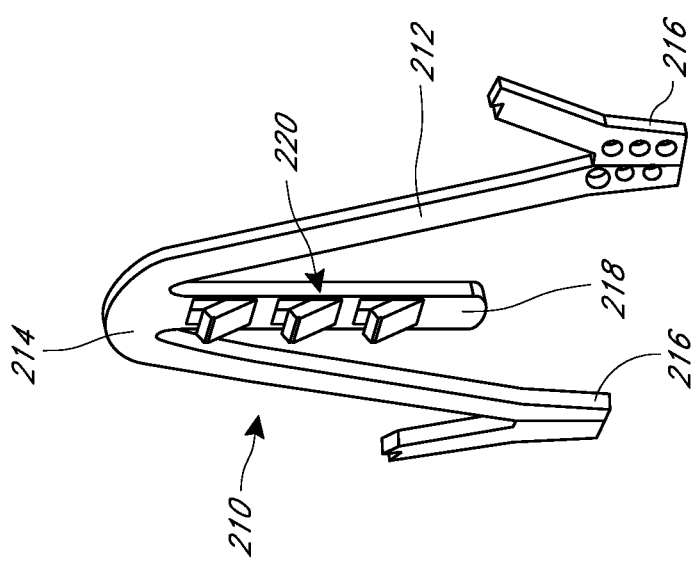
Figure 21D:
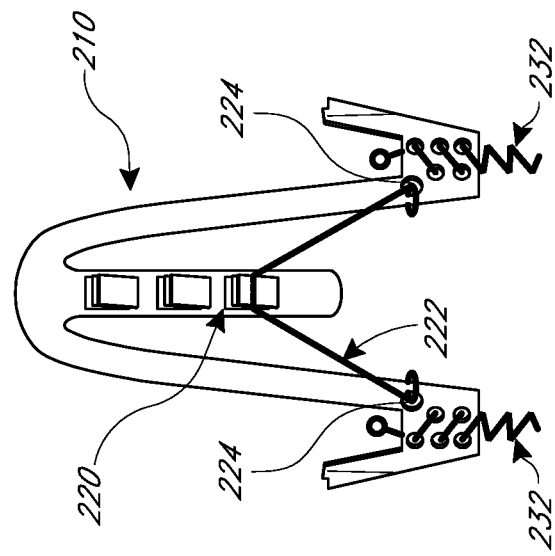
Figure 21C:
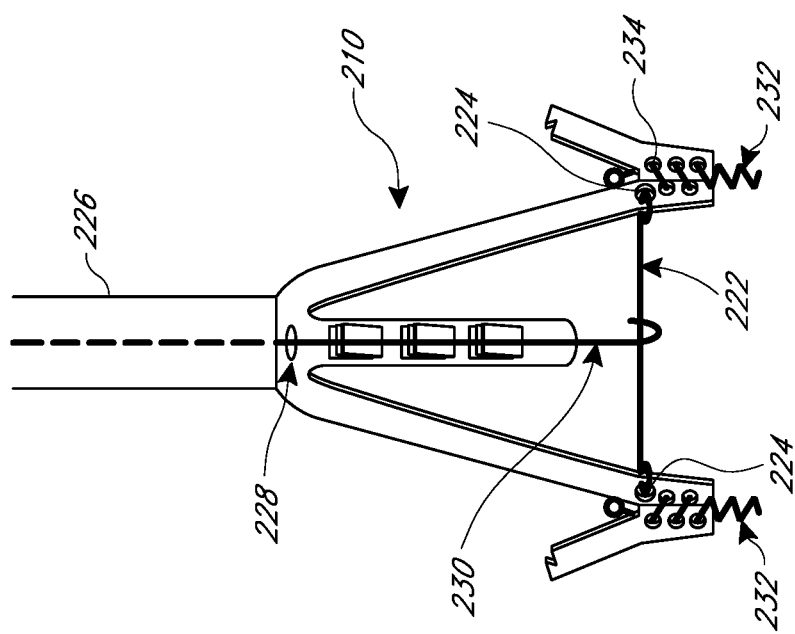

FIGS. 21A through 21D are partial side views of an embodiment of a frame 210 that may be used with the various implants described herein, for example the implant 1, etc. The views sequentially show a technique for cinching the frame 210. As shown in FIG. 21A, the frame 210 has struts 212, upper crowns 214 and lower crowns 216, which may be analogous, respectively, to other struts, upper crowns and lower crowns described herein. A central projection 218 extends downwardly from the upper crown 214 into the gap or valley bounded by adjacent struts 212. The central projection 218 includes three tabs 220. There may be fewer or greater than three tabs 220. The tabs 220 extend in an upwardly oriented and angled direction, e.g. outward, from the central projection 218. With reference to FIG. 21B, a string member 222 spans the distance between adjacent lower apices 216. The string member 222 may be between one, some or all distances between pairs of adjacent lower apices 216. The string member 222 can take the form of a wire, cable, suture, thread, or the like. The string member 222 is passed through one or more holes 224 in the lower crowns 216. The holes 224 are sized and positioned so as not to interfere with the rotation of helical anchors 232 as they are threadingly advanced through the holes 234 (see FIG. 21C). The anchors 232 may be analogous to other anchors described herein, for example the anchors 20, etc. The ends of the string members 222 may be knotted, for example for thread or suture string members 222. The ends of the string members 222 may be provided with a weld ball, collar, etc. crimped onto its ends, for example if the string members 222 are wire or cable. Such end features may prevent the ends of the string members 222 from being pulled through the holes 224 when tension is applied. As shown in FIG. 21C, a driver tube 226 is operated to apply tension to pull wire 230. For ease of operation, an alignment feature 228 can be provided to align pull wire 230 with central projection 218 and its tabs 220. Either by pulling or rotating driver tube 226, the operator applies tension to pull wire 230 which is hooked around string member 222. The operator can then apply varying degrees of cinching to frame 210 by ratcheting string member 222 up and into engagement with tabs 220. FIG. 21D shows the frame in one particular state of cinch. The string member 222 may be engaged with any of the tabs 220 to provide more or less cinching to the frame 210.

Figure 22B:
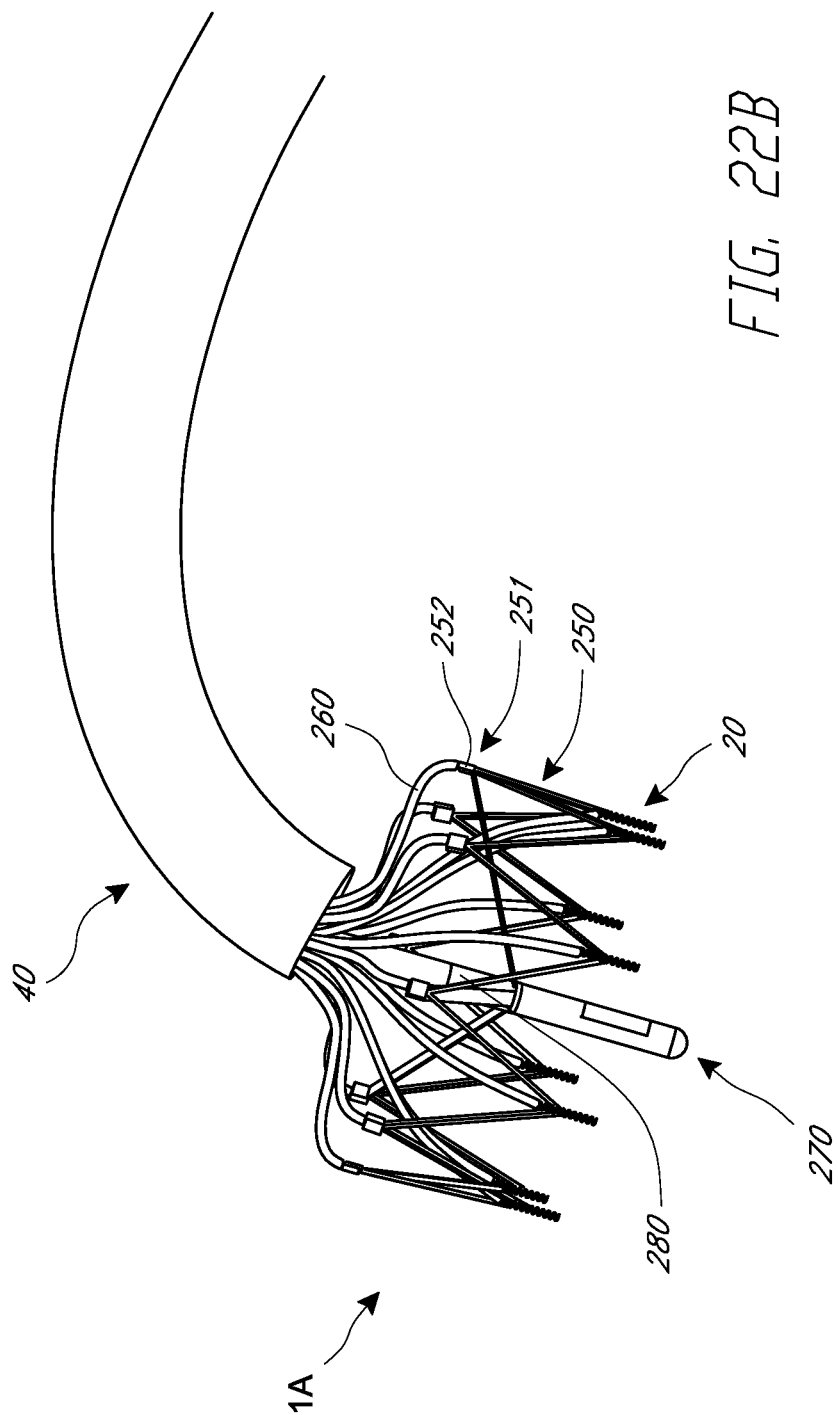

FIGS. 22A and 22B are perspective views of an embodiment of a distal end of a delivery catheter 40 being used to deliver an implant 1A. The delivery catheter 40 has various positioning and imaging capabilities. The distal end of the delivery catheter 40 is maneuvered into position above the heart valve annulus. The delivery catheter 40 may be used to deliver the various implants described herein, for example the implant 1, etc. The implant 1A shown being delivered in FIGS. 22A-22B is for resizing the heart valve annulus. It is understood that a variety of different implants may be delivered with the delivery system and methods described herein. The implant 1A may be analogous to the other implants described herein, such as the implant 1. By "analogous" as used herein it is meant the implant 1A may have the same or similar features and/or functionalities as the implant 1, and vice versa. As shown, this particular implant 1A includes a frame 250. The frame 250 has anchors 20 attached to a lower or distal portion of the frame 250 and extending distally therefrom. The frame 250 has an upper or proximal portion with collars 252 extending over upper crowns 251 of the frame 250. Only some of the collars 252, upper crowns 251 and anchors 20 are labelled for clarity. The collars 252 may be moved, e.g. distally, along the frame 250 by driver tubes 260 to resize the frame 250. The frame 250, upper crowns 251 and collars 252 may be analogous to the various frames, upper crown and collars described herein, such as the frame 10, upper crowns 14 and collars 18, and vice versa.

The frame 250, one or more driver tubes 260, and an intravascular cardiac echography (or "ICE") catheter 270 may be extended from the distal end of the delivery catheter 40. The frame 250 and driver tubes 260 may be analogous to the various frames and driver tubes described herein. The driver tubes 260 are shown engaging corresponding upper crowns 252 of the frame 250. A centering frame 280 maintains concentric positioning of the ICE catheter 270 relative to the frame 250 during deployment, alignment and positioning of the frame 250 above and proximate to the target heart valve annulus tissue. The centering frame 280 maintains a generally centered position of the catheter 270 relative to the frame 250. By centering the ICE catheter within the frame 250, the operator need only rotate the ICE catheter 270 to view each anchor 20 and placement of the anchors 20. Further, the ICE catheter 270 could be used to view various other individual features of the implant 1A, such as the collars 252, for instance to view the extent to which each collar 252 is advanced down and over upper crowns 251 of the frame 250, to more precisely adjust the size of the frame 250. The ICE catheter 270 could also provide significant benefit to an embodiment where a singular cinching mechanism or driver tube needs to be landed on each crown 251 of the frame 250 to adjust the sizing of the frame 250. An indexing feature (not shown) may also be provided on the ICE catheter 270, for example, such that actuation of the indexing feature by the operator causes the ICE catheter 270 to automatically move, or rotate, to the next anchor 20 position.

Figure 22C:
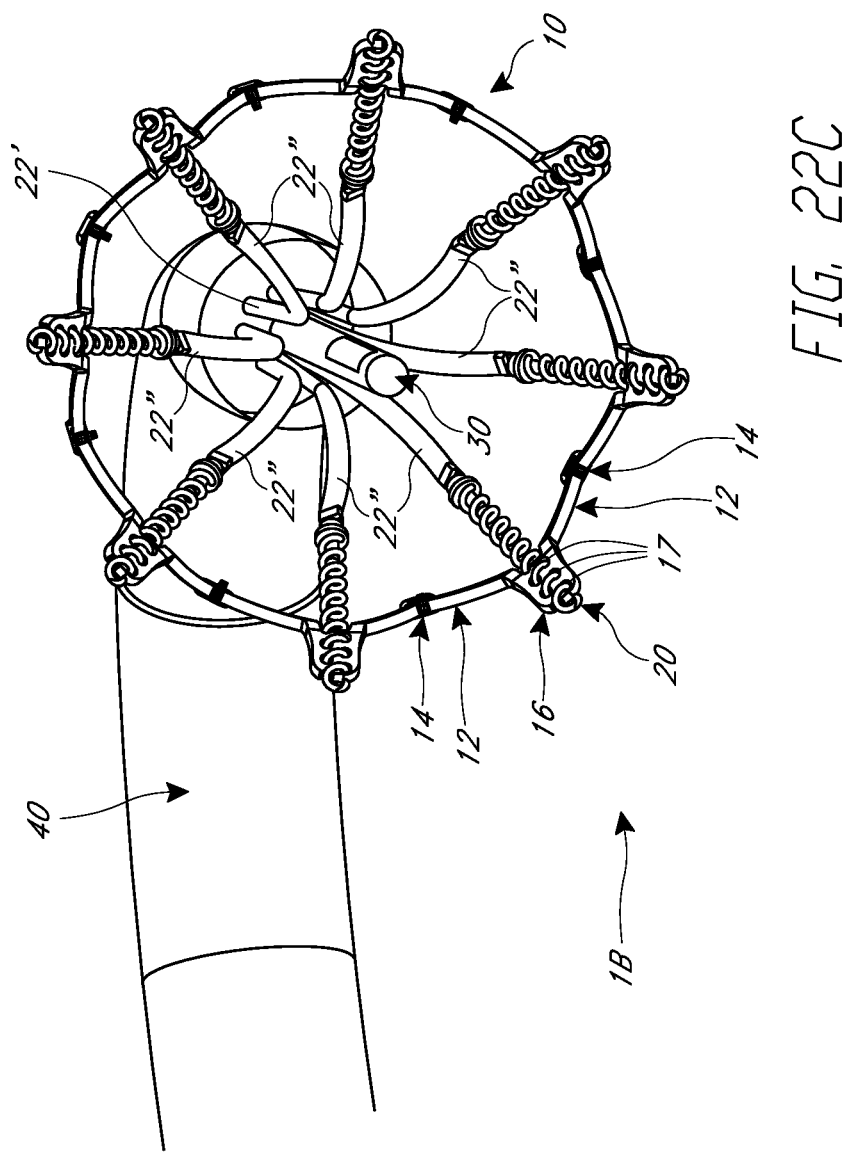

FIGS. 22C and 22D are perspective views of an embodiment of an implant 1B being delivered and implanted by the delivery catheter 40. The implant 1B may be analogous to the various implants described herein, such as the implants 100, 101, 102, and vice versa. As shown in FIGS. 1C and 1D, the implant 1B includes a frame 10 with struts 12 forming upper apices or crowns 14 and lower apices or crowns 16. The lower crowns 16 have openings 17, such as holes, aligned to receive the anchors 20 there through. For clarity, only some of the upper crowns 14, lower crowns 16, struts 12 and anchors 20 are labelled in FIGS. 1C and 1D. The anchors 20 may be rotated to move distally through the openings 17. The implant 1B is intended to be delivered proximate to and above a cardiac valve (tricuspid, mitral) annulus, and subsequently implanted in the annular cardiac tissue just above the plane of the valve orifice.

Driver tubes 22', having proximal portions 22" extending out of the delivery catheter 40, are provided for rotationally engaging the anchors 20. Manipulation, for example rotation, of the driver tubes 22' by the operator causes the anchors 20 to advance towards, engage with and penetrate cardiac tissue to secure frame 10 into the annulus approximate and above the valve. The anchors 20 may be advanced individually one at a time, some advanced together, or all advanced together. In some embodiments, the driver tube 22' may rotate relative to the proximal portion 22". In some embodiments, the driver tube 22' and proximal portion 22" are part of the same, continuous driver tube and/or the entire tube 22' and proximal portion 22" may rotate together.

An embodiment of an ultrasound catheter 30, such as the Acuson IPX8 AcuNav catheter, is shown contained within and advanced down a central lumen of the delivery catheter 40. The ultrasound catheter 30 may be analogous to the ICE catheter 270. In some embodiments, by rotating the ultrasound catheter 30 around the inside of the valve annulus, the relative position of the frame 10, and of any valve leaflets, will be seen for accurate positioning of the anchors 20 around and above the valve annulus.

In some embodiments, the ultrasound catheter 30 is contained within and advanced down an offset, non-central lumen of the delivery catheter 40. In this manner, the ultrasound catheter 30 would not interfere with the frame 10, its attachments or other features, and the driver components. In some embodiments, the ultrasound catheter 30 may be located and steered to the side of the annulus to image, allowing for less rotation to more quickly view the anchor points of the frame 10. An offset lumen could exit more proximally with regard to the distal end of the delivery catheter 40. This more proximal exit would reduce the overall profile or diameter of the distal end of the delivery catheter 40. In addition, this more proximal exit port would enable a view of the valve annulus from above. The offset lumen could also be compressible allowing for an even smaller profile until the ultrasound catheter 40 is advanced through the offset lumen.

While the ultrasound catheter 30 is shown integrated into the same delivery system as the delivery catheter 40, in some embodiments the ultrasound catheter 30 could otherwise be introduced secondarily through another entry site, such as through the aortic valve, and placed near or inside the implant for imaging and placement of the anchors 20.

FIG. 22E is a perspective view of an embodiment of a centering frame 32 coupled to the ultrasound catheter 30 and to an implant 1C. The implant 1C may be analogous to other implants described herein, such as the implants 1, 1A, 1B, and vice versa. The centering frame 32 has centering arms 34 connected to a centering hub 36 that is mounted on the ultrasound catheter 30. As the distal end of the delivery catheter 40 is maneuvered into position above the heart valve annulus, the centering frame 32 maintains concentric positioning of the ultrasound catheter 30 relative to the frame 10 during deployment, alignment and positioning of the frame 10 above and proximate to the target heart valve annulus tissue. The centering aspect is desirable, for example, because if the ultrasound catheter 30 remains centered within the frame 10, the operator such as a surgeon or technician need only rotate the ultrasound catheter 30 to view each anchor 20 and placement the of each anchor 20. There may also be an indexing feature (not shown) on the ultrasound catheter 30 such that actuation of the indexing feature by the operator causes the ultrasound catheter 30 to automatically move, or rotate, to the next anchor position. The centering frame 32 may be used with delivery of the various implants described herein, such as the annulus resizing implants and/or the heart valve replacement implants.

Figure 23:
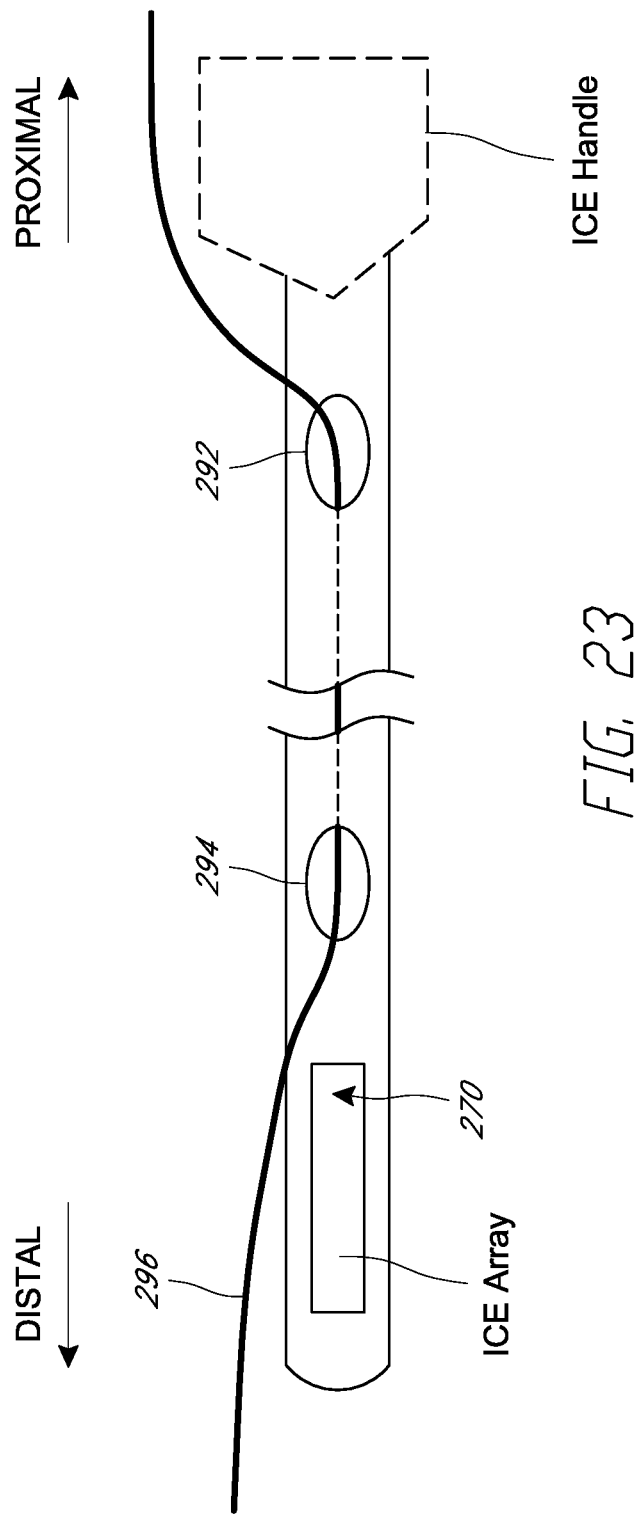
FIG. 23 is a side view of an embodiment of an intravascular cardiac echography (ICE) catheter for delivering, e.g. aligning and positioning, the various implants described herein, and having a guidewire entering and exiting the catheter.

FIG. 23 is a side view of an embodiment of an ICE catheter 270. The ICE catheter 270 as shown includes a guidewire entry port 292 and a guidewire exit port 294 which together accept the guidewire 296. This embodiment allows the ICE catheter 270 to be delivered separately from the frame 10 thereby reducing the overall diameter of the delivery catheter 40 (e.g. as shown in FIGS. 22A and 22B). An ICE handle may be located at a proximal end of the catheter 270. An ICE array may be located at the distal end of the catheter 270.

In some embodiments, a separately delivered ultrasound catheter 270 could be functionally linked to the distal end of the delivery catheter 40 and to the inside of the frame 10. The delivery catheter 40 could have mechanical docking and radiopaque features to aid in delivery and stability of the ultrasound catheter 270 relative to the delivery catheter 40.

Figure 24C:
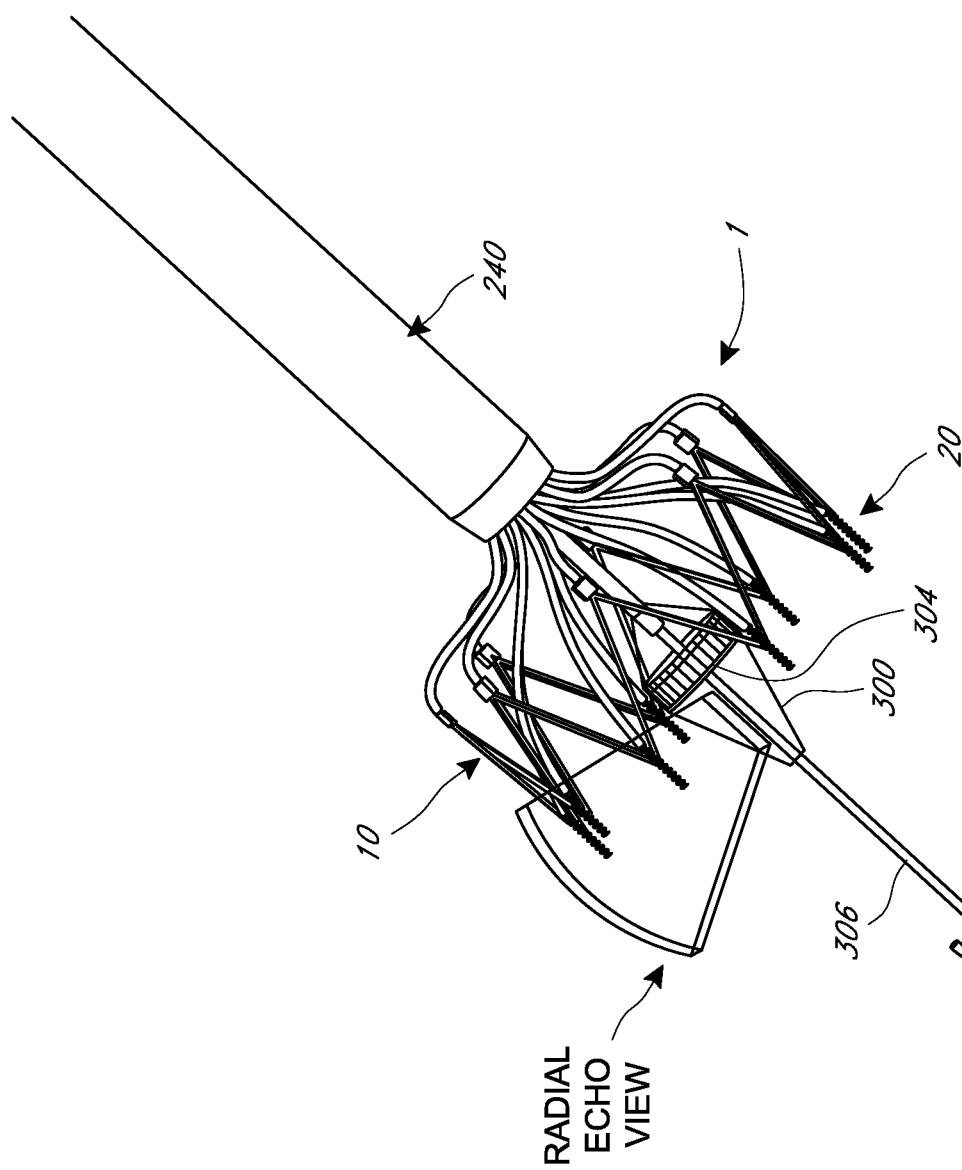

FIGS. 24A, 24B, 24C and 24D depict an embodiment of an ICE catheter 300 that may be used with the various implants and delivery devices, systems and methods described herein. The ICE catheter 300 has radial ultrasonic transducers 302, circumferential ultrasonic transducers 304 and guidewire 306 passing centrally therethrough. A guidewire lumen 303 extends out from a delivery catheter 240. The delivery catheter 240 may be analogous to the delivery catheter 40. The ICE catheter 300 extends out through the guidewire lumen 303. FIGS. 24B and 24C show the implant 1 deployed with the ICE catheter 300 tip. The other implants described herein may be delivered with the ICE catheter 300, such as the implants 1, 1A, 1B, 1C, and the implants 500, 520, 530 described below, etc. FIG. 24C further shows the relationship of the ICE catheter 300 to the delivery catheter 240 while it is taking a radial echo view to properly position the anchor 20 for insertion into heart valve annulus tissue. FIG. 24C shows the ICE catheter 300 capturing a circumferential echo image for properly positioning the frame 10 in a plane above the heart valve and its leaflets. The features shown and described in FIGS. 24A-24D may be used to deliver various other implants, such as other resizing devices or heart valve replacement valves.

In some embodiments, software or electronic controls can be effective to cycle through the radial cross sectional images around the valve annulus perimeter, relieving the need to physically move, via rotation, translation or deflection, the ICE catheter 300. A larger circumferential transducer array could also be placed distal of the annulus to not interfere with space limitations of the delivery catheter 240, further decreasing the profile of the delivery catheter 240. In another embodiment, the transducers of the ICE catheter 300 could generate a three dimensional image of the annulus of frame 10. The user could then more readily see the relative alignment of the annulus, valve leaflets and the implant 1.

FIGS. 25A through 25E are sequential perspective views of an embodiment of a delivery system 401 with imaging capability showing an embodiment of a method for the delivery, positioning and anchoring of the various implants described herein for resizing the native valve annulus. While FIGS. 25A through 25E depict delivery of the implant 1 for resizing the annulus, it is understood that implants for replacing the valve may also be delivered with the system 401. The implant 1 may be delivered, positioned and anchored to reshape the valve annulus. The implant 1 may be inserted using the delivery system 401 via access to the vasculature of the leg, in particular the femoral vein or the iliac vein. The system 401 may include the various implants, catheters and other features described herein, for example the implant 1, the delivery catheter 240, the ICE catheter 300, the guidewire 306, etc. The system 401 may include any of the implants described herein, for example implants including valve annulus reshaping devices or valve replacements that include valve leaflets.

Figure 25A:
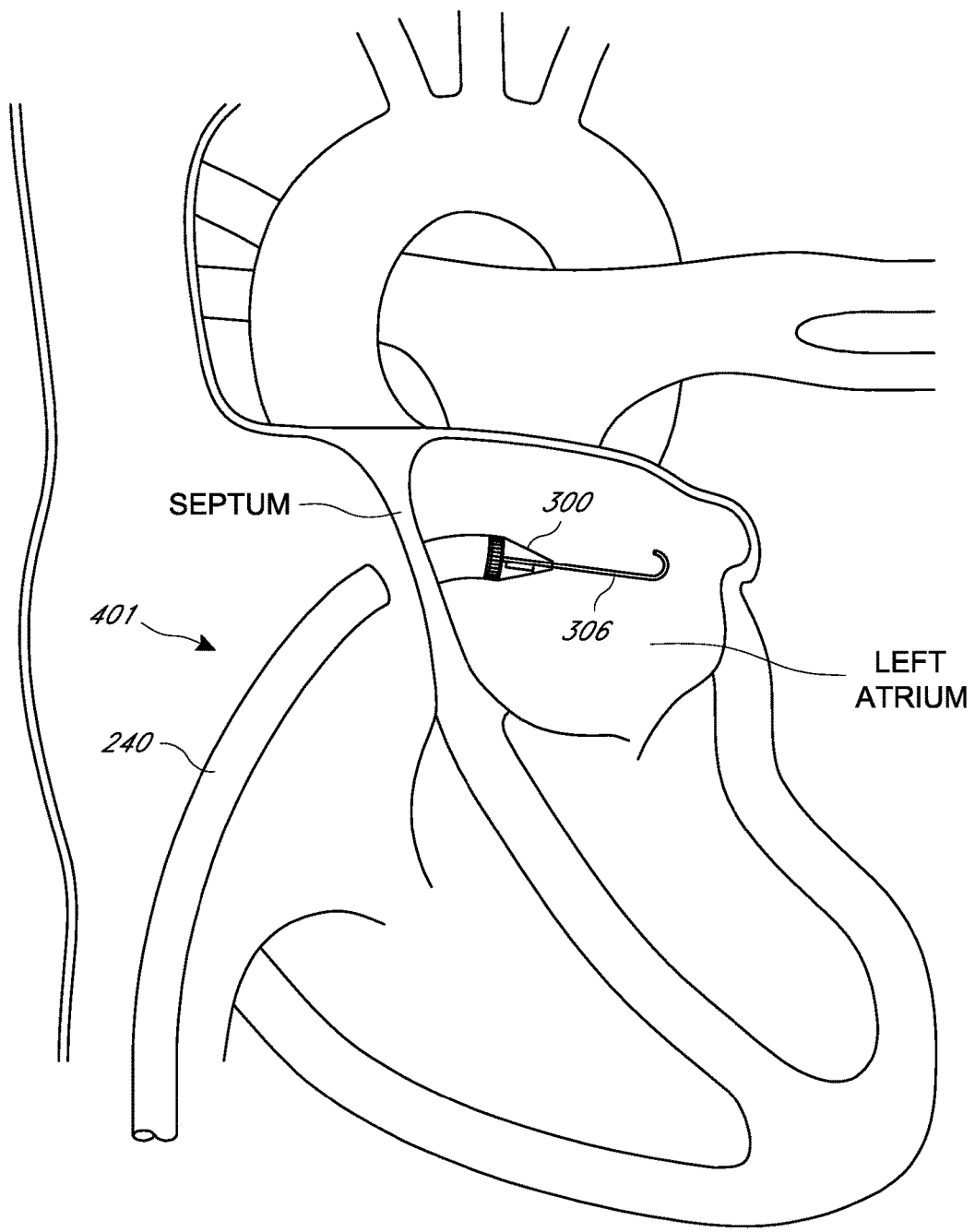
FIGS. 25A through 25E are sequential perspective views of an embodiment of a delivery system with imaging capability showing an embodiment of a method for the delivery, positioning and anchoring of the various implants described herein for resizing the native valve annulus.
Figure 25B:
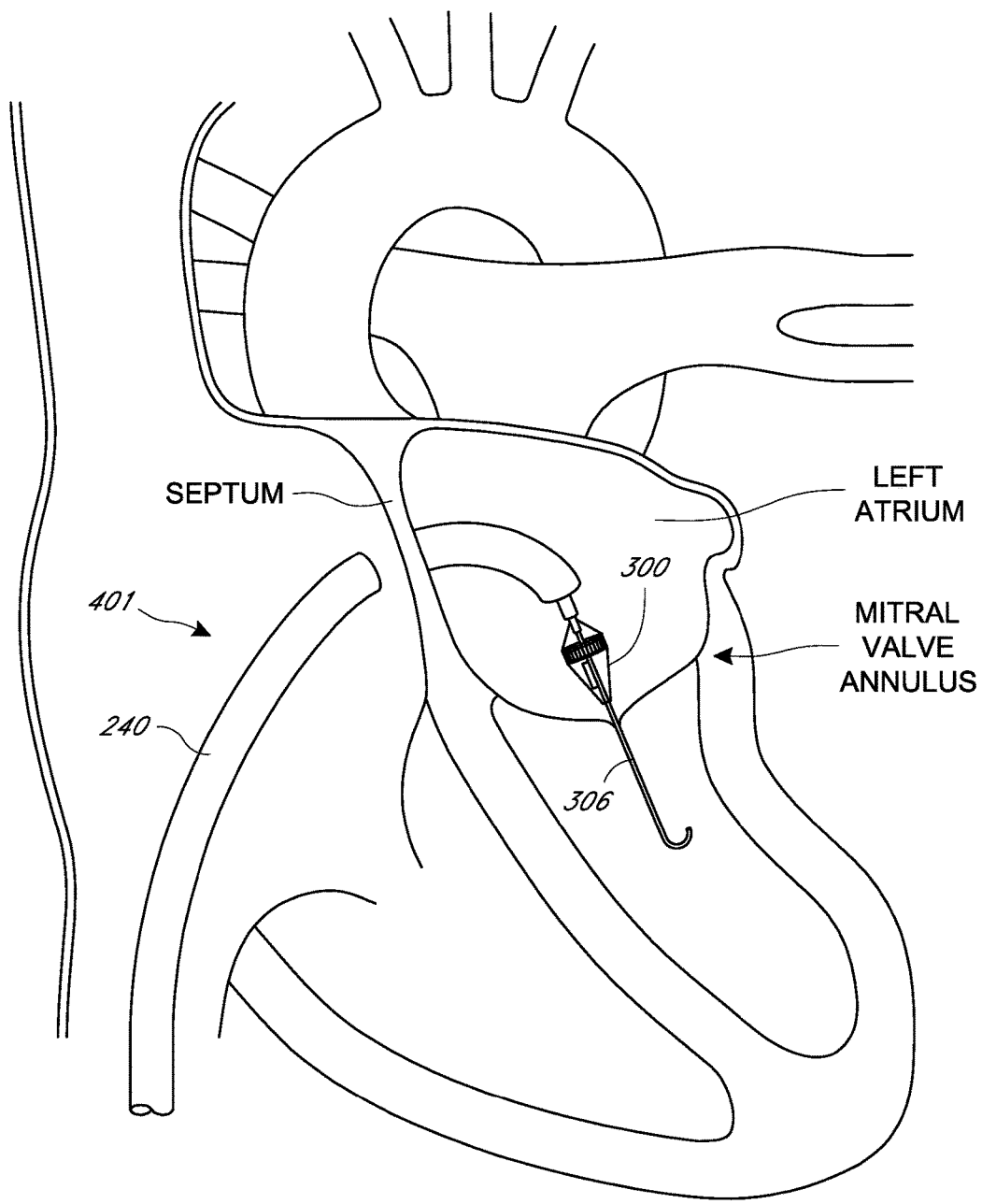
Figure 25C:
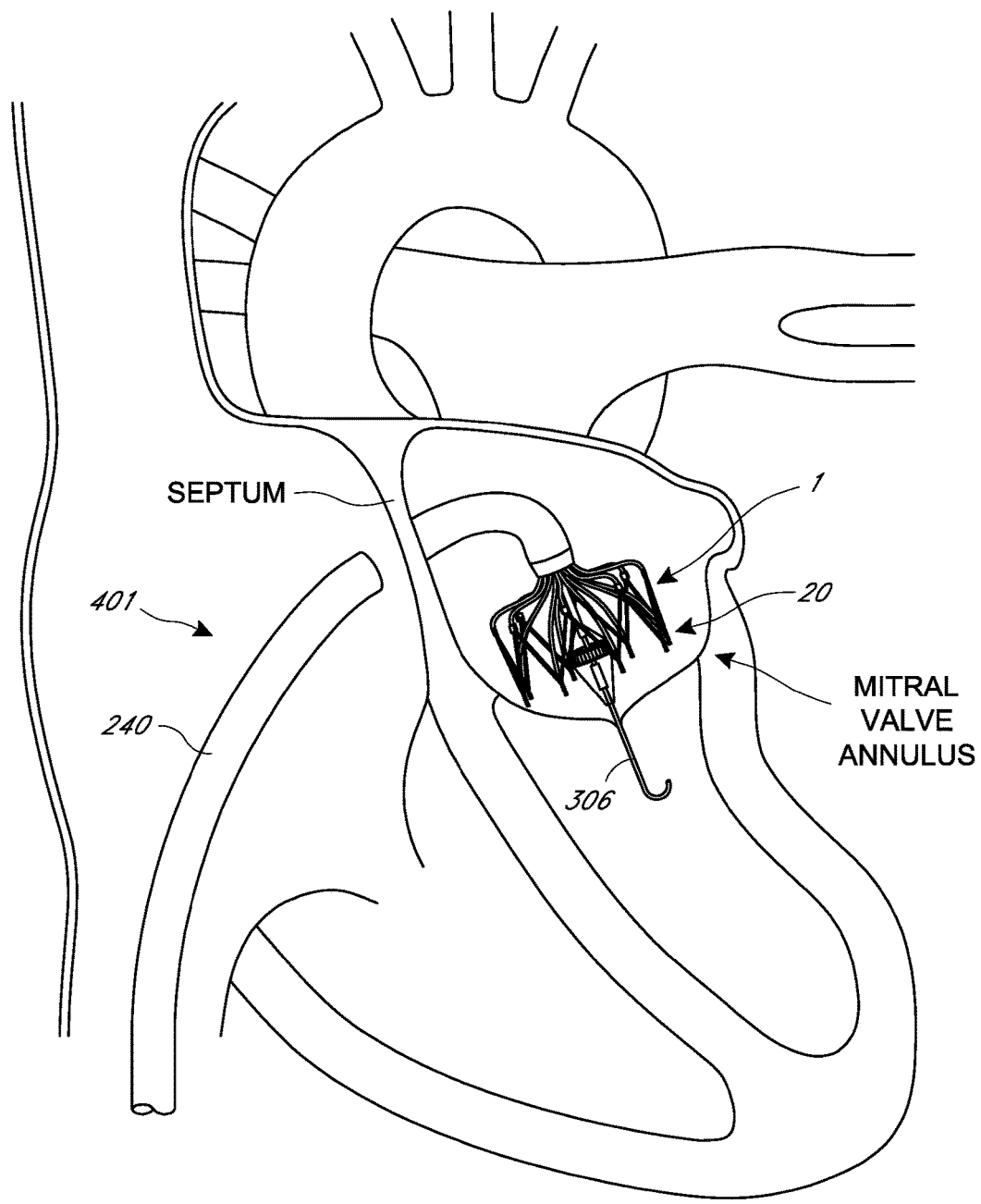
Figure 25D:
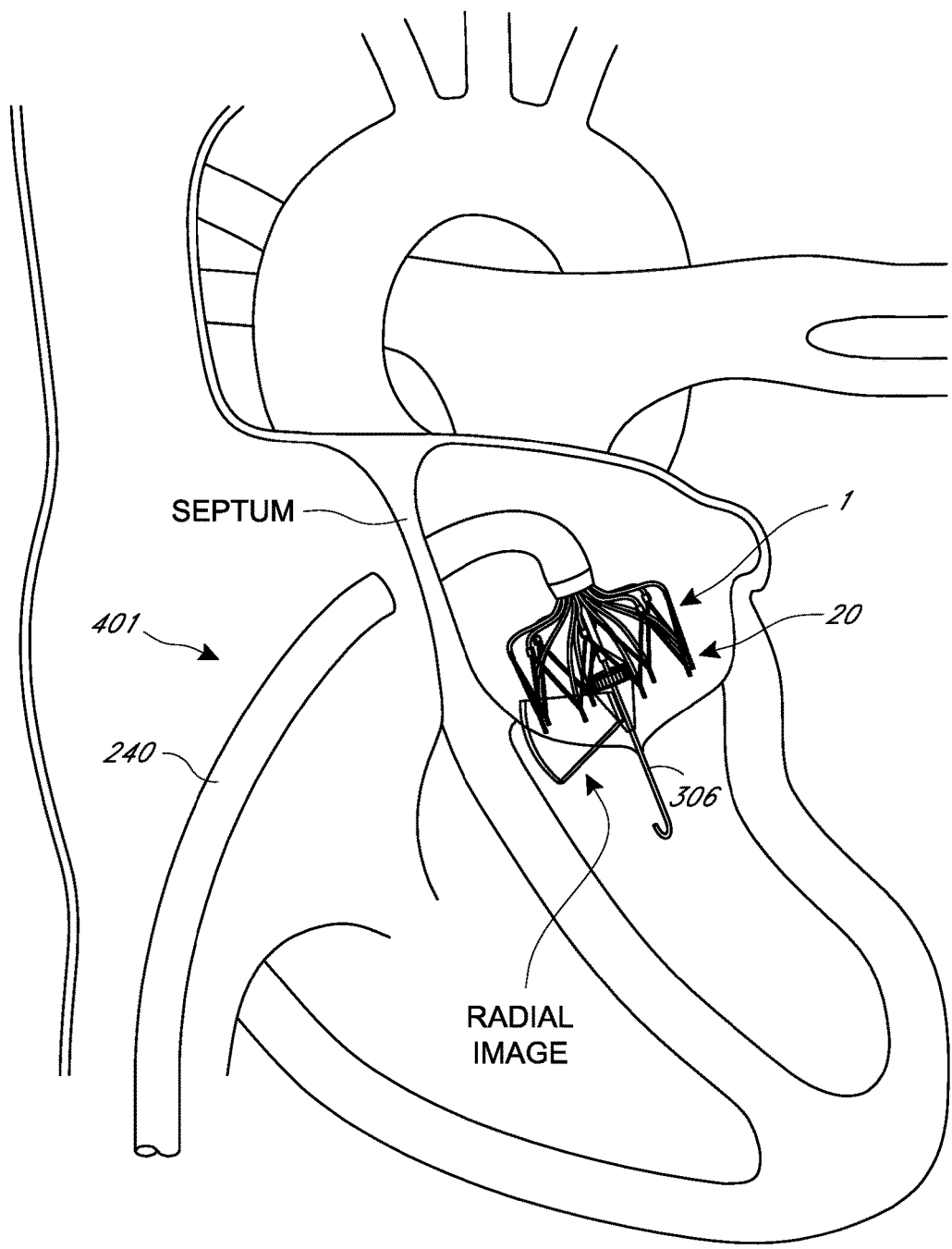
Figure 25E:
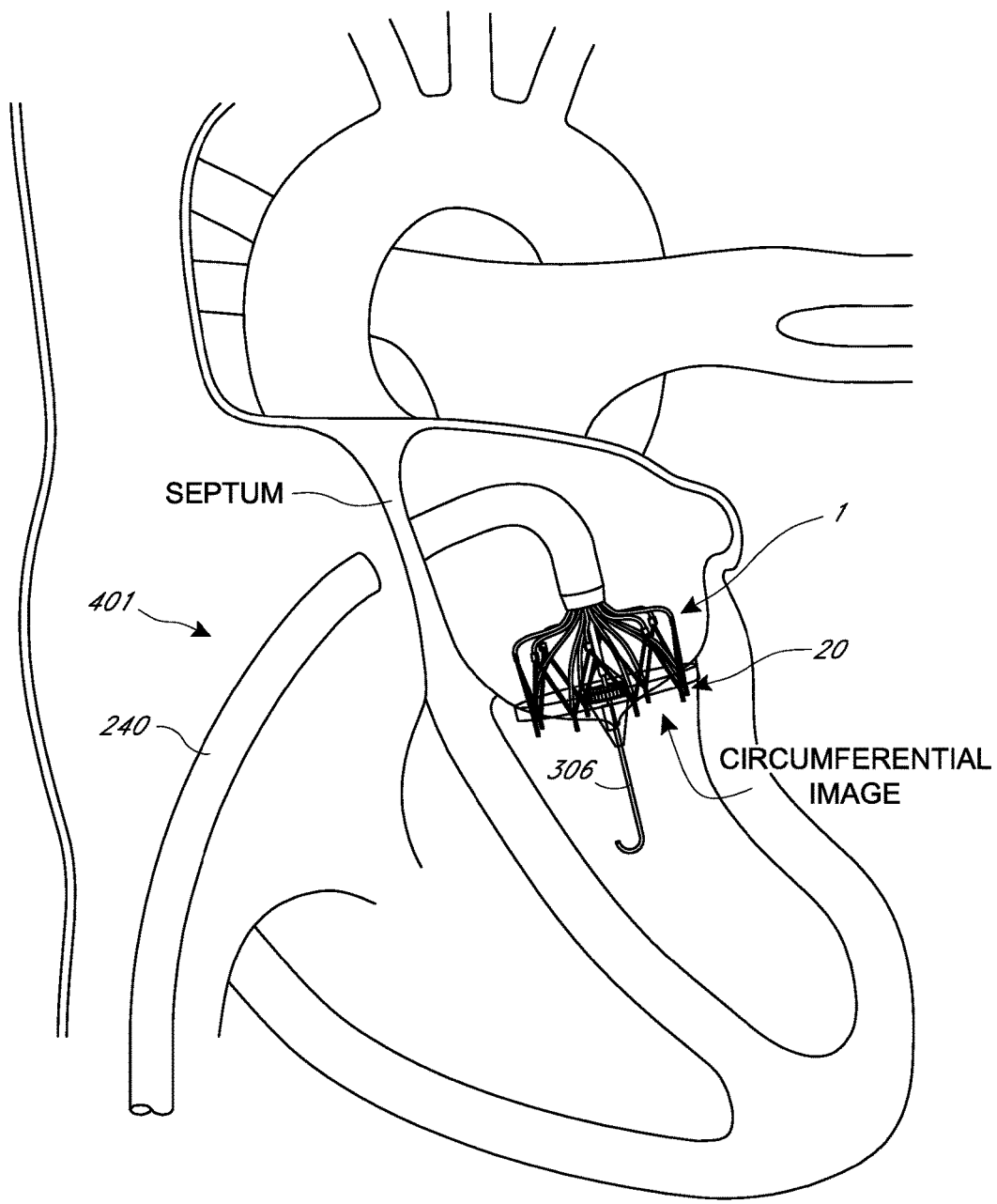

As shown in FIG. 25A, the system 401 is then advanced across the septum separating the upper chambers of the heart. The ICE catheter 300 is advanced to a position above the heart valve annulus, for example, the mitral valve annulus, as shown in FIG. 25B. FIG. 25C shows the implant 1 expelled from the distal end of the delivery system 401 above and proximate to the mitral valve annulus. A series of radial images are taken to properly position the anchors 20 for insertion into the mitral valve annulus tissue, as shown in FIG. 25D. Subsequently, a circumferential image is captured, as shown in FIG. 25E, to confirm that all anchors 20 are appropriately placed and anchored in the mitral valve annulus tissue above the mitral valve leaflets. If one or more anchors 20 are not positioned or anchored properly, they can be rotationally retracted, repositioned and re-anchored prior to removal of the driver tubes. In addition, a circumferential image can be taken prior to anchoring to confirm location of the lower crowns 16 of the frame 10 of the implant 1. It should also be understood that treatment of the tricuspid valve could involve insertion of the system 401 for access through the jugular vein whereby the system is then advanced down the superior vena cava and into the right atrium proximate and above the tricuspid valve annulus.

Figure 26:
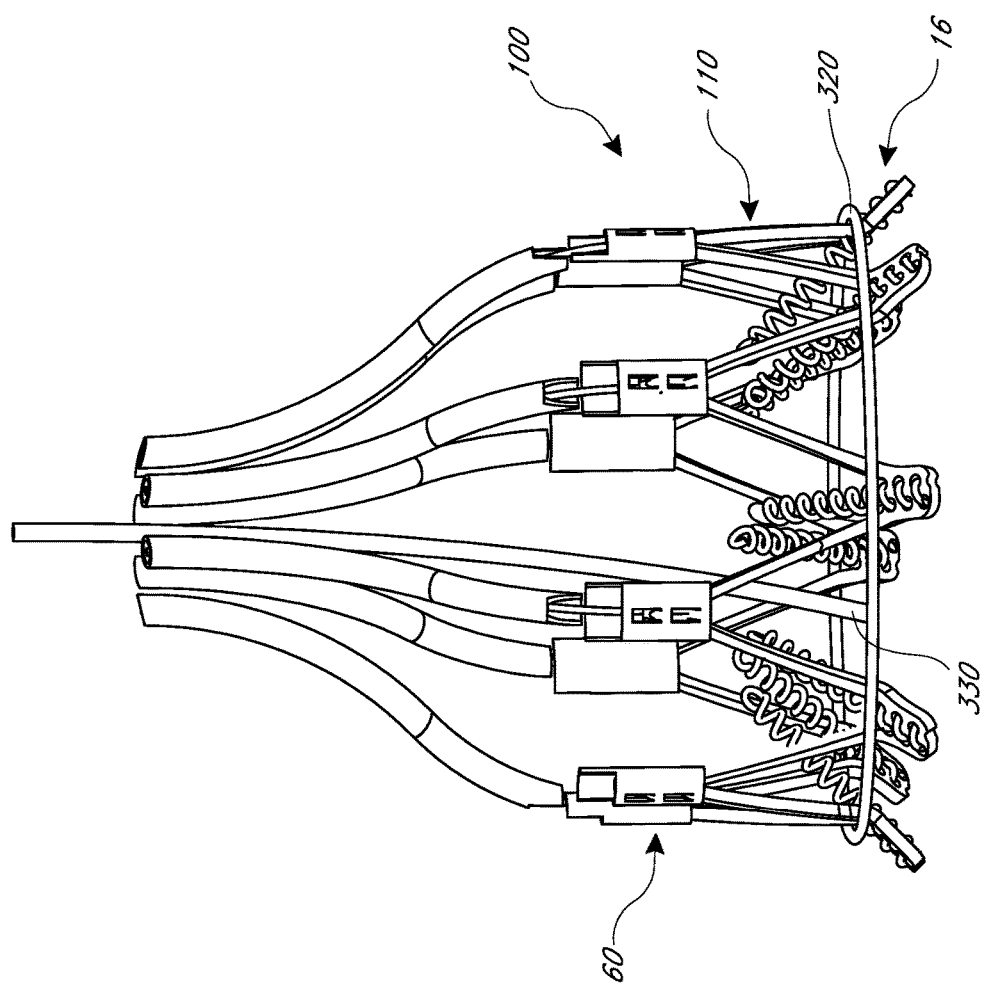
FIG. 26 is a side view of an embodiment of an implant having a constricting loop and is shown interacting with a delivery system for advancing the collars.

FIG. 26 is a perspective view of an embodiment of an implant 100 having a constricting loop 320. The implant 100 is shown interacting with a delivery system for advancing the collars 60. The constricting loop 320 may be used with other embodiments of the implant described herein, for example the implants 101, 102, etc. As shown in FIG. 26, the constricting loop 320 is provided. The constricting loop 320 encircles the frame 110 proximate the lower crowns 16. The constricting loop may encircle upper portions of the lower crowns 16 as shown, or other portions. A constricting loop actuator 330 may be provided to act on and constrict the constricting loop 320. For example, the actuator 330 may include a wire with a loop through which the constricting loop 320 extends, and where pulling the wire proximally will constrict and tighten the constricting loop 320 about the frame 110. In operation, the constricting loop 320 may be actuated first, allowing the operator to first predetermine the desired diameter of the frame 110. The collars 60 may then be advanced, cinching the frame 110 and locking it in the desired diametric dimension. In some embodiments, other collars described herein may be implemented. The constricting loop 320 is then removed. Constricting the frame 110 also reduces resistance to advancement of the collars 60. Furthermore, the constricting loop 320 assists in collapsing the frame 110 into the distal portion of the delivery catheter. Moreover, the constricting loop 320 helps reduce friction between the flared lower crowns 16 and the inner diameter of the delivery catheter. Additionally, a proximal loop can be utilized to restrict the proximal portion of the frame 110 to change the angle at which the anchors address the valve annulus.

Figure 27A:
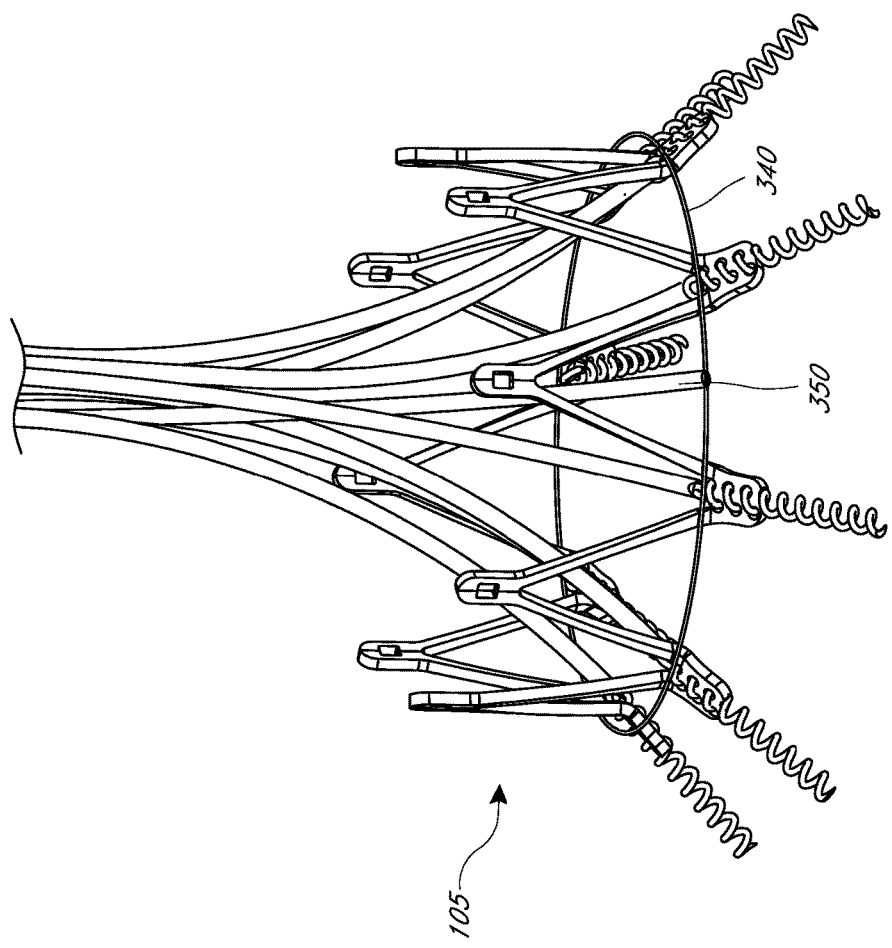
FIGS. 27A and 27B are side and detail views, respectively, of an embodiment of an implant having a cinch loop and is shown interacting with a delivery system for advancing the anchors.
Figure 27B:
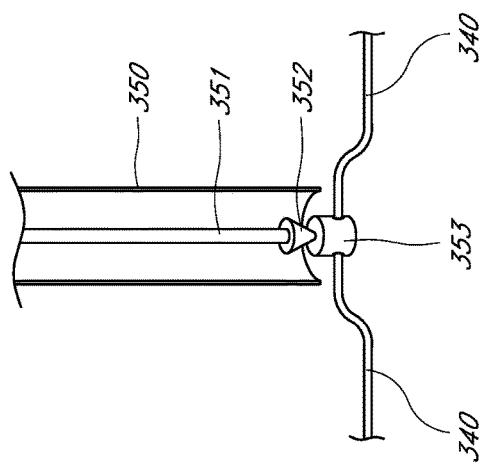

FIG. 27A is a perspective view of an embodiment of an implant 105 having a cinch loop 340. In this variation, the implant 105 does not include collars and the cinch loop 340 is provided to cinch and lock the frame of the implant 105 in the target heart valve annulus tissue. After anchoring, the cinch loop 340 is tightened down by operation of a cinch loop driver 350. FIG. 27B is a detail view showing a close up view of the driver 350 interacting with the loop 430. The driver 350 may include an inner tube or member 351 extending therethrough to or near a distal opening of the driver 350. A distal member 352, such as a wedge, may be attached to the distal end of the inner tube 351. The distal member 352 removably attaches to an element 353, for example by threaded engagement, friction fit, or other suitable engagement means. The loop 340 extends through or is otherwise attached to the element 353, locking the loop 340 in place. Pulling the element 353 in the proximal direction, for example by moving the driver 350 proximally, and/or pulling the inner tube 351 proximally, the loop 340 reduces in circumference around the implant 105, cinching the frame to a smaller diameter. The ends can then be snipped and driver 350 and inner tube 351 withdrawn. Once the operator has achieved the desired reduction in diameter of the anchored frame, the cinch loop 340 is locked in place and the cinch loop driver 350 is removed. In some embodiments, the cinch loop 340 may engage with the frame 110, for example with the lower crowns 16, to lock in place. Such engagement may be by friction fit, openings in the lower crowns 16 that allow for unidirectional movement of the loop 340, or other suitable means.

Figure 28:
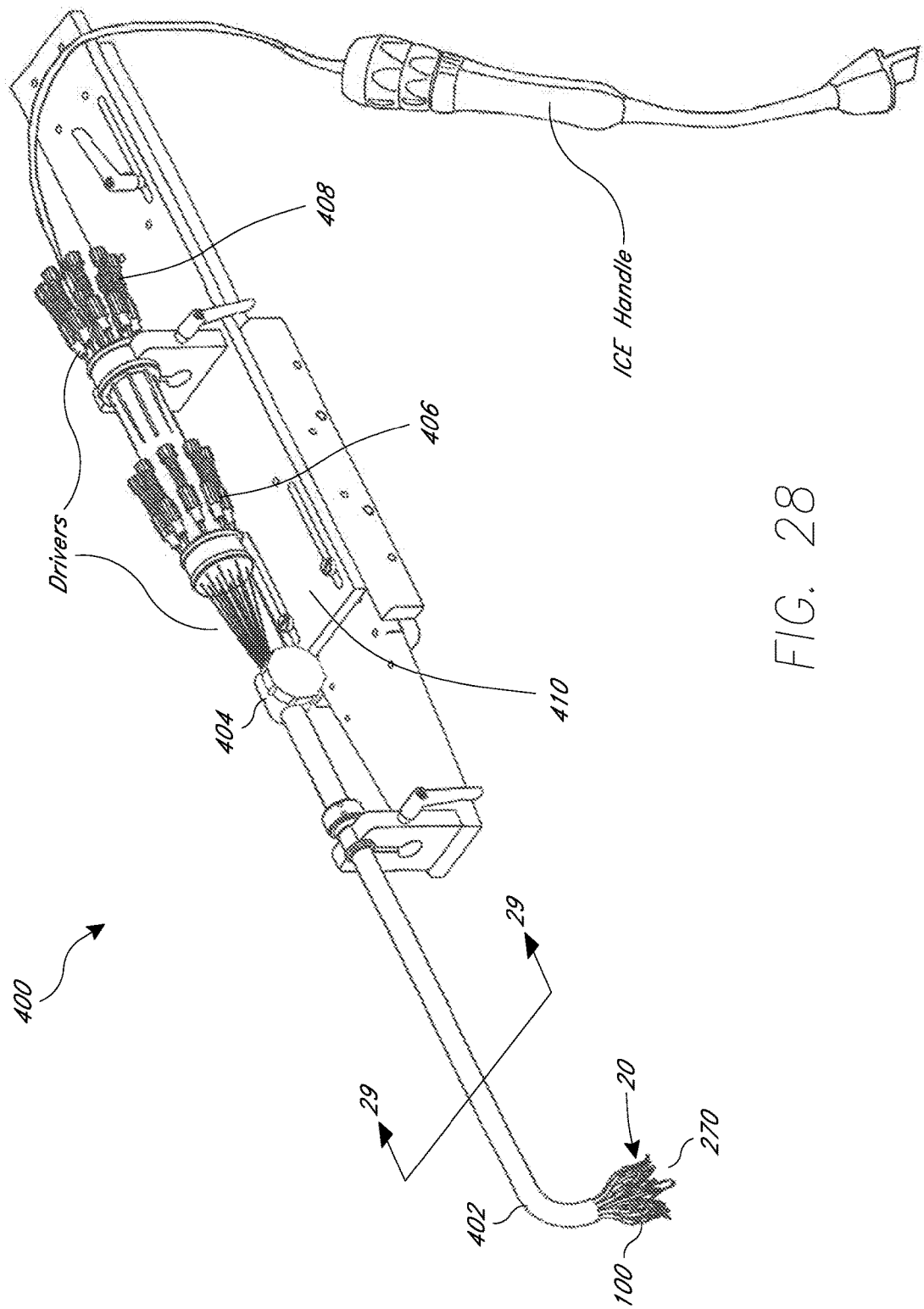
FIG. 28 is a perspective view of an embodiment of a delivery system having an implant attached thereto for delivery and securement of the implant to a heart valve annulus.

FIG. 28 is a perspective view of a delivery system 400 that may be used to deliver the various implants described herein. The delivery system 400 comprises a steerable sheath 402, a sheath steering knob 404, cinch knobs 406, anchor knobs 408, the implant 100 which may be any implant described herein, the ICE probe 270, all supported and secured to a base 410. The cinch knobs 406 and anchor knobs 408 are all spring loaded to maintain tension. Rotation of the anchor knobs 408 rotationally advance the helically wound anchors 20 into the annular tissue above the target heart valve. Cinch knobs 406 are manipulated by the operator to advance the collars and lock the frame of the implant 100 into a cinched position.

Figure 29:
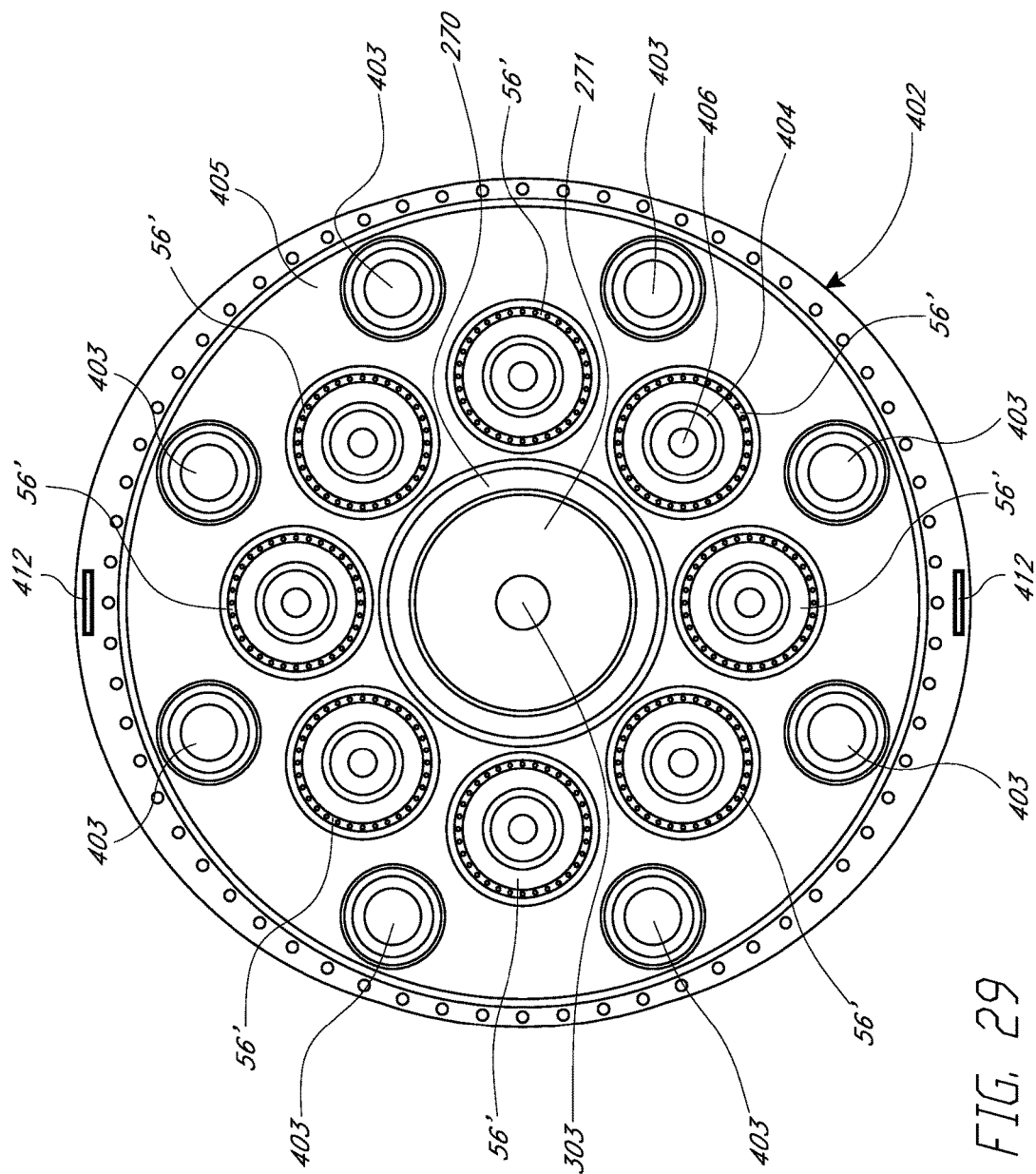
FIG. 29 is a cross section view taken along line 29-29 of FIG. 28 showing the internal features of a portion of the delivery system of FIG. 28.

FIG. 29 is a cross section taken along line 29-29 of FIG. 28. The pull wires 412 are attached to the sheath steering knob 404 to deflect the distal end of the sheath 402. The sheath 402 may be a steerable outer sheath 402, for example made of braided polymer or metal such as Nitinol or stainless steel. The ICE catheter shaft 270 may be centrally located with the guidewire lumen 303 located within the ICE catheter lumen 271. There are eight anchor driver wires 403, for example nitinol, circumferentially located within the sheath 402. The anchor driver wires 403 are located within anchor driver sheaths, for example laser cut hypotubes. There are eight pusher tubes 56', which may be braided, located around the ICE catheter shaft 270. The pusher tubes 56' may include a cinch retaining tube 404, for example a laser cut hypotube and a cinch retaining wire 407, for example nitinol.

Figure 30B:
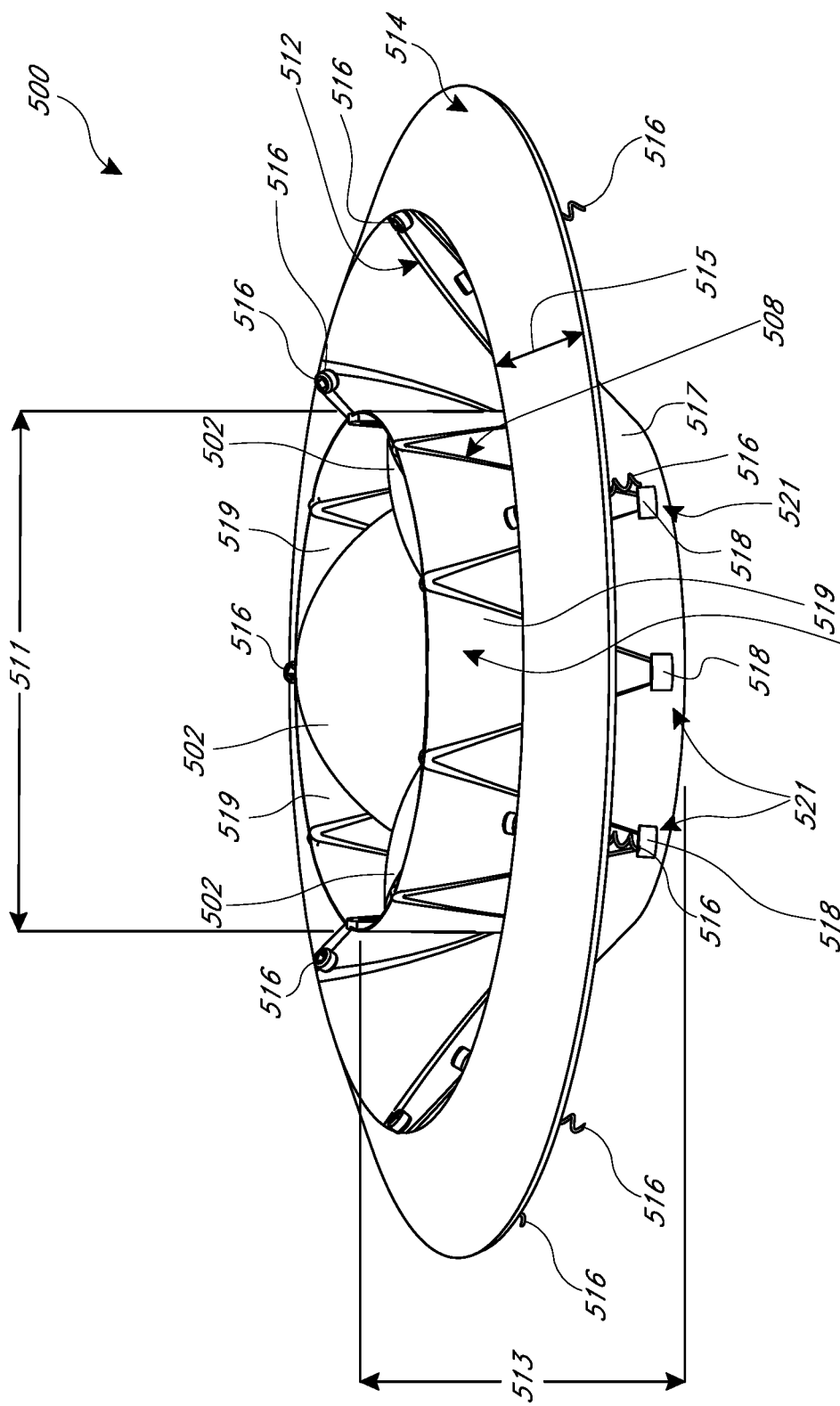
Figure 30C:
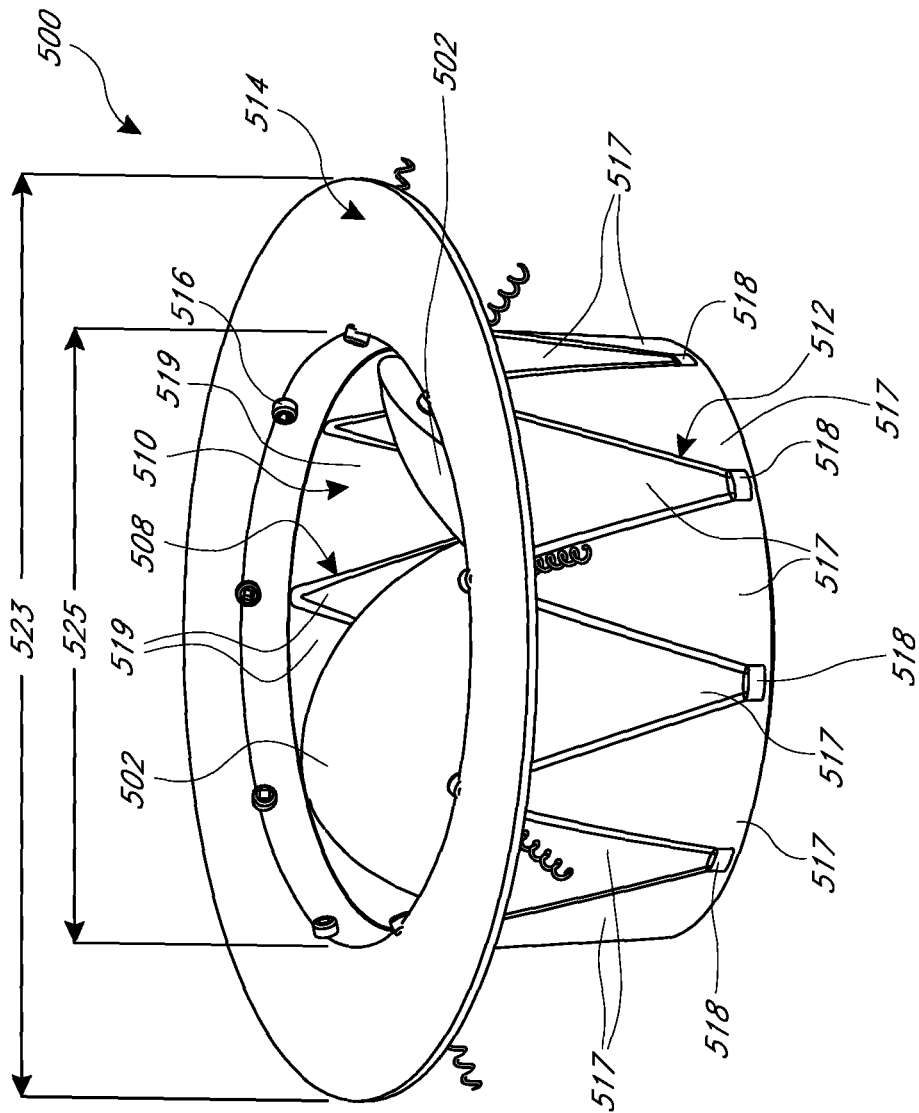

FIGS. 30A-30C are perspective views of an embodiment of an expandable replacement valve implant 500 shown in various states, i.e. configurations. FIG. 30A shows the replacement valve implant 500 in an unconstrained state. FIG. 30B shows the replacement valve implant 500 in a deployed and anchored state. FIG. 30C shows the replacement valve implant 500 in an anchored and cinched state.

The replacement valve implant 500 may be delivered with the various delivery systems and methods described herein. The replacement valve implant 500 may include an associated cinching structure. The replacement valve implant 500 is thus suited to treat multiple disease conditions. For example, the replacement valve implant 500 can treat mitral regurgitation developed as a consequence of cardiomyopathy and attendant dilation of the mitral valve annulus.

Moreover, the replacement valve implant 500 and cinching structure can treat failed or defective heart valve leaflets by replacing the native valve apparatus. Additionally, the replacement valve implant 500 and cinching structure can treat both mitral regurgitation and those patients with concomitant defects in the valve leaflets themselves.

The replacement valve implant 500 includes one or more non-native valve leaflets 502. The leaflets 502 may be mechanical or tissue-based such as porcine or bovine. The leaflets 502 replace the function of the defective heart valves by providing normal or otherwise acceptable blood flow regulation. The leaflets 502 may be configured to mimic the natural configuration of native leaflets. As shown, there are three leaflets 502. In some embodiments, there may be one, two, three or more leaflets 502. The leaflets 502 are coupled with housing and/or other features of the replacement valve implant 500, as described herein.

The replacement valve implant 500 includes an inner valve housing 510. The valve housing 510 may be a support for various features of the implant 500, such as the leaflets 502, one or more frames, struts, etc. The valve housing 532 is configured to extend into the valve annulus and contain the leaflets 502 therein. The leaflets 502 may be mechanically attached to the inner valve housing 510 by a variety of suitable means, including sutures, fasteners, adhesives, crimping, other means, or combinations thereof. The valve housing 510 forms an inner portion of the replacement valve implant 500 that connects with an outer portion, as described herein. The valve housing 510 may include an inner frame 508 and/or an inner barrier 519, as described herein.

The inner frame 508 may be analogous to other frames described herein, such as the frame 10, and thus be a structural member, include a tubular shape, have sinusoidal struts, etc. The inner frame 508 may be a variety of suitable materials, such as metal, preferably nitinol. After deployment from a delivery catheter and expansion to the unconstrained shape, the inner frame 508 may or may not change shape, size, etc. The inner frame 508 may be coupled with an outer frame 512, as described herein. Lower apices of the inner frame 508 may be coupled with lower apices of an outer frame 512. The inner frame 508 may be a portion of the outer frame 512. For example, the inner frame 508 may be part of the same continuous structure as the frame 512 and form an inner portion thereof.

The inner frame 508 may be coupled to or otherwise carry the inner barrier 519 to form the valve housing 510. The inner barrier 519 is a membrane-like material extending around the circumference of the valve housing 510. The inner barrier 519 is configured to extend into the valve annulus to contain the leaflets 502 within the annulus. The inner barrier 519 also acts to prevent leakage of blood flow around the replacement valve implant 500. The inner barrier 519 may comprise any of a variety of suitable materials, including ePTFE or a polyester material, such as Dacron. The inner barrier 519 may be coupled with the inner frame 508. The inner barrier 519 may be coupled with the inner frame 508 with a variety of suitable means, for example with sutures, mechanical attachments, embedding, other suitable features, or combinations thereof.

The inner barrier 519 may be carried by the radially inwardly or outwardly facing surfaces of the inner frame 508. As shown, separate segments of the inner barrier 519 may be coupled with the inner frame 508 in between struts of the inner frame 508. In some embodiments, the inner barrier 519 may be a single, continuous tubular membrane. For example, the inner barrier 519 may be provided entirely or mostly on the inside or internal diameter of the valve housing 510. In some embodiments, the inner barrier 519 may be provided entirely or mostly on the outside or external diameter of the valve housing 510. In some embodiments, there may be multiple barriers 519, such as an internal and an external inner barrier 519 each on opposite sides of the inner frame 508.

The illustrated replacement valve implant 500 includes an outer cinch frame 512. The outer frame 512 is coupled with one or more anchors 516 and one or more restraints such as collars 518. The outer frame 512, anchors 516 and collars 518 may be analogous to any of the other frames, anchors and collars described herein, for example the frame 10, anchors 20 and collars 18, respectively. The outer frame 512 may thus include a tubular shape, having a sidewall comprising sinusoidal or zigzag struts, with restraints, etc. The outer frame 512 may be coupled with the inner frame 508, for example at lower crowns 521 as shown. In some embodiments, the outer frame 512 may be coupled with the inner frame 508 in other manners, such as at upper crowns, etc. In some embodiments, the inner and outer frames 508, 512 may be part of the same monolithic material, for example different portions of a single, continuous wire or laser cut frame, etc. The outer frame 512 may compress for delivery within a delivery catheter, expand upon deployment from the catheter, and contract upon advancement of collars 518, as described herein. Contraction of the outer frame 512 may resize and/or re-shape the valve annulus. Activation of the restraints and/or manipulation of a control such as a pull wire advances the proximal end of the outer frame 512 radially inwardly toward the axis to reduce the inner diameter of the native valve annulus.

The anchors 516 may be located along a proximal end of the outer frame 512, as shown. In some embodiments, the anchors 516 may be in other locations along the circumference of the implant 500, for example located farther distally, located along the distal end of the implant 500, etc. The anchors 516 are inclined radially outward in the distal direction as deployed from the head of the anchors to the tissue-penetrating tips of the anchors. In some embodiments, the anchors 516 may have other orientations, for example substantially parallel to the axis, radially outward substantially transverse to the axis, inclined in the proximal or distal directions, or combinations thereof. The anchors 516 may engage either the inner frame 508 or the outer frame 512 of the implant 500, such as at a strut or apex of the outer frame 512. The anchors 516 act to secure the replacement valve implant 500 to tissue such that the replacement valve implant 500 extends through the native annulus and across the native valve. The anchors 516 may be helical as described herein and rotatably engage the tissue. The anchors 516 are shown retracted or pre-anchored in FIG. 30A. In FIG. 30B, the anchors 516 have been advanced into a tissue engagement orientation. In FIG. 30C, the outer frame 512 has been cinched such that the anchors 516 have now pulled the valve annulus inward to reduce the circumference of the annulus to conform to the implant 500 and reduce or eliminate the perivalvular space.

The collars 518 may be advanced along the outer frame 512 to adjust the circumference of the outer frame 512. The collars 518 may be advanced along upper or lower crowns of the outer frame 512. As shown, the collars 518 are coupled with the lower crowns 521. The collars 518 may be advanced along the lower crowns 521 similarly as described herein, for example, with respect to the implant 1 of FIGS. 1-4, etc.

The replacement valve implant 500 may include an outer barrier 517, which may be analogous to the inner barrier 519 of the valve housing 510. Thus, the outer barrier 517 of the frame 512 may be a material such as ePTFE or polyester, and may be selected to encourage or inhibit endothelial ingrowth. The outer barrier 517 may be elastic such that it can stretch and/or contract to reduce or prevent bunching or wrinkling of the material during and after delivery, deployment and cinching of the outer frame 512. The outer barrier 517 may be carried on the radially inwardly or outwardly surface of the outer frame 512. As shown, separate segments of the outer barrier 517 may be coupled with the frame 512 in between struts of the outer frame 512. In some embodiments, the outer barrier 517 may be a single, continuous membrane. For example, the outer barrier 517 may be provided on the inside or internal diameter of the outer frame 512. In some embodiments, the outer barrier 517 may be provided on the outside or external diameter of the outer frame 512. In some embodiments, there may be multiple barriers 517, such as an internal and external outer barrier 517. In some embodiments, there may not be any barrier 517.

The outer frame 512 and/or barrier 517 may form a generally frustoconical shape in the unconstrained state, as shown in FIG. 30A. Thus, the struts of the outer frame 512 and the barrier 517 are inclined outward in the proximal direction relative to the longitudinal axis of the replacement valve implant 500. The proximal edge of the barrier 517 is located radially farther outward relative to the distal edge of the barrier 517 in the unconstrained state. The outer frame 512 and/or outer barrier 517 may contact various portions of the native heart anatomy after deployment from the delivery catheter, such as the annulus wall. After the anchors 516 have engaged the tissue but before cinching the outer frame 512, the outer frame 512 and/or outer barrier 517 may still be in a generally frustoconical shape, as shown in FIG. 30B, leaving a perivalvular annular space but blocking perivalvular blood flow by the outer barrier 517 and/or inner barrier 519. After cinching the outer frame 512, the outer frame 512 and/or outer barrier 517 may form a generally cylindrical shape, as shown in FIG. 30C. In some embodiments, after cinching the outer frame 512, the outer frame 512 and/or outer barrier 517 may form other shapes, such as a generally frustoconical shape, other non-cylindrical shapes, etc.

The replacement valve implant 500 shown in FIGS. 30A-30B includes an annular atrial skirt or flange 514. The atrial flange 514 may be an extension of the barrier 517 in the radial or generally radial direction for at least about 2 mm, or about 5 mm, or more. The atrial flange 514 extends outward from a proximal edge of the outer frame 512. In some embodiments, the atrial flange 514 may instead extend outward from a distal edge of the outer frame 512, for example forming a "ventricular" flange situated inside the annulus and/or within the left ventricle (for a mitral valve implant). Such "ventricular" flange may be analogous to the atrial flange 514 as described herein. The atrial flange 514 and/or other flanges may further reduce and/or prevent of leakage of blood flow around the replacement valve implant 500, e.g. leakage in between the replacement valve implant 500 and the surrounding valve annulus. The atrial flange 514 may be a variety of suitable materials, such as ePTFE or a polyester material, for example Dacron. The atrial flange 514 may thus be a similar material as the outer barrier 517. In some embodiments, the atrial flange 514 may also include an extension of the outer frame 512 in the outward direction and providing support for the barrier material, such as the polyester material.

FIG. 30B shows the replacement valve implant 500 in its deployed and anchored state. As shown, the anchors 516 have been advanced through and engage the frame 508 and through the flange 514 and into tissue. Holes 503 are provided in or adjacent to the atrial flange 514 to allow the helically wound anchors 516 to pass therethrough and anchor into the annular tissue above the heart valve. The anchors 516 may also fixedly engage the flange 514. The anchors 516 may engage the atrial flange 514 such that a fixed connection is provided between the flange 514 and the respective anchor 516 before and/or after advancement of the anchors 516 therethrough. The flange 514 has a generally annular shape around the circumference of the implant 500. The flange 514 may be generally circular, or other rounded or non-rounded shapes. The flange 514 maybe symmetric or asymmetric with respect to the axis or with a plane that includes the axis The replacement valve implant 500 may have a variety of suitable dimensions. In the deployed and anchored state, and/or the deployed and unanchored state, and/or in the anchored and uncinched state, and/or in the anchored and cinched state, the valve housing 510 may have a height measured along the axis 513 in the range of about twenty millimeters to about thirty millimeters, although such height can vary. In some embodiments, in these various states the valve housing 510 may have a height in the range of about ten millimeters to about fifty millimeters. Referring to FIGS. 30A-30B, the inner diameter 511 of the valve housing 510 may be within the range of about twenty-five millimeters to about thirty millimeters, although such diameter can be varied. In some embodiments, the inner diameter 511 of the valve housing 510 may be within the range of about fifteen millimeters to about sixty millimeters. Referring to FIG. 30B, the atrial flange 514 may have a radial width 515 between about five millimeters and about thirty millimeters. In some embodiments, the atrial flange 514 may have a width 515 between about ten millimeters and about twenty millimeters wide. Referring to FIG. 30C, depending on the disease state(s), the cinch frame 512 can have an outer diameter 523 from about forty millimeters to about eighty millimeters. Larger diameters may be implemented, for example, if the disease state is or includes a dilated heart valve annulus as incidence of the patient's cardiomyopathy. The inner diameter 525 of the cinch frame 512, which may be measured in some embodiments from anchor 516 head to opposite anchor 516 head, may range from about thirty millimeters to about sixty millimeters, or in some embodiments from about fifteen millimeters to about one hundred millimeters, in the cinched orientation.

After the replacement valve implant 500 is anchored in place, it is cinched as shown in FIG. 30C. Cinching may be accomplished by a cinching mechanism on the deployment catheter, followed by advancing the collars 518 to achieve retention. Alternatively, cinching may be accomplished by manipulation and movement of collars 518. The various cinching techniques described herein may be employed. The replacement valve implant 500 may encourage tissue ingrowth after implantation. For example, the inner our outer frame 508, 512, the inner barrier 519, the outer barrier 517, other features of the implant 500, or combinations thereof, may be configured to facilitate tissue ingrowth and further securement of the implant 500 within the heart.

Figure 31:
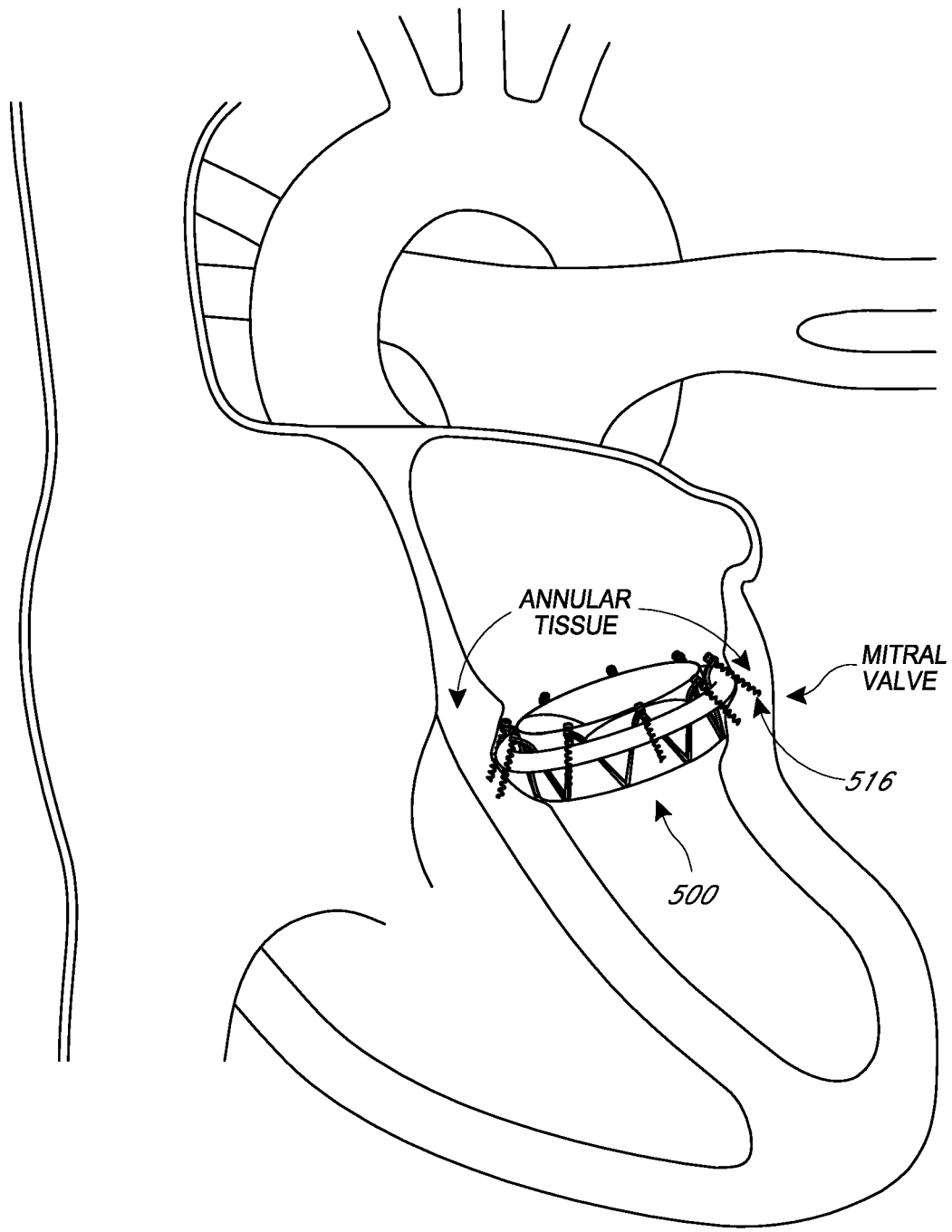
FIG. 31 is a cross-section view of a heart showing the replacement heart valve implant of FIGS. 30A through 30C deployed across a native mitral valve of the heart.

FIG. 31 illustrates the replacement valve implant 500 positioned, anchored, cinched and implanted in the annular tissue above and proximate the target heart valve. For illustration purposes, the replacement valve implant 500 has been deployed across the native mitral valve, with the atrial flange 514 blocking or at least substantially blocking paravalvular leakage around the replacement valve implant 500.

The replacement valve implant 500 is in sealing engagement with the atrial wall surrounding the native valve, which in some embodiments may be due in part to atrial blood pressure.

Figure 32A:
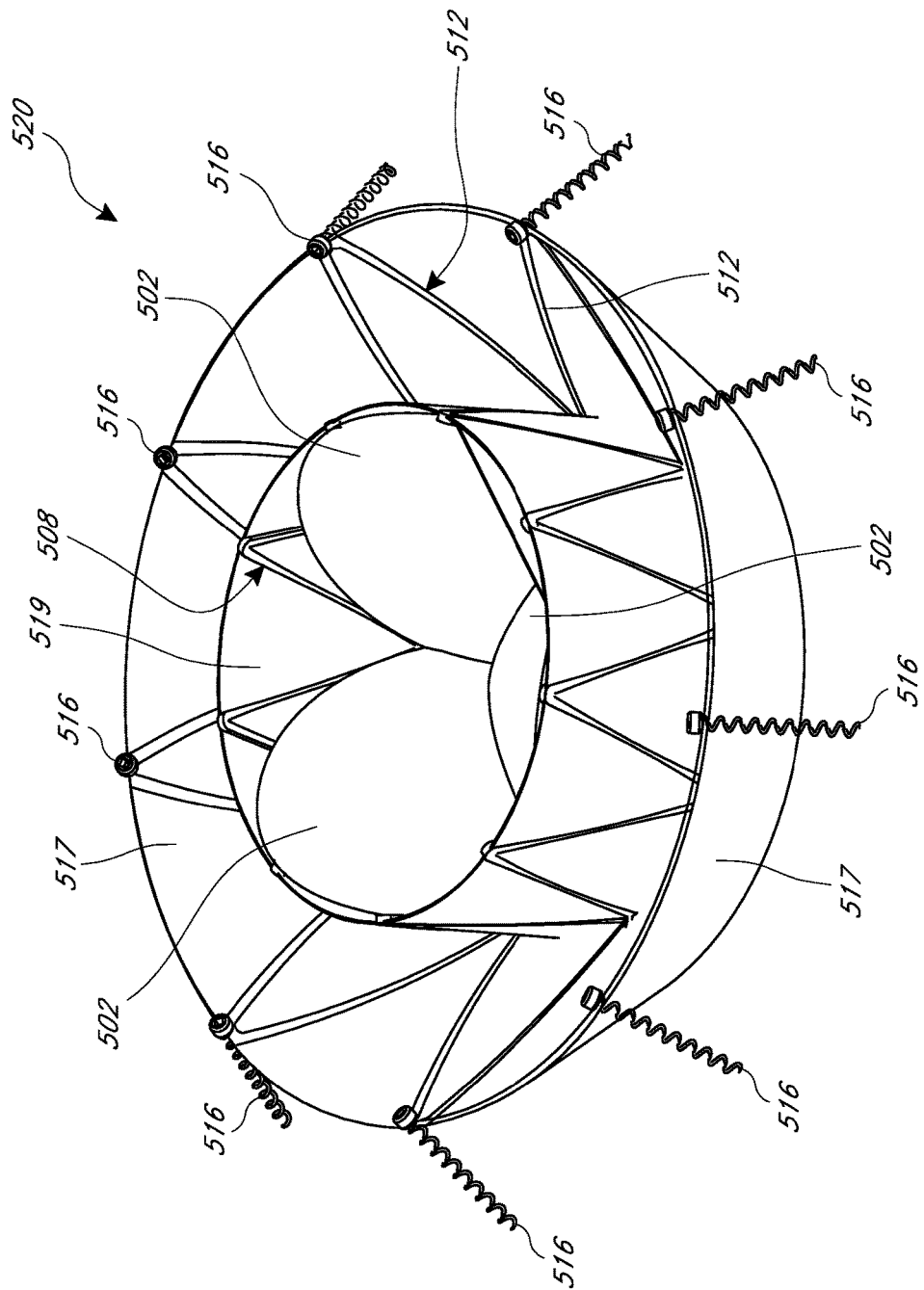
FIGS. 32A and 32B are perspective views of an embodiment of a replacement heart valve implant with anchors coupled to upper crowns and shown, respectively, in an anchored state and a cinched state.
Figure 32B:
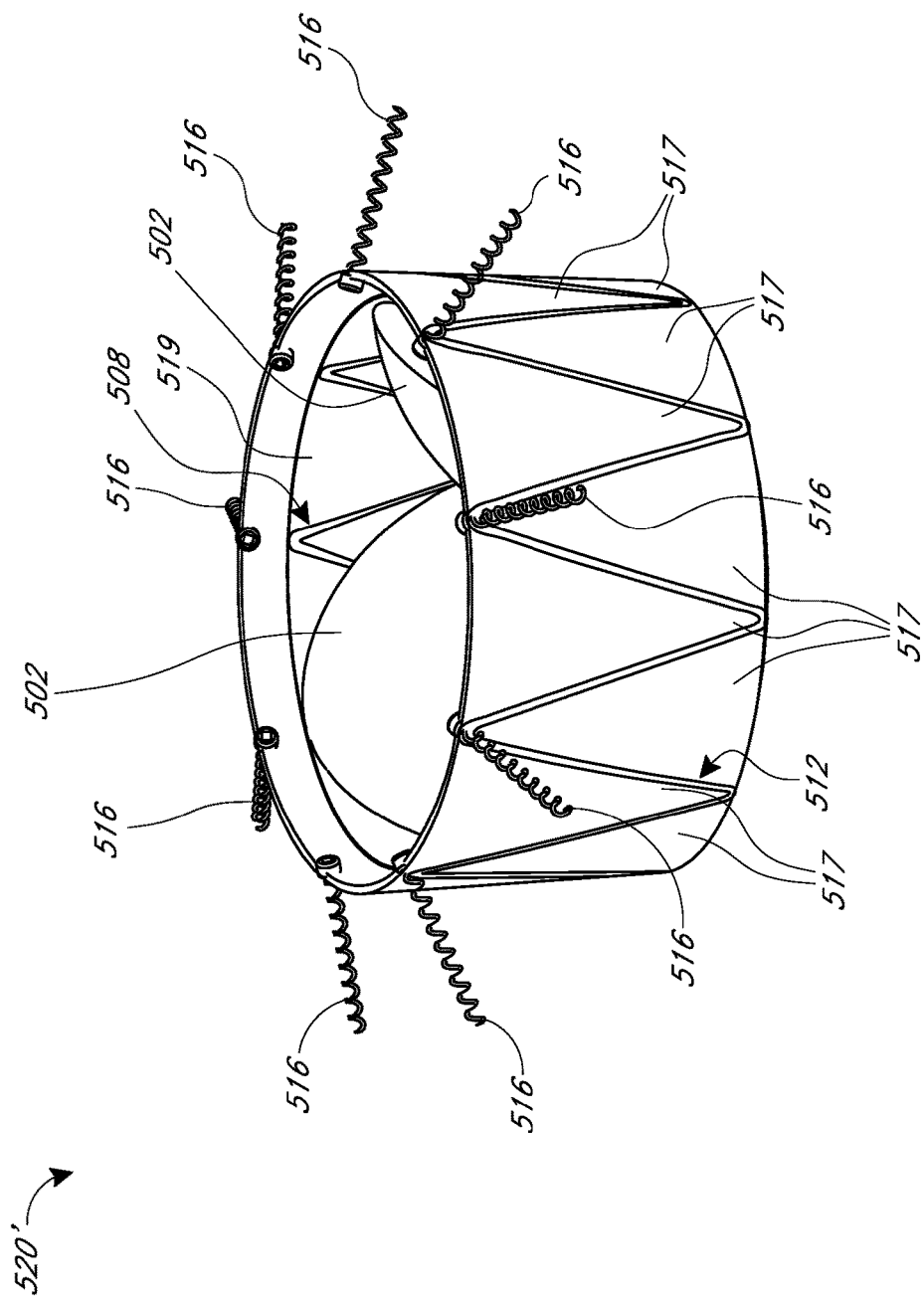

While the atrial flange 514 provides additional sealing in the atrium, in some embodiments such additional sealing may not be included. FIGS. 32A and 32B are perspective views of embodiments of heart valve replacements 520 and 520' without the additional sealing or atrial flange 514 and shown, respectively, in an unconstrained state and in a cinched state. Further, the heart valve replacement 520 includes the outer barrier 517 located on the outside of the outer frame 512, while the heart valve replacement 520' includes the outer barrier 517 located on the inside of the outer frame 512. The heart valve replacements 520 and 520' may otherwise be analogous to the heart valve replacement 500. Like reference numerals with respect to FIGS. 30A through 30C thus represent like elements in FIGS. 32A and 32B. After being anchored in position as shown in FIG. 32A, the collars are actuated, in a manner similar to that of FIG. 30C, to cinch the replacement valve 520 as shown in FIG. 32B. While nine anchors 516 have been shown with respect to the replacement valve embodiments of FIGS. 30 through 32, it is understood that the number of such anchors 516 can be varied. In some embodiments, such variance of the number of anchors 516 can range from three to eighteen. In some embodiments, the number of anchors 516 can vary in multiples of three.

Figure 33A:
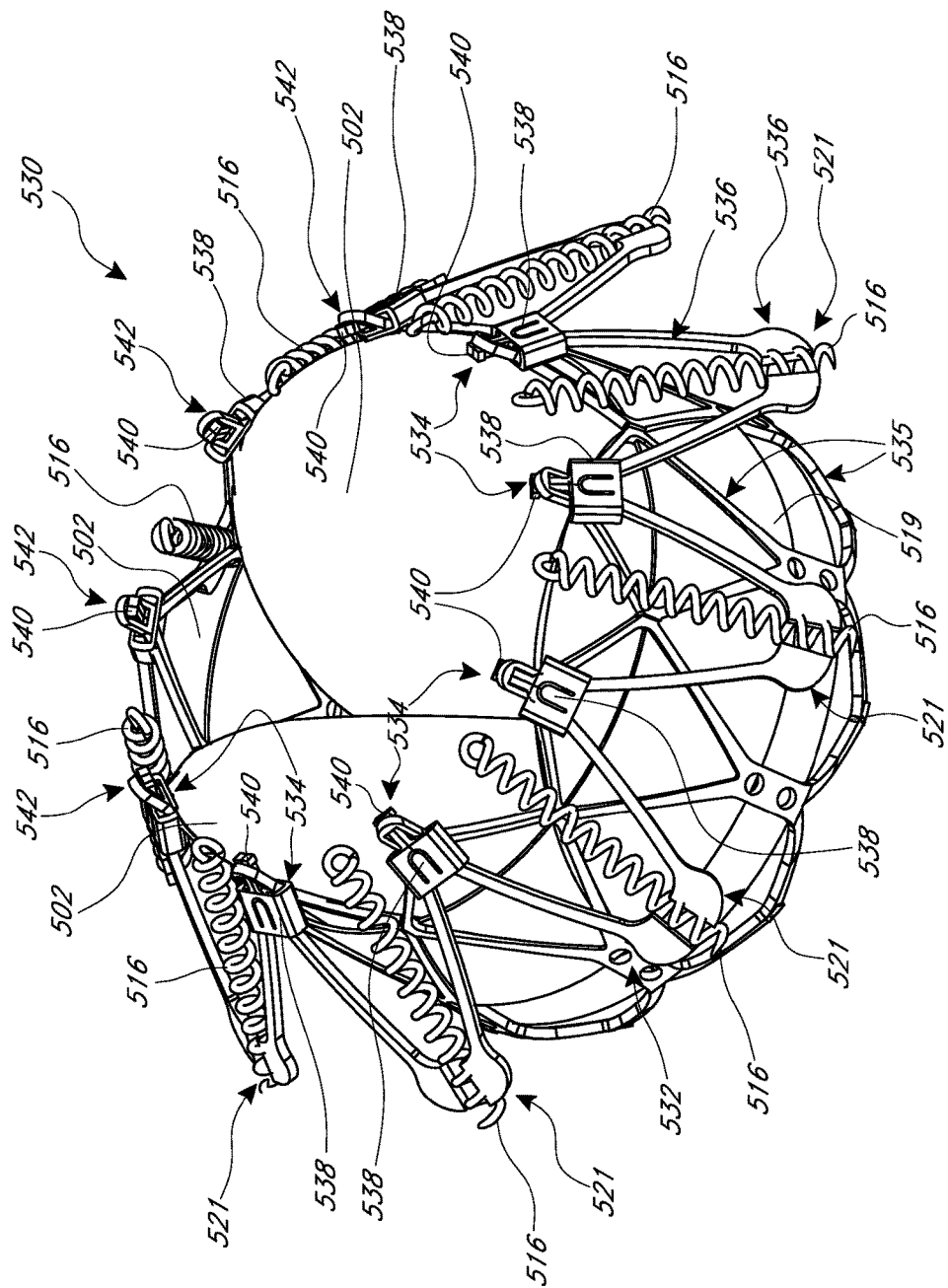
FIGS. 33A and 33B are perspective and side views of an embodiment of a replacement heart valve implant having a cinch frame and a housing and shown, respectively, in a deployed, unconstrained state and in an anchored, cinched and locked state.
Figure 33B:
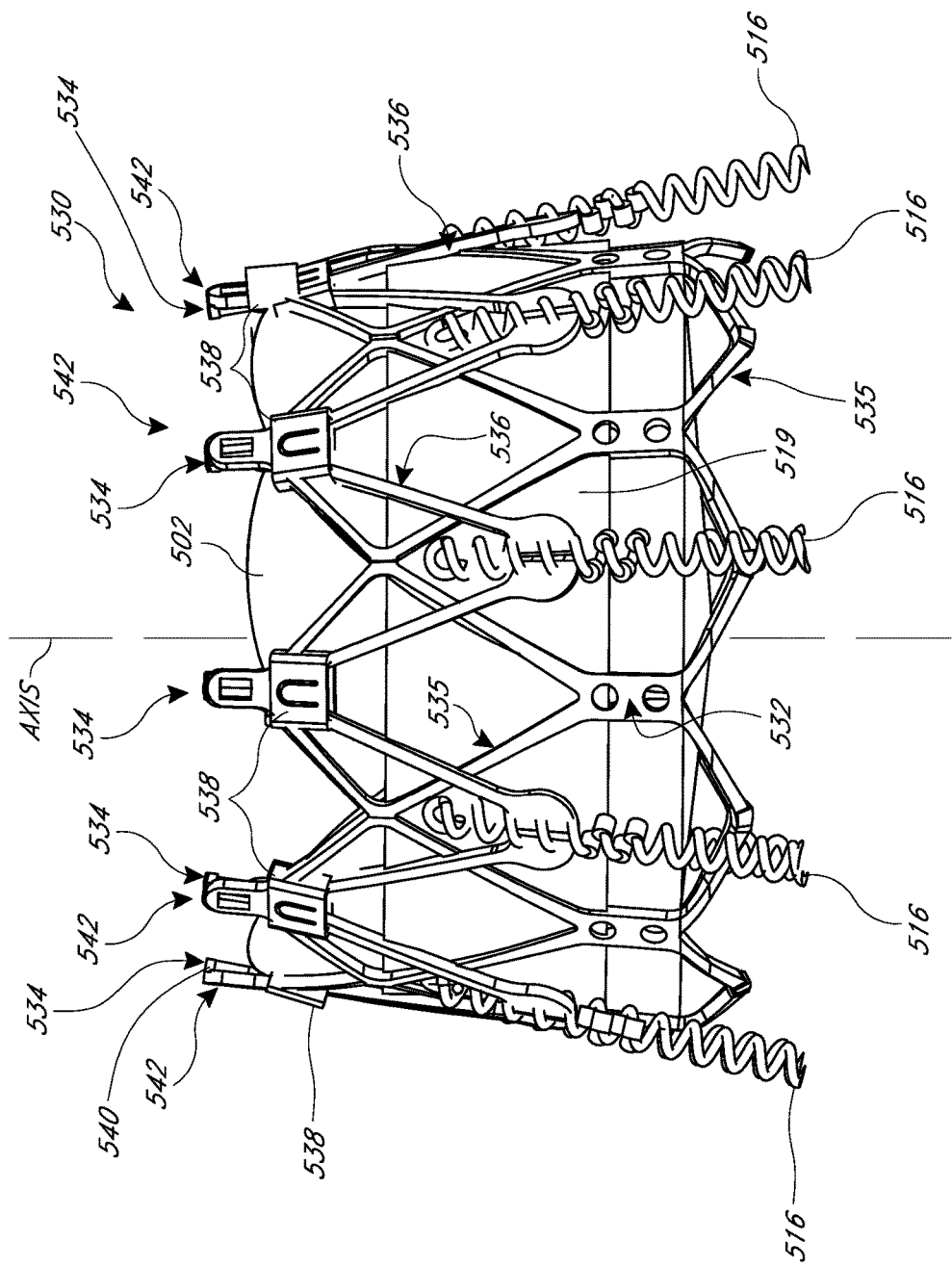

Another embodiment of a replacement valve implant 530 is depicted in FIGS. 33A and 33B. FIG. 33A shows the replacement valve implant 530 in an unconstrained and unanchored state and FIG. 33B shows the replacement valve implant 530 in an anchored, cinched and locked state. The replacement valve implant 530 may include features analogous to features described with respect to other implants herein, for example the implant 1, 500, 520, 520', etc.

The replacement valve implant 530 includes an inner valve housing 532 and an outer frame 536. The valve housing 532 may be analogous to the valve housing 510. The valve housing 532 may include one or more leaflets 502, which may be analogous to the leaflets 502 as described with respect to the replacement valve implant 500. The valve housing 532 may include an inner frame 535 as shown, which may be formed of nitinol. The inner frame 535 may thus have proximal, generally diamond-shaped segments that are adjacent distal, irregular hexagonal-shaped segments extending circumferentially in a generally tubular shape about an axis, as indicated in FIG. 33B. The valve housing 532 has a series of upper crowns 542 with openings therethrough. The openings may be circular or other shapes. The openings in the upper crowns 542 may engage with one or more features of an outer cinch frame 536, such as extensions 540 that extend from upper crowns of the outer frame 536.

The outer frame 536 may be analogous to other frames or outer frames described herein, for example, the frames 10, 512, etc. The outer frame 536 is coupled with one or more anchors 516 and one or more restraints such as collars 518. The outer frame 536 may be coupled with the valve housing 532, for example the inner frame 535, at the upper (proximal) crowns 542, as described. In some embodiments, the outer frame 536 may be coupled with the inner frame 535 in other manners, such as at lower crowns, etc. In some embodiments, the inner and outer frames 535, 536 may be part of the same monolithic material, for example different portions of a single, continuous frame, etc.

The outer frame 536 may compress for delivery within a delivery catheter, expand upon deployment from the catheter, and contract upon advancement of collars 518, as described herein. The outer frame 536 in an unconstrained state, as shown in FIG. 33A, inclines radially outward in a distal direction from a proximal end of the valve housing 532. Contraction of the outer frame 536 to a cinched state, as shown in FIG. 33B, may resize and/or re-shape the native valve annulus. The outer frame 536 may advance radially inwardly toward the axis to reduce the inner diameter of the native valve annulus into conformance with the inner frame 535. The outer frame 536 may include collars 538 at the upper crowns 534. The collars 538 may be advanced distally to cinch the implant 530 to cause the outer frame 536 to advance radially inward. The collars 538 may interact with the outer frame 536 to cinch the outer frame 536 as described herein with respect to other collars and frames, such as the collars 18 and the frame 10, etc.

The extensions 540 include perpendicularly disposed tabs generally forming T-Bar extensions on the upper crowns 534 of the outer frame 536. The extensions 540 engage with the openings in the upper crowns 542 of the valve housing 532 to pivotally secure the outer frame 536 to the valve housing 532. The extensions 540 may be inserted into the openings during assembly of the replacement valve implant 530. The anchors 516 are moveably engaged with lower crowns 521 that are located in between upper crowns 542 of the valve housing 532. The anchors 516 may engage with the lower crowns as described herein with respect to other anchors and crowns, such as the anchors 20 and lower crowns 16, etc. After the anchors 516 have been rotationally advanced into the annular heart valve tissue, cinching of the outer frame 536 as shown in FIG. 33B will draw the annular tissue or portions thereof toward the valve housing 532. Further, in the cinched state shown in FIG. 33B, portions of the native annulus tissue may be drawn radially inward and/or upward (proximally) in between the outer frame 536 and the valve housing 532. This action will reduce the potential for paravalvular leaking and migration of the replacement valve implant 530. In some embodiments, the valve housing 532 may be tapered, for example having a smaller diameter on the atrial side of the valve orifice and a larger diameter on the ventricular side to facilitate blood flow through and across the replacement heart valve 530.

Relatively large diameter catheter shafts are described herein that may be used to deliver the re-sizing implants, such as the implant 1 and others, or valve replacements, such as the valve 500 and others, as described herein. These large diameter catheter shafts may include features that mitigate or eliminate the tendency to kink, wrinkle or tear when attempting a sharp bend radius. FIGS. 34A through 37 show various embodiments of sections of steerable catheters that may be used with the various implants described herein. The features of the steerable catheters improve the catheter's ability to maneuver tight bends to a position above and proximate and/or into the mitral valve annulus or tricuspid valve annulus.

Figure 34B:
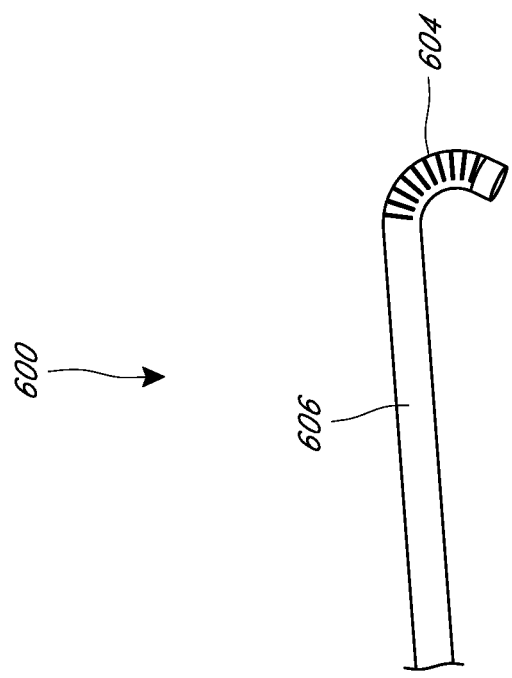
FIGS. 34A and 34B are side views of an embodiment of a distal section of a steerable catheter shown in straight and flexed states, respectively, that may be used to deliver the various implants described herein.
Figure 34A:
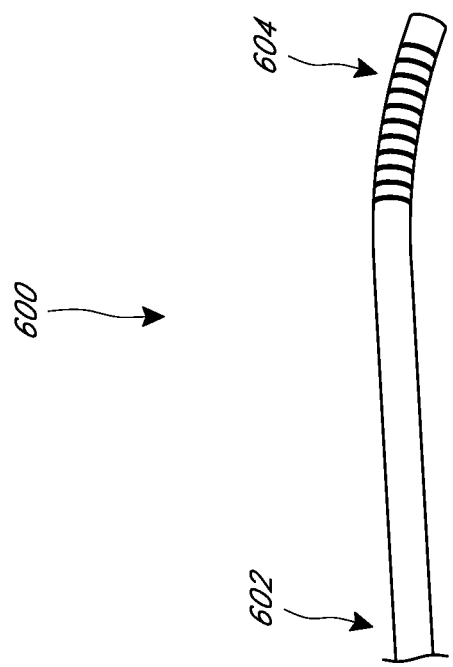

FIGS. 34A and 34B are side views of an embodiment of a distal section 600 of a steerable catheter 602 shown in straight and flexed states, respectively, that may be used to deliver the various implants described herein. The steerable catheter 602 may be used in the various delivery systems and methods described herein. The steerable catheter 602 has a distal end 604 and intermediate section 606. The distal end 604 may be a deflectable section, as described herein. The distal end 604 may include a length of the catheter 602 extending from the distal tip. For example, the deflectable section of the distal end 604 may include a length of five or ten or fifteen centimeters, or more or less, of the catheter 602 as measured from the distal tip in a proximal direction. The intermediate section 606 may take the form of a shaft section reinforced with a braid or slotted tubing. The catheter 602 may include a proximal end opposite the distal end 604. Only a portion of the catheter 602 is shown for clarity. The proximal end of the catheter 602 may be coupled with a proximal manifold having a deflection control. The catheter 602 and/or features thereof may be implemented with the various catheters and delivery systems described herein, for example those shown in and/or described with respect to FIGS. 22A-25E, or others.

Figure 35A:
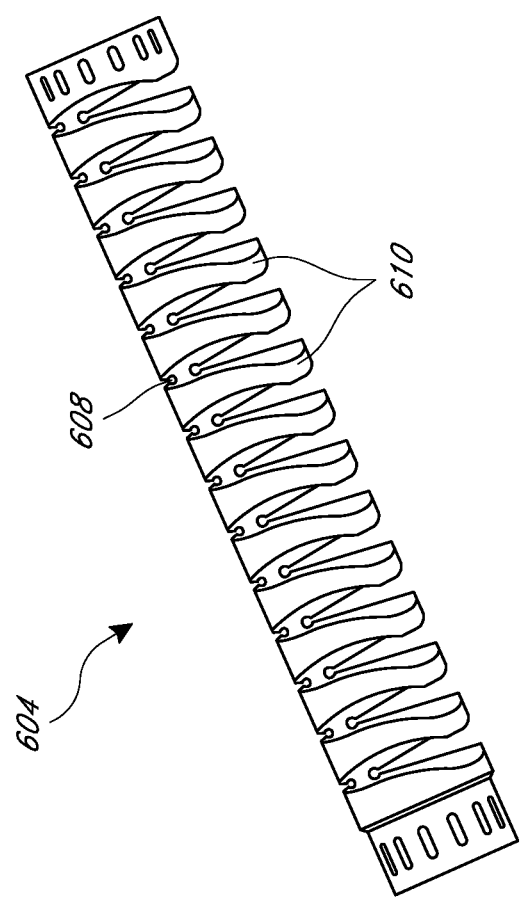

FIGS. 35A and 35B depict an embodiment of the distal section 604 that may be used with the steerable catheter 602, shown in straight and flexed states, respectively. The distal section 604 has a single spine 608 running along its outer curve, and a series of support ribs 610 formed or cut into the inner curve. The distal section 604 may be formed of a flexible metal tube, such as nitinol. The distal section 604 may incorporate pull wires for control of the delivery system. Alternatively, the pull wire may be looped around the distal section's distal tip and back toward the proximal part of the catheter 602. The support ribs 610, with voids therebetween, allow the distal section 604 to achieve a tight bend radius. This flexed state of the distal section 604 is realized with minimal protrusion of the support ribs 610 into the inner diameter or outer diameter of the distal section 604. Moreover, the spine 608 provides a smooth surface on the outer curve of the distal section 604 minimizing friction or interference with heart tissue during delivery and positioning of the catheter and implant.

Figure 36B:
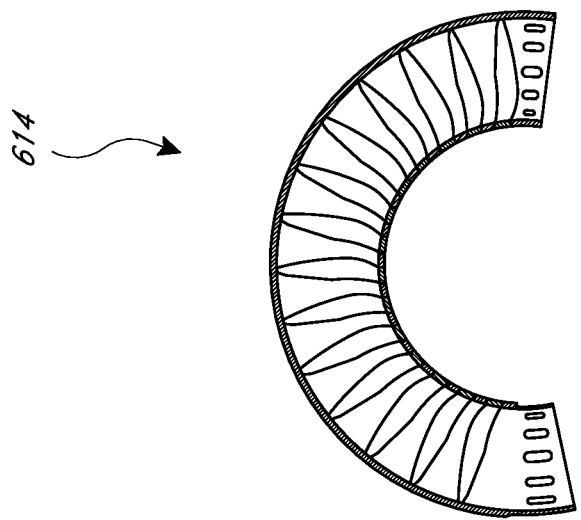
FIGS. 36A and 36B are side views of another embodiment of a distal section of a steerable catheter having a thin film that may be to deliver the various implants described herein.
Figure 36A:
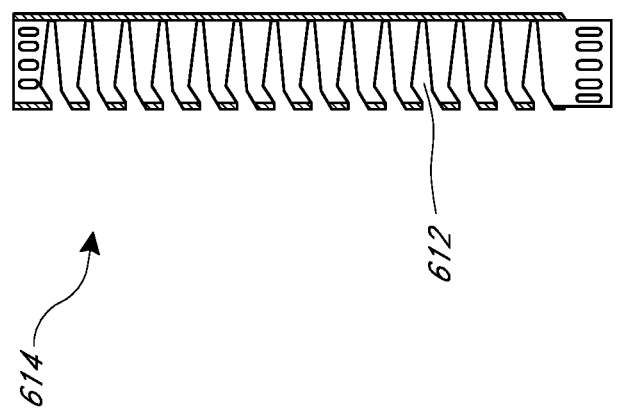

FIGS. 36A and 36B illustrate another embodiment of a distal section 614 that may be used with the steerable catheter 602. Here, the distal section 614 may be a flexible metal tube that is wrapped or encased in a thin film 612 or polymeric material such as Teflon, pTfe, nylon or other thin material. This thin film 612 encapsulation does not restrict the flexibility of the distal section 614 but does provide for smoother delivery and transition into and out of a guide catheter. The thin film 612 may be stretchable or designed to fold in on itself, somewhat similar to an accordion, when flexed as shown in FIG. 36B.

Figure 37:
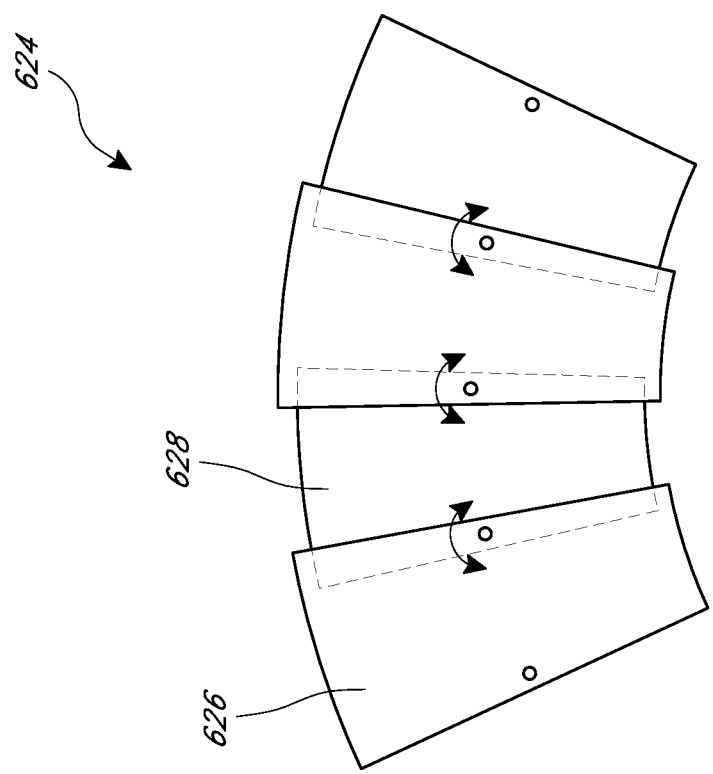
FIG. 37 is a side view of another embodiment of a distal section of a steerable catheter having nesting elements that may be used to deliver the various implants described herein.

FIG. 37 shows another embodiment of a distal section 624 that may be used with the steerable catheter 602. Here, distal section 624 comprises a series of larger elements 626 and smaller elements 628. The smaller elements 628 nest within the larger elements 626. All elements may slide over one another. When the distal section 624 is in a straight state, the metal elements are most overlapped. As the distal section 624 is actuated towards the flexed state, as shown for example in FIG. 37, there may be progressively less overlap of the elements particularly on the outer curve of the distal section 624.

The embodiments of the distal and intermediate sections of the catheter 602 are intended for use in the delivery and implant of both the ring-like embodiments and the replacement valve embodiments described herein. In treating the mitral valve, for example, once the catheter is passed through the septum separating the right and left atria, it is guided slightly upwardly towards the upper reaches of the left atrial chamber. It is then bent significantly in a direction downward towards the mitral annulus, aligning the distal end and the implant with the mitral annulus. The devices, systems and methods described herein allow such bending to occur without kinking or wrinkling which would otherwise impede delivery of the implant.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. An implant for reducing heart valve regurgitation comprising:
    a frame having upper crowns, lower crowns and struts between the upper and lower crowns, the frame having a tissue engaging configuration having a tissue engaging diameter and an annulus remodeling configuration where the frame has an annulus remodeling diameter that is less than the tissue engaging diameter;
    a plurality of anchoring members coupled with the lower crowns of the frame for engaging cardiac tissue proximate the heart valve annulus; and
    a plurality of collars coupled with the upper crowns of the frame, wherein when force is applied to the collars, the collars slide along the upper crowns and the struts to move the frame from the tissue engaging configuration towards the annulus remodeling configuration and wherein each collar includes at least one flex section configured to reduce friction between the collar and the upper crowns and the struts.

2. The implant of claim 1, wherein the plurality of anchoring members are helically wound anchoring members and the lower crowns of the frame are adapted to threadingly receive the helically wound anchoring members.

3. The implant of claim 2, wherein the helically wound anchoring members further include anchoring heads for engagement with actuators to rotationally advance the helically wound anchoring members in the cardiac tissue to anchor the frame into the cardiac tissue.

4. The implant of claim 3, further comprising abutments on each of the anchor heads to engage with the struts and the lower crowns to limit travel of the helically wound anchoring members.

5. The implant of claim 2, wherein the helically wound anchoring members have sharpened tips to facilitate penetration of the helically wound anchor members into the cardiac tissue.

6. The implant of claim 1, further comprising at least one tab on each of the collars, wherein the tabs are inwardly biased to engage with the upper crowns when the collars are slid over the upper crowns and struts.

7. The implant of claim 6, wherein each of the collars comprises a plurality of the tabs, and wherein the plurality of tabs can be advanced over the upper crowns and struts to selectively vary the annulus remodeling diameter of the frame.

8. The implant of claim 7, wherein the plurality of tabs are vertically disposed on an outwardly facing portion of the collars and comprises a lowermost tab, wherein the lowermost tab is initially disposed and engaged with an underside of the upper crown.

9. The implant of claim 1, further comprising a groove formed on an outwardly facing side of the upper crowns and at least one tab on each of the collars wherein the tabs are inwardly biased to engage with the groove.

10. The implant of claim 1, further comprising a plurality of pusher members that engage with the plurality of collars to forcibly advance the collars over the upper crowns and struts to reduce the diameter of the frame.

11. The implant of claim 1, wherein the at least one flex section on each collar is configured to facilitate advancement of the collars over the upper crowns and struts.

12. The implant of claim 1, wherein the frame defines a longitudinal axis, and wherein the lower crowns and anchoring members received in the lower crowns are inclined outwardly in a distal direction at an angle between about 30° to about 60° with respect to a portion of the axis that extends distally below the implant.

13. A delivery system for delivering an implant for reducing heart valve regurgitation, the delivery system comprising:
    the implant, wherein the implant comprises:
        a frame having upper crowns, lower crowns and struts between the upper and lower crowns, the frame having a tissue engaging configuration with a tissue engaging diameter, and an annulus remodeling configuration where the frame has an annulus remodeling diameter less than the tissue engaging diameter;
        a plurality of anchoring members coupled with the lower crowns of the frame for engaging cardiac tissue proximate the heart valve annulus; and
        a plurality of collars coupled with the upper crowns of the frame, wherein when force is applied to the collars, the collars slide on the upper crowns and the struts to move the frame from the tissue engaging configuration towards the annulus remodeling configuration and wherein each collar includes at least one flex section configured to reduce friction between the collar and the upper crowns and the struts;
    a delivery catheter releasably attached to the implant and configured to deliver the implant to a position proximate the heart valve annulus; and
    an imaging catheter comprising a distal end configured to extend proximate the heart valve annulus and to capture one or more images therein of the position of the implant relative to the heart valve annulus.

14. The delivery system of claim 13, further comprising a plurality of actuating members for engaging corresponding anchoring members of the implant to cause the anchoring members to penetrate and advance into the cardiac tissue to anchor the frame in position proximate the heart valve annulus.

15. The delivery system of claim 13, further comprising a plurality of pusher members for engaging corresponding collars of the implant to forcibly advance each collar over its respective upper crown and struts thereby reducing the diameter of the frame and the valve annulus.

16. The delivery system of claim 13, further comprising means for centering the imaging catheter with respect to the implant.

17. The delivery system of claim 13, wherein the distal end of the imaging catheter comprises longitudinally disposed and circumferentially disposed ultrasound transducers.

18. The delivery system of claim 13, wherein the frame defines a longitudinal axis, and wherein the lower crowns and anchoring members received in the lower crowns are inclined outwardly in a distal direction at an angle of approximately 45° with respect to a portion of the axis that extends distally below the implant.

19. The delivery system of claim 18, further comprising:
a loop encircling the frame proximate its lower crowns; and
a constricting actuator to constrict the loop to facilitate collapse and loading of the implant into the delivery system.

20. The delivery system of claim 19, wherein each of the collars comprises a plurality of tabs that are inwardly biased to engage with corresponding undersides of the upper crowns when the collars are slid over the upper crowns and struts by the pusher members, and wherein after the frame has been anchored into the cardiac tissue, the loop is constricted to determine the desired reduction in diameter of the frame prior to advancing the collars and tabs over the respective upper crowns and struts.

21. A method of reducing the size of an enlarged heart valve annulus comprising the steps of:
delivering an implant in a delivery system to a site above and proximate the enlarged heart valve annulus, the implant having a proximal end and a distal end;
releasing the implant from the delivery system to allow the implant to take on a tissue engaging diameter;
anchoring the distal end of the implant into cardiac tissue proximate and above the enlarged heart valve annulus;
translating a plurality of collars over corresponding upper crowns of the proximal end of the implant to reduce the tissue engaging diameter to an annulus remodeling diameter, thereby reducing the size of the enlarged heart valve annulus, wherein each collar includes at least one flex section configured to reduce friction between the collar and the upper crowns; and
disengaging the anchored and reduced diameter implant from the delivery system.

22. A heart valve replacement implant comprising:
a replacement valve having a plurality of replacement valve leaflets;
a tubular valve housing fixedly attached to the replacement valve leaflets;
a cinch frame connected to and circumferentially surrounding the tubular valve housing, the cinch frame having upper crowns, lower crowns and struts between the upper and lower crowns, the cinch frame configurable between a tissue engaging configuration wherein opposing upper crowns are separated by a tissue engaging diameter and an annulus remodeling configuration wherein opposing upper crowns are separated by an annulus remodeling diameter that is less than the tissue engaging diameter;
a plurality of anchoring members coupled with the upper crowns of the cinch frame for engaging cardiac tissue proximate the heart valve annulus; and
a plurality of collars coupled with the lower crowns of the cinch frame, wherein when force is applied to the collars, the collars slide on the lower crowns and the struts to reconfigure the cinch frame from the tissue engaging configuration towards the annulus remodeling configuration and wherein each collar includes at least one flex section configured to reduce friction between the collar and the upper crowns and the collars.

23. The heart valve replacement implant of claim 22, further comprising a sealing flange on the cinch frame and disposed on the atrial side of the heart valve when the heart valve replacement system is implanted.

24. A heart valve replacement implant comprising:
a replacement valve having a plurality of replacement valve leaflets;
a tubular valve housing fixedly attached to the replacement valve leaflets;
a cinch frame connected to and circumferentially surrounding the tubular valve housing, the cinch frame having upper crowns, lower crowns and struts between the upper and lower crowns, the cinch frame configurable between a tissue engaging configuration wherein opposing lower crowns are separated by a tissue engaging diameter and an annulus remodeling configuration wherein opposing lower crowns are separated by an annulus remodeling diameter that is less than the tissue engaging diameter;
a plurality of anchoring members coupled with the lower crowns of the cinch frame for engaging cardiac tissue proximate the heart valve annulus; and
a plurality of collars coupled with the upper crowns of the cinch frame, wherein when force is applied to the collars, the collars slide on the upper crowns and the struts to reconfigure the cinch frame from the tissue engaging configuration towards the annulus remodeling configuration and wherein each collar includes at least one flex section configured to reduce friction between the collar and the upper crowns and the struts.

25. The heart valve replacement system of claim 24, wherein the tubular valve housing has a proximal end and a distal end, and the upper crowns of the cinch frame have extensions adapted to be received in openings in the proximal end of the valve housing such that the upper crowns and the cinch frame pivot about the proximal end of the valve housing.

* * * * *